US012570732B2

(12) United States Patent (10) Patent No.: US 12,570,732 B2
Mendiratta et al. (45) Date of Patent: Mar. 10, 2026

(54) ANTI-PROPERDIN ANTIBODIES AND PREPARATION THEREOF

(71) Applicant: Zydus Lifesciences Limited, Ahmedabad (IN)

(72) Inventors: Sanjeev Kumar Mendiratta, Ahmedabad (IN); Arun Singh, Ahmedabad (IN); Ramkrashan Kasera, Ahmedabad (IN); Aashini Parikh, Ahmedabad (IN); Jimit Upadhyay, Ahmedabad (IN); Pankaj Kalita, Ahmedabad (IN); Dilip Bandyopadhyay, Ahmedabad (IN); Ashu Shah, Ahmedabad (IN)

(73) Assignee: ZYDUS LIFESCIENCES LIMITED, Ahmedabad (IN)

( * ) Notice: Subject to any disclaimer, the term of this patent is extended or adjusted under 35 U.S.C. 154(b) by 889 days.

(21) Appl. No.: 17/791,401

(22) PCT Filed: Jan. 8, 2021

(86) PCT No.: PCT/IB2021/050115
§ 371 (c)(1),
(2) Date: Jul. 7, 2022

(87) PCT Pub. No.: WO2021/140475
PCT Pub. Date: Jul. 15, 2021

(65) Prior Publication Data
US 2023/0054202 A1 Feb. 23, 2023

(30) Foreign Application Priority Data
Jan. 8, 2020 (IN) .............................. 202021000807

(51) Int. Cl.
*C07K 16/18* (2006.01)
*C12N 15/63* (2006.01)
(52) U.S. Cl.
CPC .............. *C07K 16/18* (2013.01); *C12N 15/63* (2013.01); *C07K 2317/24* (2013.01); *C07K 2317/31* (2013.01); *C07K 2317/565* (2013.01); *C07K 2317/732* (2013.01); *C07K 2317/734* (2013.01); *C07K 2317/92* (2013.01)
(58) Field of Classification Search
CPC .............. C07K 16/18; C07K 2317/24; C07K 2317/31; C07K 2317/565; C07K 2317/732; C07K 2317/734; C07K 2317/92; C07K 2317/33; C07K 2317/622; C07K 2317/71; C07K 2317/76; C12N 15/63; A61K 2039/505
See application file for complete search history.

(56) References Cited

FOREIGN PATENT DOCUMENTS

| WO | 2008/118711 | 10/2008 |
| WO | 2009/110918 | 9/2009 |
| WO | 2011/109494 | 9/2011 |
| WO | 2011/112850 | 9/2011 |
| WO | 2013/006449 | 1/2013 |
| WO | 2018/140956 | 8/2018 |

OTHER PUBLICATIONS

Bendig M. M. Methods: A Companion to Methods in Enzymology, 1995; 8:83-93.*
Cuzick et al. The Lancet, vol. 361, p. 296-300, 2003.*
Evans et al. Q. J. Med 1999: 92: 299-307.*
Hernandez-Ledesma et al. Peptides, vol. 30, p. 426-430, 2009 (Year: 2009).*
Houdebine et al., Journal of Biotechnology, vol. 34, p. 269- 287, 1994.*
Houdebine. Comparative Immunology, Microbiology, and Infectious Diseases, vol. 32, p. 107-121, 2009.*
Kappell et al., Current Opinions in Biotechnology, vol. 3, p. 548-553, 1992.*
Komenaka et al., Clinics in Dermatology, 2004, vol. 22, p. 251-265 (Year: 2004).*
Paul, Fundamental Immunology, 3rd Edition, 1993, pp. 6-7 and 292-295 (Year: 1993).*
Rudikoff et al. Proceedings of the National Academy of Sciences USA, vol. 79, p. 1979-1983, 1982.*
Schiffman et al., The New England Journal of Medicine, Vo. 353, No. 20, p. 2101-2104, 2005 (Year: 2005).*
Wall et al., Theriogenology, vol. 45, p. 57-68, 1996.*
MacCallum et al. J. Mol. Biol., 262, 732-745, 1996.*
Pascalis et al. The Journal of Immunology (2002) 169: 3076-3084.*
Vajdos et al. J. Mol. Biol. (2002) 320: 415-428.*
Panka et al. Proc. Nati. Acad. Sci. USA vol. 85, pp. 3080-3084, May 1988.*
International Search Report for PCT/IB2021/050115 dated May 12, 2021 (5 pages).

(Continued)

*Primary Examiner* — Sean E Aeder
*Assistant Examiner* — Yie Chia Lee
(74) *Attorney, Agent, or Firm* — Nixon & Vanderhye, PC

(57) ABSTRACT

The present invention provides an antibody or antigen-binding portion thereof that can bind to properdin (factor P). The antibody of the current invention leads to selective inhibition of alternative complement pathway while allowing the classical and lectin pathways to continue. Further, the antibody of the present invention may have modified or reduced binding to FcγRs to minimize its ADCC activity. The present invention provide an antibody that comprises an amino acid sequence to minimise its CDC activity. The antibody according to the present invention has higher FcRn binding affinity and therefore the antibody according to the present invention may have long circulating half-life in the body of the patient and it can be given at a reduced dosing frequency. The antibody according to the present invention can further be used in the preparation of a drug for treating diseases through inhibition of alternative complement pathway.

15 Claims, 6 Drawing Sheets

Specification includes a Sequence Listing.

(56)  References Cited

OTHER PUBLICATIONS

Written Opinion of the ISA for PCT/IB2021/050115 dated May 12, 2021 (8 pages).

Pauly et al., "A Novel Antibody against Human Properdin Inhibits the Alternative Complement System and Specifically Detects Properdin from Blood Samples", PLOS One; 13 pgs.

Gupta-Bansal et al., "Inhibition of complement alternative pathway function with anti-properdin monoclonal antibodies"; Molecular Immunology 37 (2000); pp. 191-201.

\* cited by examiner

SEQUENCE LISTING

```
<160> NUMBER OF SEQ ID NOS: 98

<210> SEQ ID NO 1
<211> LENGTH: 7
<212> TYPE: PRT
<213> ORGANISM: Artificial Sequence
<220> FEATURE:
<223> OTHER INFORMATION: sequences are synthesized by recombinant method

<400> SEQUENCE: 1

Gly Tyr Thr Phe Thr Asp Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: sequences are synthesized by recombinant method

<400> SEQUENCE: 2

Gly Tyr Thr Phe Ala His Asn
1               5

<210> SEQ ID NO 3
<211> LENGTH: 9
<212> TYPE: PRT
<213> ORGANISM: Artificial Sequence
<220> FEATURE:
<223> OTHER INFORMATION: sequences are synthesized by recombinant method

<400> SEQUENCE: 3

Gly Tyr Ser Ile Thr Ser Gly Tyr Tyr
1               5

<210> SEQ ID NO 4
<211> LENGTH: 9
```

```
<212> TYPE: PRT
<213> ORGANISM: Artificial Sequence
<220> FEATURE:
<223> OTHER INFORMATION: sequences are synthesized by recombinant method

<400> SEQUENCE: 4

Gly Tyr Ser Ile Thr Ser Thr Tyr Tyr
1               5

<210> SEQ ID NO 5
<211> LENGTH: 7
<212> TYPE: PRT
<213> ORGANISM: Artificial Sequence
<220> FEATURE:
<223> OTHER INFORMATION: sequences are synthesized by recombinant method

<400> SEQUENCE: 5

Gly Tyr Ser Phe Thr Ser Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: sequences are synthesized by recombinant method

<400> SEQUENCE: 6

Val Ile Ser Thr Tyr Tyr Gly Asp
1               5

<210> SEQ ID NO 7
<211> LENGTH: 8
<212> TYPE: PRT
<213> ORGANISM: Artificial Sequence
<220> FEATURE:
<223> OTHER INFORMATION: sequences are synthesized by recombinant method

<400> SEQUENCE: 7

Leu Ile Ser Thr Tyr Tyr Gly Asp
1               5

<210> SEQ ID NO 8
<211> LENGTH: 8
<212> TYPE: PRT
<213> ORGANISM: Artificial Sequence
<220> FEATURE:
<223> OTHER INFORMATION: sequences are synthesized by recombinant method

<400> SEQUENCE: 8

Tyr Ile Asn Pro Gly Thr Asp Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: sequences are synthesized by recombinant method

<400> SEQUENCE: 9

Tyr Ile Ser Tyr Asp Gly Gly Asn
1               5

<210> SEQ ID NO 10
<211> LENGTH: 8
<212> TYPE: PRT
```

```
<213> ORGANISM: Artificial Sequence
<220> FEATURE:
<223> OTHER INFORMATION: sequences are synthesized by recombinant method

<400> SEQUENCE: 10

Tyr Ile Ser Tyr Asp Gly Thr Asn
1               5

<210> SEQ ID NO 11
<211> LENGTH: 8
<212> TYPE: PRT
<213> ORGANISM: Artificial Sequence
<220> FEATURE:
<223> OTHER INFORMATION: sequences are synthesized by recombinant method

<400> SEQUENCE: 11

Glu Ile Asp Pro Ser Ala Gly Tyr
1               5

<210> SEQ ID NO 12
<211> LENGTH: 6
<212> TYPE: PRT
<213> ORGANISM: Artificial Sequence
<220> FEATURE:
<223> OTHER INFORMATION: sequences are synthesized by recombinant method

<400> SEQUENCE: 12

Asp Gly Tyr Leu Asp Tyr
1               5

<210> SEQ ID NO 13
<211> LENGTH: 10
<212> TYPE: PRT
<213> ORGANISM: Artificial Sequence
<220> FEATURE:
<223> OTHER INFORMATION: sequences are synthesized by recombinant method

<400> SEQUENCE: 13

Ala Asp Ser Ser Gly Asn Phe Phe Asp Tyr
1               5                   10

<210> SEQ ID NO 14
<211> LENGTH: 14
<212> TYPE: PRT
<213> ORGANISM: Artificial Sequence
<220> FEATURE:
<223> OTHER INFORMATION: sequences are synthesized by recombinant method

<400> SEQUENCE: 14

Arg Lys Leu Tyr Gly Asn Phe Val Asp Tyr Ala Met Asp Tyr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: sequences are synthesized by recombinant method

<400> SEQUENCE: 15

Asp Leu Asp Gly Tyr Glu Ser Met Asp Tyr
1               5                   10

<210> SEQ ID NO 16
<211> LENGTH: 11
<212> TYPE: PRT
<213> ORGANISM: Artificial Sequence
```

<220> FEATURE:
<223> OTHER INFORMATION: sequences are synthesized by recombinant method

<400> SEQUENCE: 16

Asp Asp Tyr Asp Arg Ser Pro Trp Phe Ala Tyr
1               5                   10

<210> SEQ ID NO 17
<211> LENGTH: 8
<212> TYPE: PRT
<213> ORGANISM: Artificial Sequence
<220> FEATURE:
<223> OTHER INFORMATION: sequences are synthesized by recombinant method

<400> SEQUENCE: 17

Glu Gly Tyr Arg Tyr Phe Asp Val
1               5

<210> SEQ ID NO 18
<211> LENGTH: 8
<212> TYPE: PRT
<213> ORGANISM: Artificial Sequence
<220> FEATURE:
<223> OTHER INFORMATION: sequences are synthesized by recombinant method

<400> SEQUENCE: 18

Glu Gly Tyr Lys Tyr Phe Asp Val
1               5

<210> SEQ ID NO 19
<211> LENGTH: 13
<212> TYPE: PRT
<213> ORGANISM: Artificial Sequence
<220> FEATURE:
<223> OTHER INFORMATION: sequences are synthesized by recombinant method

<400> SEQUENCE: 19

Ser Gly Ser Ser Ser Asn Ile Gly Asn Asn Tyr Val Ser
1               5                   10

<210> SEQ ID NO 20
<211> LENGTH: 17
<212> TYPE: PRT
<213> ORGANISM: Artificial Sequence
<220> FEATURE:
<223> OTHER INFORMATION: sequences are synthesized by recombinant method

<400> SEQUENCE: 20

Lys Ser Ser Gln Ser Leu Leu Tyr Ser Ser Asn Gln Lys Asn Tyr Leu
1               5                   10                  15

Ala

<210> SEQ ID NO 21
<211> LENGTH: 11
<212> TYPE: PRT
<213> ORGANISM: Artificial Sequence
<220> FEATURE:
<223> OTHER INFORMATION: sequences are synthesized by recombinant method

<400> SEQUENCE: 21

Arg Pro Ser Gln Asp Ile Asn Asn Tyr Leu Ser
1               5                   10

<210> SEQ ID NO 22
<211> LENGTH: 16
<212> TYPE: PRT

-continued

```
<213> ORGANISM: Artificial Sequence
<220> FEATURE:
<223> OTHER INFORMATION: sequences are synthesized by recombinant method

<400> SEQUENCE: 22

Lys Ser Ser Gln Ser Leu Leu Asp Ile Asn Gly Lys Thr Tyr Leu Asn
1               5                   10                  15

<210> SEQ ID NO 23
<211> LENGTH: 11
<212> TYPE: PRT
<213> ORGANISM: Artificial Sequence
<220> FEATURE:
<223> OTHER INFORMATION: sequences are synthesized by recombinant method

<400> SEQUENCE: 23

Leu Ala Ser Gln Thr Ile Gly Thr Trp Leu Ala
1               5                   10

<210> SEQ ID NO 24
<211> LENGTH: 13
<212> TYPE: PRT
<213> ORGANISM: Artificial Sequence
<220> FEATURE:
<223> OTHER INFORMATION: sequences are synthesized by recombinant method

<400> SEQUENCE: 24

Arg Leu Asp Gly Ser Ser Pro Gly Asn Asn Tyr Val Ser
1               5                   10

<210> SEQ ID NO 25
<211> LENGTH: 13
<212> TYPE: PRT
<213> ORGANISM: Artificial Sequence
<220> FEATURE:
<223> OTHER INFORMATION: sequences are synthesized by recombinant method

<400> SEQUENCE: 25

Ser Gly Ser Ser Ser Asn Ile Arg Gly Thr Pro Thr Thr
1               5                   10

<210> SEQ ID NO 26
<211> LENGTH: 13
<212> TYPE: PRT
<213> ORGANISM: Artificial Sequence
<220> FEATURE:
<223> OTHER INFORMATION: sequences are synthesized by recombinant method

<400> SEQUENCE: 26

Ser Gly Ser Ser Ser Asn Leu Gly Val Lys Asp Val Asn
1               5                   10

<210> SEQ ID NO 27
<211> LENGTH: 13
<212> TYPE: PRT
<213> ORGANISM: Artificial Sequence
<220> FEATURE:
<223> OTHER INFORMATION: sequences are synthesized by recombinant method

<400> SEQUENCE: 27

Tyr Pro Arg Leu Leu Phe Lys Gly Asn Asn Tyr Val Ser
1               5                   10

<210> SEQ ID NO 28
<211> LENGTH: 13
<212> TYPE: PRT
<213> ORGANISM: Artificial Sequence
```

<220> FEATURE:
<223> OTHER INFORMATION: sequences are synthesized by recombinant method

<400> SEQUENCE: 28

Ser Gly Ser Ser Ser Asn His Gln His Arg Pro Ala Ser
1               5                   10

<210> SEQ ID NO 29
<211> LENGTH: 13
<212> TYPE: PRT
<213> ORGANISM: Artificial Sequence
<220> FEATURE:
<223> OTHER INFORMATION: sequences are synthesized by recombinant method

<400> SEQUENCE: 29

Glu Gln Trp Ser Pro Gly His Gly Asn Asn Tyr Val Ser
1               5                   10

<210> SEQ ID NO 30
<211> LENGTH: 7
<212> TYPE: PRT
<213> ORGANISM: Artificial Sequence
<220> FEATURE:
<223> OTHER INFORMATION: sequences are synthesized by recombinant method

<400> SEQUENCE: 30

Asp Asn Asn Lys Arg Phe Ser
1               5

<210> SEQ ID NO 31
<211> LENGTH: 7
<212> TYPE: PRT
<213> ORGANISM: Artificial Sequence
<220> FEATURE:
<223> OTHER INFORMATION: sequences are synthesized by recombinant method

<400> SEQUENCE: 31

Trp Ala Ser Thr Arg Glu Ser
1               5

<210> SEQ ID NO 32
<211> LENGTH: 7
<212> TYPE: PRT
<213> ORGANISM: Artificial Sequence
<220> FEATURE:
<223> OTHER INFORMATION: sequences are synthesized by recombinant method

<400> SEQUENCE: 32

Tyr Thr Ser Arg Leu His Ser
1               5

<210> SEQ ID NO 33
<211> LENGTH: 7
<212> TYPE: PRT
<213> ORGANISM: Artificial Sequence
<220> FEATURE:
<223> OTHER INFORMATION: sequences are synthesized by recombinant method

<400> SEQUENCE: 33

Leu Val Ser Lys Leu Asp Ser
1               5

<210> SEQ ID NO 34
<211> LENGTH: 7
<212> TYPE: PRT
<213> ORGANISM: Artificial Sequence
<220> FEATURE:

<223> OTHER INFORMATION: sequences are synthesized by recombinant method

<400> SEQUENCE: 34

Ala Ala Thr Ser Leu Ala Asp
1               5

<210> SEQ ID NO 35
<211> LENGTH: 11
<212> TYPE: PRT
<213> ORGANISM: Artificial Sequence
<220> FEATURE:
<223> OTHER INFORMATION: sequences are synthesized by recombinant method

<400> SEQUENCE: 35

Gly Ala Trp Asp Gly Ser Leu Arg Glu Ala Val
1               5                   10

<210> SEQ ID NO 36
<211> LENGTH: 10
<212> TYPE: PRT
<213> ORGANISM: Artificial Sequence
<220> FEATURE:
<223> OTHER INFORMATION: sequences are synthesized by recombinant method

<400> SEQUENCE: 36

Gln Gln Tyr Tyr Ser Tyr Pro Tyr Thr Leu
1               5                   10

<210> SEQ ID NO 37
<211> LENGTH: 8
<212> TYPE: PRT
<213> ORGANISM: Artificial Sequence
<220> FEATURE:
<223> OTHER INFORMATION: sequences are synthesized by recombinant method

<400> SEQUENCE: 37

His Gln Tyr Leu Ser Ser Tyr Thr
1               5

<210> SEQ ID NO 38
<211> LENGTH: 9
<212> TYPE: PRT
<213> ORGANISM: Artificial Sequence
<220> FEATURE:
<223> OTHER INFORMATION: sequences are synthesized by recombinant method

<400> SEQUENCE: 38

Gln Gln Gly Asn Thr Leu Pro Pro Thr
1               5

<210> SEQ ID NO 39
<211> LENGTH: 9
<212> TYPE: PRT
<213> ORGANISM: Artificial Sequence
<220> FEATURE:
<223> OTHER INFORMATION: sequences are synthesized by recombinant method

<400> SEQUENCE: 39

Trp Gln Gly Thr His Phe Pro Tyr Thr
1               5

<210> SEQ ID NO 40
<211> LENGTH: 9
<212> TYPE: PRT
<213> ORGANISM: Artificial Sequence
<220> FEATURE:
<223> OTHER INFORMATION: sequences are synthesized by recombinant method

```
<400> SEQUENCE: 40

Gln Gln Leu Tyr Ser Thr Pro Trp Thr
1               5

<210> SEQ ID NO 41
<211> LENGTH: 11
<212> TYPE: PRT
<213> ORGANISM: Artificial Sequence
<220> FEATURE:
<223> OTHER INFORMATION: sequences are synthesized by recombinant method

<400> SEQUENCE: 41

Ala Ala Arg Gln His Leu Leu Arg Glu Ala Val
1               5                   10

<210> SEQ ID NO 42
<211> LENGTH: 11
<212> TYPE: PRT
<213> ORGANISM: Artificial Sequence
<220> FEATURE:
<223> OTHER INFORMATION: sequences are synthesized by recombinant method

<400> SEQUENCE: 42

Gly Ala Trp Asp Ala Ser Leu Arg Glu Ala Val
1               5                   10

<210> SEQ ID NO 43
<211> LENGTH: 11
<212> TYPE: PRT
<213> ORGANISM: Artificial Sequence
<220> FEATURE:
<223> OTHER INFORMATION: sequences are synthesized by recombinant method

<400> SEQUENCE: 43

Met Thr Gln Asn Gly Ile Leu Arg Glu Ala Val
1               5                   10

<210> SEQ ID NO 44
<211> LENGTH: 115
<212> TYPE: PRT
<213> ORGANISM: Artificial Sequence
<220> FEATURE:
<223> OTHER INFORMATION: sequences are synthesized by recombinant method

<400> SEQUENCE: 44

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
                20                  25                  30

Ala Leu His Trp Val Lys Gln Ser His Ala Glu Ser Leu Glu Trp Ile
            35                  40                  45

Gly Val Ile Ser Thr Tyr Tyr Gly Asp Ala Ser Tyr Asn Gln Lys Phe
        50                  55                  60

Lys Asp Lys Ala Thr Met Thr Val Asp Ile Ser Ser Ser Thr Ala Tyr
65                  70                  75                  80

Leu Glu Leu Ala Arg Leu Thr Ser Glu Asp Ser Ala Ile Tyr Tyr Cys
                85                  90                  95

Ala Arg Asp Gly Tyr Leu Asp Tyr Trp Gly Gln Gly Thr Leu Val Thr
            100                 105                 110

Val Ser Ser
        115
```

-continued

<210> SEQ ID NO 45
<211> LENGTH: 119
<212> TYPE: PRT
<213> ORGANISM: Artificial Sequence
<220> FEATURE:
<223> OTHER INFORMATION: sequences are synthesized by recombinant method

<400> SEQUENCE: 45

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Glu Ser Leu Glu Trp Ile
        35                  40                  45

Gly Leu Ile Ser Thr Tyr Tyr Gly Asp Ala Gly Tyr Asn Gln Lys Phe
    50                  55                  60

Lys Asp Lys Ala Thr Met Thr Val Asp Ile Ser Ser Ser Thr Ala Tyr
65                  70                  75                  80

Leu Glu Leu Ala Arg Leu Thr Ser Glu Asp Ser Ala Ile Tyr Tyr Cys
                85                  90                  95

Ala Arg Ala Asp Ser Ser Gly Asn Phe Phe Asp Tyr Trp Gly Gln Gly
            100                 105                 110

Thr Leu Val Thr Val Ser Ser
        115

<210> SEQ ID NO 46
<211> LENGTH: 123
<212> TYPE: PRT
<213> ORGANISM: Artificial Sequence
<220> FEATURE:
<223> OTHER INFORMATION: sequences are synthesized by recombinant method

<400> SEQUENCE: 46

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ala His Asn
            20                  25                  30

Trp Ile His Trp Val Lys Gln Lys Pro Gly Gln Gly Leu Glu Trp Ile
        35                  40                  45

Gly Tyr Ile Asn Pro Gly Thr Asp Tyr Thr Glu Tyr Ser Gln Arg Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Arg Lys Leu Tyr Gly Asn Phe Val Asp Tyr Ala Met Asp Tyr
            100                 105                 110

Trp Gly Gln Gly Thr Leu Val Thr Val Ser Ala
        115                 120

<210> SEQ ID NO 47
<211> LENGTH: 119
<212> TYPE: PRT
<213> ORGANISM: Artificial Sequence
<220> FEATURE:
<223> OTHER INFORMATION: sequences are synthesized by recombinant method

<400> SEQUENCE: 47

Gln Val Gln Leu Gln Glu Ser Gly Pro Gly Leu Val Lys Pro Ser Gln

```
1               5               10              15

Thr Leu Ser Leu Thr Cys Thr Val Ser Gly Tyr Ser Ile Thr Ser Gly
                20              25              30

Tyr Tyr Trp Asn Trp Ile Arg Gln His Pro Gly Lys Gly Leu Glu Trp
            35              40              45

Ile Gly Tyr Ile Ser Tyr Asp Gly Gly Asn Lys Tyr Asn Pro Ser Leu
        50              55              60

Lys Ser Arg Val Thr Ile Ser Arg Asp Thr Ser Lys Asn Gln Phe Ser
65                  70              75                  80

Leu Lys Leu Ser Ser Val Thr Ala Ala Asp Thr Ala Val Tyr Tyr Cys
                85              90              95

Ala Arg Asp Leu Asp Gly Tyr Glu Ser Met Asp Tyr Trp Gly Gln Gly
                100             105             110

Thr Ser Val Thr Val Ser Ser
        115

<210> SEQ ID NO 48
<211> LENGTH: 120
<212> TYPE: PRT
<213> ORGANISM: Artificial Sequence
<220> FEATURE:
<223> OTHER INFORMATION: sequences are synthesized by recombinant method

<400> SEQUENCE: 48

Gln Val Gln Leu Gln Glu Ser Gly Pro Gly Leu Val Lys Pro Ser Gln
1               5               10              15

Thr Leu Ser Leu Thr Cys Thr Val Ser Gly Tyr Ser Ile Thr Ser Thr
                20              25              30

Tyr Tyr Trp Asn Trp Ile Arg Gln His Pro Gly Lys Gly Leu Glu Trp
            35              40              45

Ile Gly Tyr Ile Ser Tyr Asp Gly Thr Asn Lys Tyr Asn Pro Ser Leu
        50              55              60

Lys Ser Arg Val Thr Ile Ser Arg Asp Thr Ser Lys Asn Gln Phe Ser
65                  70              75                  80

Leu Lys Leu Ser Ser Val Thr Ala Ala Asp Thr Ala Val Tyr Tyr Cys
                85              90              95

Ala Arg Asp Asp Tyr Asp Arg Ser Pro Trp Phe Ala Tyr Trp Gly Gln
                100             105             110

Gly Thr Leu Val Thr Val Ser Ser
        115                 120

<210> SEQ ID NO 49
<211> LENGTH: 117
<212> TYPE: PRT
<213> ORGANISM: Artificial Sequence
<220> FEATURE:
<223> OTHER INFORMATION: sequences are synthesized by recombinant method

<400> SEQUENCE: 49

Gln Val Gln Leu Gln Gln Pro Gly Ala Glu Leu Val Lys Pro Gly Ala
1               5               10              15

Ser Val Ile Leu Ser Cys Lys Ala Ser Gly Tyr Ser Phe Thr Ser Tyr
                20              25              30

Trp Val His Trp Val Lys Gln Arg Pro Gly Gln Gly Leu Glu Trp Ile
            35              40              45

Gly Glu Ile Asp Pro Ser Ala Gly Tyr Thr Asn Phe Asn Gln Lys Phe
        50              55              60
```

Arg Asp Met Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Glu Gly Tyr Arg Tyr Phe Asp Val Trp Gly Ala Gly Thr Thr
                100                 105                 110

Val Thr Val Ser Ser
        115

<210> SEQ ID NO 50
<211> LENGTH: 115
<212> TYPE: PRT
<213> ORGANISM: Artificial Sequence
<220> FEATURE:
<223> OTHER INFORMATION: sequences are synthesized by recombinant method

<400> SEQUENCE: 50

Gln Val Gln Leu Lys Glu Ser Gly Ala Glu Leu Val Arg Pro Gly Val
1                   5                   10                  15

Ser Val Lys Ile Ser Cys Lys Gly Ser Gly Tyr Thr Phe Thr Asp Tyr
                20                  25                  30

Ala Met His Trp Val Lys Gln Ser His Ala Lys Ser Leu Glu Trp Ile
            35                  40                  45

Gly Val Ile Ser Thr Tyr Tyr Gly Asp Ala Ser Tyr Asn Gln Lys Phe
        50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Asp Gly Tyr Leu Asp Tyr Trp Gly Gln Gly Thr Thr Leu Thr
                100                 105                 110

Val Ser Ser
        115

<210> SEQ ID NO 51
<211> LENGTH: 120
<212> TYPE: PRT
<213> ORGANISM: Artificial Sequence
<220> FEATURE:
<223> OTHER INFORMATION: sequences are synthesized by recombinant method

<400> SEQUENCE: 51

Gly Ala Glu Leu Val Arg Pro Gly Val Ser Val Lys Ile Ser Cys Lys
1                   5                   10                  15

Gly Ser Gly Tyr Thr Phe Thr Asp Tyr Ala Met His Trp Val Lys Gln
                20                  25                  30

Ser His Ala Lys Ser Leu Glu Trp Ile Gly Leu Ile Ser Thr Tyr Tyr
            35                  40                  45

Gly Asp Ala Arg Tyr Asn Gln Lys Phe Arg Gly Lys Ala Thr Met Thr
        50                  55                  60

Val Asp Lys Ser Ser Ser Thr Ala Tyr Met Glu Leu Ala Arg Leu Thr
65                  70                  75                  80

Ser Glu Asp Ser Ala Ile Tyr Tyr Cys Ala Arg Ala Asp Ser Ser Gly
                85                  90                  95

Asn Phe Phe Asp Tyr Trp Gly Gln Gly Thr Thr Leu Thr Val Ser Ser
                100                 105                 110

Ala Lys Thr Thr Pro Pro Ser Val
        115                 120

```
<210> SEQ ID NO 52
<211> LENGTH: 128
<212> TYPE: PRT
<213> ORGANISM: Artificial Sequence
<220> FEATURE:
<223> OTHER INFORMATION: sequences are synthesized by recombinant method

<400> SEQUENCE: 52

Gly Ala Glu Leu Ala Lys Pro Gly Ala Ser Val Lys Met Ser Cys Lys
1               5                   10                  15

Ala Ser Gly Tyr Thr Phe Ala His Asn Trp Met His Trp Val Lys Gln
                20                  25                  30

Arg Pro Gly Gln Gly Leu Glu Trp Ile Gly Tyr Ile Asn Pro Gly Thr
        35                  40                  45

Asp Tyr Thr Glu Tyr Ser Gln Arg Phe Lys Asp Lys Ala Thr Leu Thr
    50                  55                  60

Ala Asp Lys Ser Ser Ser Thr Ala Tyr Met Gln Leu Ser Ser Leu Thr
65                  70                  75                  80

Ser Glu Asp Ser Ala Val Tyr Tyr Cys Ala Arg Arg Lys Leu Tyr Gly
                85                  90                  95

Asn Phe Val Asp Tyr Ala Met Asp Tyr Trp Gly Gln Gly Thr Ser Val
                100                 105                 110

Thr Val Ser Ser Ala Lys Thr Thr Pro Pro Ser Val Tyr Pro Leu Ala
        115                 120                 125

<210> SEQ ID NO 53
<211> LENGTH: 124
<212> TYPE: PRT
<213> ORGANISM: Artificial Sequence
<220> FEATURE:
<223> OTHER INFORMATION: sequences are synthesized by recombinant method

<400> SEQUENCE: 53

Gly Pro Gly Leu Val Lys Pro Ser Gln Ser Leu Ser Leu Thr Cys Ser
1               5                   10                  15

Val Thr Gly Tyr Ser Ile Thr Ser Gly Tyr Tyr Trp Asn Trp Ile Arg
                20                  25                  30

Gln Phe Pro Gly Asn Lys Leu Glu Trp Met Gly Tyr Ile Ser Tyr Asp
        35                  40                  45

Gly Gly Asn Ile Tyr Asn Pro Ser Leu Lys Asn Arg Ile Ser Ile Thr
    50                  55                  60

Arg Asp Thr Ser Lys Asn Gln Phe Phe Leu Lys Leu Asn Ser Val Thr
65                  70                  75                  80

Ser Glu Asp Thr Ala Thr Tyr Tyr Cys Ala Arg Asp Leu Asp Gly Tyr
                85                  90                  95

Glu Ser Met Asp Tyr Trp Gly Gln Gly Thr Ser Val Thr Val Ser Ser
                100                 105                 110

Ala Lys Thr Thr Pro Pro Ser Val Tyr Pro Leu Ala
        115                 120

<210> SEQ ID NO 54
<211> LENGTH: 116
<212> TYPE: PRT
<213> ORGANISM: Artificial Sequence
<220> FEATURE:
<223> OTHER INFORMATION: sequences are synthesized by recombinant method

<400> SEQUENCE: 54
```

```
Lys Pro Ser Gln Ser Leu Ser Leu Thr Cys Ser Val Thr Gly Tyr Ser
1               5                   10                  15

Ile Thr Ser Thr Tyr Tyr Trp Asn Trp Ile Arg Gln Phe Pro Gly Asn
            20                  25                  30

Lys Leu Glu Trp Met Gly Tyr Ile Ser Tyr Asp Gly Thr Asn Lys Tyr
        35                  40                  45

Asn Pro Ser Leu Lys Asn Arg Ile Ser Ile Thr Arg Asp Thr Ser Lys
        50                  55                  60

Asn Arg Phe Phe Leu Lys Leu Asn Ser Val Thr Thr Glu Asp Thr Ala
65                  70                  75                  80

Thr Tyr Tyr Cys Ala Gly Asp Asp Tyr Asp Arg Ser Pro Trp Phe Ala
                85                  90                  95

Tyr Trp Gly Gln Gly Thr Leu Val Thr Val Ser Ala Ala Lys Thr Thr
            100                 105                 110

Pro Pro Ser Val
        115

<210> SEQ ID NO 55
<211> LENGTH: 117
<212> TYPE: PRT
<213> ORGANISM: Artificial Sequence
<220> FEATURE:
<223> OTHER INFORMATION: sequences are synthesized by recombinant method

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Arg Gln Ala Pro Gly Gln Gly Leu Glu Trp Met
        35                  40                  45

Gly Glu Ile Asp Pro Ser Ala Gly Tyr Thr Asn Tyr Asn Gln Lys Phe
        50                  55                  60

Thr Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Glu Gly Tyr Lys Tyr Phe Asp Val Trp Gly Ala Gly Thr Thr
            100                 105                 110

Val Thr Val Ser Ser
        115

<210> SEQ ID NO 56
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 56

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Val Gln Leu Pro Gly Thr Ala Pro Lys Leu Leu
        35                  40                  45

Ile Tyr Asp Asn Asn Lys Arg Phe Ser Gly Val Pro Asp Arg Phe Ser
        50                  55                  60
```

```
Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ala Trp Asp Gly Ser Leu
                85                  90                  95

Arg Glu Ala Val Phe Gly Gly Gly Thr Lys Val Thr Val Leu Arg
            100                 105                 110
```

<210> SEQ ID NO 57
<211> LENGTH: 113
<212> TYPE: PRT
<213> ORGANISM: Artificial Sequence
<220> FEATURE:
<223> OTHER INFORMATION: sequences are synthesized by recombinant method

<400> SEQUENCE: 57

```
Asp Ile Val Met Thr Gln Ser Pro Asp Ser Leu Ala Val Ser Leu Gly
1                   5                   10                  15

Glu Arg Ala Thr Ile Asn Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys
```

<210> SEQ ID NO 58
<211> LENGTH: 113
<212> TYPE: PRT
<213> ORGANISM: Artificial Sequence
<220> FEATURE:
<223> OTHER INFORMATION: sequences are synthesized by recombinant method

<400> SEQUENCE: 58

```
Asp Ile Val Met Thr Gln Ser Pro Asp Ser Leu Ala Val Ser Leu Gly
1                   5                   10                  15

Glu Arg Ala Thr Ile Asn Cys Lys Ser Ser Gln Ser Val Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Ser Ser Tyr Thr Phe Gly Gln Gly Thr Lys Val Glu Ile Lys
            100                 105                 110

Arg
```

<210> SEQ ID NO 59
<211> LENGTH: 108

```
<212> TYPE: PRT
<213> ORGANISM: Artificial Sequence
<220> FEATURE:
<223> OTHER INFORMATION: sequences are synthesized by recombinant method

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asp Ile Asn Asn Tyr
            20                  25                  30

Leu Ser Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gln Gly Thr Lys Val Glu Ile Lys Arg
            100                 105

<210> SEQ ID NO 60
<211> LENGTH: 113
<212> TYPE: PRT
<213> ORGANISM: Artificial Sequence
<220> FEATURE:
<223> OTHER INFORMATION: sequences are synthesized by recombinant method

<400> SEQUENCE: 60

Asp Ile Val Met Thr Gln Ser Pro Leu Ser Leu Ser Val Thr Pro Gly
1               5                   10                  15

Gln Pro Ala Ser Ile Ser Cys Lys Ser Ser Gln Ser Leu Leu Asp Ile
            20                  25                  30

Asn Gly Lys Thr Tyr Leu Asn Trp Tyr Leu Gln Lys Pro Gly Gln Ser
        35                  40                  45

Pro Gln Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Val Glu Ile Lys
            100                 105                 110

Arg

<210> SEQ ID NO 61
<211> LENGTH: 108
<212> TYPE: PRT
<213> ORGANISM: Artificial Sequence
<220> FEATURE:
<223> OTHER INFORMATION: sequences are synthesized by recombinant method

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Ala Trp Tyr Gln Gln Lys Pro Gly Lys Ala Pro Lys Leu Leu Ile
        35                  40                  45
```

-continued

```
Tyr Ala Ala Thr Ser Leu Ala Asp Gly Val Pro Ser Arg Phe Ser Gly
    50              55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Leu Tyr Ser Thr Pro Trp
                85                  90                  95

Thr Phe Gly Gly Gly Thr Lys Leu Glu Ile Lys Arg
            100             105
```

```
<210> SEQ ID NO 62
<211> LENGTH: 127
<212> TYPE: PRT
<213> ORGANISM: Artificial Sequence
<220> FEATURE:
<223> OTHER INFORMATION: sequences are synthesized by recombinant method

<400> SEQUENCE: 62

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Val Gln Leu Pro Gly Thr Ala Pro Lys Leu Leu
            35                  40                  45

Ile Tyr Asp Asn Asn Lys Arg Phe Ser Gly Val Pro Asp Arg Phe Ser
    50              55                  60

Gly Ser Lys Ser Gly Thr Ser Ala Thr Leu Gly Ile Thr Gly Leu Gln
65              70                  75                  80

Thr Gly Asp Glu Ala Asp Tyr Tyr Cys Gly Ala Trp Asp Gly Ser Leu
                85                  90                  95

Arg Glu Ala Val Phe Gly Gly Gly Thr Lys Val Thr Val Leu Val Arg
                100             105                 110

Pro Leu Asp Pro Lys Ile Ser Glu Leu Lys Leu Leu Lys Val Val
        115             120                 125
```

```
<210> SEQ ID NO 63
<211> LENGTH: 94
<212> TYPE: PRT
<213> ORGANISM: Artificial Sequence
<220> FEATURE:
<223> OTHER INFORMATION: sequences are synthesized by recombinant method

<400> SEQUENCE: 63

Ser Ser Leu Ala Val Ser Ala Gly Glu Lys Val Thr Met Ser Cys Lys
1               5                   10                  15

Ser Ser Gln Ser Val Leu Tyr Ser Ser Asn Gln Lys Asn Tyr Leu Ala
                20                  25                  30

Trp Tyr Gln Gln Lys Pro Gly Gln Ser Pro Lys Leu Leu Ile Tyr Trp
            35                  40                  45

Ala Ser Thr Arg Glu Ser Gly Val Pro Asp Arg Phe Thr Gly Ser Gly
    50              55                  60

Ser Gly Thr Asp Phe Thr Leu Thr Ile Ser Ser Val Gln Ala Glu Asp
65              70                  75                  80

Leu Ala Val Tyr Tyr Cys His Gln Tyr Leu Ser Ser Tyr Thr
                85                  90
```

```
<210> SEQ ID NO 64
<211> LENGTH: 97
<212> TYPE: PRT
```

-continued

```
<213> ORGANISM: Artificial Sequence
<220> FEATURE:
<223> OTHER INFORMATION: sequences are synthesized by recombinant method

<400> SEQUENCE: 64

Pro Ser Ser Leu Ala Val Ser Val Gly Glu Lys Val Thr Leu Asn Cys
1               5                   10                  15

Lys Ser Ser Gln Ser Leu Leu Tyr Ser Ser Asn Gln Lys Asn Tyr Leu
                20                  25                  30

Ala Trp Tyr Gln Gln Lys Pro Gly Gln Ser Pro Lys Leu Leu Ile Asn
        35                  40                  45

Trp Ala Ser Thr Arg Glu Ser Gly Val Pro Asp Arg Cys Thr Gly Ser
    50                  55                  60

Gly Ser Gly Thr Asp Phe Thr Leu Thr Ile Ser Asn Val Lys Ala Glu
65                  70                  75                  80

Asp Leu Ala Val Tyr Tyr Cys Gln Gln Tyr Tyr Ser Tyr Pro Tyr Thr
                85                  90                  95

Leu

<210> SEQ ID NO 65
<211> LENGTH: 94
<212> TYPE: PRT
<213> ORGANISM: Artificial Sequence
<220> FEATURE:
<223> OTHER INFORMATION: sequences are synthesized by recombinant method

<400> SEQUENCE: 65

Leu Thr Leu Ser Val Thr Phe Gly Gln Pro Ala Ser Ile Ser Cys Lys
1               5                   10                  15

Ser Ser Gln Ser Leu Leu Asp Ile Asn Gly Lys Thr Tyr Leu Asn Trp
                20                  25                  30

Leu Leu Gln Arg Pro Gly Gln Ser Pro Lys Arg Leu Ile Tyr Leu Val
        35                  40                  45

Ser Lys Leu Asp Ser Gly Val Pro Asp Arg Phe Thr Gly Ser Gly Ser
    50                  55                  60

Gly Thr Asp Phe Thr Leu Lys Ile Ser Arg Val Glu Ala Glu Asp Leu
65                  70                  75                  80

Gly Ile Tyr Tyr Cys Trp Gln Gly Thr His Phe Pro Tyr Thr
                85                  90

<210> SEQ ID NO 66
<211> LENGTH: 108
<212> TYPE: PRT
<213> ORGANISM: Artificial Sequence
<220> FEATURE:
<223> OTHER INFORMATION: sequences are synthesized by recombinant method

<400> SEQUENCE: 66

Asp Ile Val Leu Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
                20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80
```

```
Glu Asp Phe Val Ser Tyr Tyr Cys Gln Gln Leu Tyr Ser Thr Pro Trp
                85                  90                  95

Thr Phe Gly Gly Gly Thr Lys Leu Glu Ile Lys Arg
            100                 105

<210> SEQ ID NO 67
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 67

Gln Ser Val Leu Thr Gln Pro Pro Ser Val Ser Ala Ala Pro Gly Gln
1               5                   10                  15

Lys Val Thr Ile Ser Cys Arg Leu Asp Gly Ser Ser Pro Gly Asn Asn
            20                  25                  30

Tyr Val Ser Trp Tyr Val Gln Leu Pro Gly Thr Ala Pro Lys Leu Leu
        35                  40                  45

Ile Tyr Asp Asn Asn Lys Arg Phe Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Ala Arg Gln His Leu Leu
                85                  90                  95

Arg Glu Ala Val Phe Gly Gly Gly Thr Lys Val Thr Val Leu Arg
            100                 105                 110

<210> SEQ ID NO 68
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 68

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Arg Gly Thr
            20                  25                  30

Pro Thr Thr Trp Tyr Val Gln Leu Pro Gly Thr Ala Pro Lys Leu Leu
        35                  40                  45

Ile Tyr Asp Asn Asn Lys Arg Phe Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ala Trp Asp Gly Ser Leu
                85                  90                  95

Arg Glu Ala Val Phe Gly Gly Gly Thr Lys Val Thr Val Leu Arg
            100                 105                 110

<210> SEQ ID NO 69
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 69

Gln Ser Val Leu Thr Gln Pro Pro Ser Val Ser Ala Ala Pro Gly Gln
```

-continued

```
1                  5                   10                   15

Lys Val Thr Ile Ser Cys Ser Gly Ser Ser Ser Asn Leu Gly Val Lys
                 20                   25                   30

Asp Val Asn Trp Tyr Val Gln Leu Pro Gly Thr Ala Pro Lys Leu Leu
                 35                   40                   45

Ile Tyr Asp Asn Asn Lys Arg Phe Ser Gly Val Pro Asp Arg Phe Ser
                 50                   55                   60

Gly Ser Lys Ser Gly Thr Ser Ala Thr Leu Gly Ile Thr Gly Leu Gln
65                   70                   75                   80

Thr Gly Asp Glu Ala Asp Tyr Tyr Cys Gly Ala Trp Asp Ala Ser Leu
                 85                   90                   95

Arg Glu Ala Val Phe Gly Gly Gly Thr Lys Val Thr Val Leu Arg
                 100                  105                  110

<210> SEQ ID NO 70
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 70

Gln Ser Val Leu Thr Gln Pro Pro Ser Val Ser Ala Ala Pro Gly Gln
1                  5                   10                   15

Lys Val Thr Ile Ser Cys Tyr Pro Arg Leu Leu Phe Lys Gly Asn Asn
                 20                   25                   30

Tyr Val Ser Trp Tyr Val Gln Leu Pro Gly Thr Ala Pro Lys Leu Leu
                 35                   40                   45

Ile Tyr Asp Asn Asn Lys Arg Phe Ser Gly Val Pro Asp Arg Phe Ser
                 50                   55                   60

Gly Ser Lys Ser Gly Thr Ser Ala Thr Leu Gly Ile Thr Gly Leu Gln
65                   70                   75                   80

Thr Gly Asp Glu Ala Asp Tyr Tyr Cys Gly Ala Trp Asp Gly Ser Leu
                 85                   90                   95

Arg Glu Ala Val Phe Gly Gly Gly Thr Lys Val Thr Val Leu Arg
                 100                  105                  110

<210> SEQ ID NO 71
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 71

Gln Ser Val Leu Thr Gln Pro Pro Ser Val Ser Ala Ala Pro Gly Gln
1                  5                   10                   15

Lys Val Thr Ile Ser Cys Ser Gly Ser Ser Ser Asn His Gln His Arg
                 20                   25                   30

Pro Ala Ser Trp Tyr Val Gln Leu Pro Gly Thr Ala Pro Lys Leu Leu
                 35                   40                   45

Ile Tyr Asp Asn Asn Lys Arg Phe Ser Gly Val Pro Asp Arg Phe Ser
                 50                   55                   60

Gly Ser Lys Ser Gly Thr Ser Ala Thr Leu Gly Ile Thr Gly Leu Gln
65                   70                   75                   80

Thr Gly Asp Glu Ala Asp Tyr Tyr Cys Met Thr Gln Asn Gly Ile Leu
                 85                   90                   95
```

```
Arg Glu Ala Val Phe Gly Gly Gly Thr Lys Val Thr Val Leu Arg
        100                 105                 110

<210> SEQ ID NO 72
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 72

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Val Gln Leu Pro Gly Thr Ala Pro Lys Leu Leu
        35                  40                  45

Ile Tyr Asp Asn Asn Lys Arg Phe Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Met Thr Gln Asn Gly Ile Leu
                85                  90                  95

Arg Glu Ala Val Phe Gly Gly Gly Thr Lys Val Thr Val Leu Arg
            100                 105                 110

<210> SEQ ID NO 73
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 73

Gln Ser Val Leu Thr Gln Pro Pro Ser Val Ser Ala Ala Pro Gly Gln
1               5                   10                  15

Lys Val Thr Ile Ser Cys Arg Leu Asp Gly Ser Ser Pro Gly Asn Asn
            20                  25                  30

Tyr Val Ser Trp Tyr Val Gln Leu Pro Gly Thr Ala Pro Lys Leu Leu
        35                  40                  45

Ile Tyr Asp Asn Asn Lys Arg Phe Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Met Thr Gln Asn Gly Ile Leu
                85                  90                  95

Arg Glu Ala Val Phe Gly Gly Gly Thr Lys Val Thr Val Leu Arg
            100                 105                 110

<210> SEQ ID NO 74
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 74

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Arg Gly Thr
```

-continued

```
            20              25              30

Pro Thr Thr Trp Tyr Val Gln Leu Pro Gly Thr Ala Pro Lys Leu Leu
        35              40              45

Ile Tyr Asp Asn Asn Lys Arg Phe Ser Gly Val Pro Asp Arg Phe Ser
    50              55              60

Gly Ser Lys Ser Gly Thr Ser Ala Thr Leu Gly Ile Thr Gly Leu Gln
65              70              75              80

Thr Gly Asp Glu Ala Asp Tyr Tyr Cys Met Thr Gln Asn Gly Ile Leu
            85              90              95

Arg Glu Ala Val Phe Gly Gly Gly Thr Lys Val Thr Val Leu Arg
            100             105             110
```

<210> SEQ ID NO 75
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 75

```
Gln Ser Val Leu Thr Gln Pro Pro Ser Val Ser Ala Ala Pro Gly Gln
1               5               10              15

Lys Val Thr Ile Ser Cys Ser Gly Ser Ser Ser Asn Leu Gly Val Lys
            20              25              30

Asp Val Asn Trp Tyr Val Gln Leu Pro Gly Thr Ala Pro Lys Leu Leu
        35              40              45

Ile Tyr Asp Asn Asn Lys Arg Phe Ser Gly Val Pro Asp Arg Phe Ser
    50              55              60

Gly Ser Lys Ser Gly Thr Ser Ala Thr Leu Gly Ile Thr Gly Leu Gln
65              70              75              80

Thr Gly Asp Glu Ala Asp Tyr Tyr Cys Met Thr Gln Asn Gly Ile Leu
            85              90              95

Arg Glu Ala Val Phe Gly Gly Gly Thr Lys Val Thr Val Leu Arg
            100             105             110
```

<210> SEQ ID NO 76
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 76

```
Gln Ser Val Leu Thr Gln Pro Pro Ser Val Ser Ala Ala Pro Gly Gln
1               5               10              15

Lys Val Thr Ile Ser Cys Tyr Pro Arg Leu Leu Phe Lys Gly Asn Asn
            20              25              30

Tyr Val Ser Trp Tyr Val Gln Leu Pro Gly Thr Ala Pro Lys Leu Leu
        35              40              45

Ile Tyr Asp Asn Asn Lys Arg Phe Ser Gly Val Pro Asp Arg Phe Ser
    50              55              60

Gly Ser Lys Ser Gly Thr Ser Ala Thr Leu Gly Ile Thr Gly Leu Gln
65              70              75              80

Thr Gly Asp Glu Ala Asp Tyr Tyr Cys Met Thr Gln Asn Gly Ile Leu
            85              90              95

Arg Glu Ala Val Phe Gly Gly Gly Thr Lys Val Thr Val Leu Arg
            100             105             110
```

<210> SEQ ID NO 77
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 77

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Val Gln Leu Pro Gly Thr Ala Pro Lys Leu Leu
        35                  40                  45

Ile Tyr Asp Asn Asn Lys Arg Phe Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Ala Arg Gln His Leu Leu
                85                  90                  95

Arg Glu Ala Val Phe Gly Gly Gly Thr Lys Val Thr Val Leu Arg
            100                 105                 110

<210> SEQ ID NO 78
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 78

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Arg Gly Thr
            20                  25                  30

Pro Thr Thr Trp Tyr Val Gln Leu Pro Gly Thr Ala Pro Lys Leu Leu
        35                  40                  45

Ile Tyr Asp Asn Asn Lys Arg Phe Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Ala Arg Gln His Leu Leu
                85                  90                  95

Arg Glu Ala Val Phe Gly Gly Gly Thr Lys Val Thr Val Leu Arg
            100                 105                 110

<210> SEQ ID NO 79
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 79

Gln Ser Val Leu Thr Gln Pro Pro Ser Val Ser Ala Ala Pro Gly Gln
1               5                   10                  15

Lys Val Thr Ile Ser Cys Glu Gln Trp Ser Pro Gly His Gly Asn Asn
            20                  25                  30

Tyr Val Ser Trp Tyr Val Gln Leu Pro Gly Thr Ala Pro Lys Leu Leu

-continued

```
            35                  40                  45
Ile Tyr Asp Asn Asn Lys Arg Phe Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Ala Arg Gln His Leu Leu
                85                  90                  95

Arg Glu Ala Val Phe Gly Gly Gly Thr Lys Val Thr Val Leu Arg
                100                 105                 110
```

<210> SEQ ID NO 80
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 80

```
Gln Ser Val Leu Thr Gln Pro Pro Ser Val Ser Ala Ala Pro Gly Gln
1                   5                   10                  15

Lys Val Thr Ile Ser Cys Tyr Pro Arg Leu Leu Phe Lys Gly Asn Asn
                20                  25                  30

Tyr Val Ser Trp Tyr Val Gln Leu Pro Gly Thr Ala Pro Lys Leu Leu
            35                  40                  45

Ile Tyr Asp Asn Asn Lys Arg Phe Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Ala Arg Gln His Leu Leu
                85                  90                  95

Arg Glu Ala Val Phe Gly Gly Gly Thr Lys Val Thr Val Leu Arg
                100                 105                 110
```

<210> SEQ ID NO 81
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 81

```
Gln Ser Val Leu Thr Gln Pro Pro Ser Val Ser Ala Ala Pro Gly Gln
1                   5                   10                  15

Lys Val Thr Ile Ser Cys Ser Gly Ser Ser Ser Asn His Gln His Arg
                20                  25                  30

Pro Ala Ser Trp Tyr Val Gln Leu Pro Gly Thr Ala Pro Lys Leu Leu
            35                  40                  45

Ile Tyr Asp Asn Asn Lys Arg Phe Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Ala Ala Arg Gln His Leu Leu
                85                  90                  95

Arg Glu Ala Val Phe Gly Gly Gly Thr Lys Val Thr Val Leu Arg
                100                 105                 110
```

<210> SEQ ID NO 82
<211> LENGTH: 111

-continued

```
<212> TYPE: PRT
<213> ORGANISM: Artificial Sequence
<220> FEATURE:
<223> OTHER INFORMATION: sequences are synthesized by recombinant method

<400> SEQUENCE: 82

Gln Ser Val Leu Thr Gln Pro Pro Ser Val Ser Ala Ala Pro Gly Gln
1               5                   10                  15

Lys Val Thr Ile Ser Cys Arg Leu Asp Gly Ser Ser Pro Gly Asn Asn
                20                  25                  30

Tyr Val Ser Trp Tyr Val Gln Leu Pro Gly Thr Ala Pro Lys Leu Leu
            35                  40                  45

Ile Tyr Asp Asn Asn Lys Arg Phe Ser Gly Val Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ala Trp Asp Gly Ser Leu
                85                  90                  95

Arg Glu Ala Val Phe Gly Gly Gly Thr Lys Val Thr Val Leu Arg
                100                 105                 110

<210> SEQ ID NO 83
<211> LENGTH: 111
<212> TYPE: PRT
<213> ORGANISM: Artificial Sequence
<220> FEATURE:
<223> OTHER INFORMATION: sequences are synthesized by recombinant method

<400> SEQUENCE: 83

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn His Gln His Arg
                20                  25                  30

Pro Ala Ser Trp Tyr Val Gln Leu Pro Gly Thr Ala Pro Lys Leu Leu
            35                  40                  45

Ile Tyr Asp Asn Asn Lys Arg Phe Ser Gly Val Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ala Trp Asp Gly Ser Leu
                85                  90                  95

Arg Glu Ala Val Phe Gly Gly Gly Thr Lys Val Thr Val Leu Arg
                100                 105                 110

<210> SEQ ID NO 84
<211> LENGTH: 723
<212> TYPE: DNA
<213> ORGANISM: Artificial Sequence
<220> FEATURE:
<223> OTHER INFORMATION: sequences are synthesized by recombinant method

<400> SEQUENCE: 84
atgggctggt cctgcatcat tctgtttctg gtggctaccg ccaccggcgt gcactctgat      60
atcgtgatga cccagtctcc tgacagcctg gctgtgtctc tgggcgagag agccaccatc     120
aactgcaagt cctctcagtc cctgctgtac tcctccaacc agaagaacta cctggcctgg     180
tatcagcaga agcccggaca gcctcctaag ctgctgatct actgggcctc caccagagaa     240
tctggcgtgc cagatagatt ctccggctct ggctctggca ccgactttac cctgacaatc     300
```

-continued

```
agctctctgc aggccgagga tgtggccgtg tactactgcc agcagtacta cagctacccc    360
tacacctttg gcggaggcac caagctggaa atcaagagaa ccgtggccgc tccttccgtg    420
ttcatcttcc caccatctga cgagcagctg aagtccggca cagcttctgt cgtgtgcctg    480
ctgaacaact ctaccctcg ggaagccaag gtgcagtgga aggtggacaa tgccctgcag    540
tccggcaact cccaagagtc tgtgaccgag caggactcca aggactctac ctacagcctg    600
tcctccacac tgaccctgtc taaggccgac tacgagaagc acaaggtgta cgcctgtgaa    660
gtgacccacc agggactgtc tagccccgtg accaagtctt tcaacagagg cgagtgctaa    720
tga                                                                   723

<210> SEQ ID NO 85
<211> LENGTH: 720
<212> TYPE: DNA
<213> ORGANISM: Artificial Sequence
<220> FEATURE:
<223> OTHER INFORMATION: sequences are synthesized by recombinant method

<400> SEQUENCE: 85
atgggctggt cctgcatcat tctgtttctg gtggctaccg ccaccggcgt gcactctgat     60
atcgtgatga cccagtctcc tctgagcctg tctgtgacac ctggccagcc tgcctccatc    120
tcttgcaagt catctcagtc cctgctggac atcaacggca agacctacct gaactggtat    180
ctgcagaagc ccggccagtc tccacagctg ctgatctacc tggtgtccaa gctggattct    240
ggcgtgcccg acagattttc cggctctggc tctggcaccg acttcaccct gaagatttcc    300
agagtggaag ccgaggacgt gggcgtgtac tactgttggc agggcaccca ctttccatac    360
accttcggcc agggcaccaa ggtggaaatc aagagaaccg tggccgctcc ttccgtgttc    420
atcttcccac atctgacga gcagctgaag tccggcacag cttctgtcgt gtgcctgctg    480
aacaacttct accctcggga gccaaggtg cagtggaagg tggacaatgc cctgcagtcc    540
ggcaactccc aagagtctgt gaccgagcag gactccaagg actctaccta ctctctgtcc    600
tccacactga ccctgtccaa ggccgactac gagaagcaca aggtgtacgc ctgtgaagtg    660
acccaccagg gactgtctag ccccgtgacc aagtctttca acagaggcga gtgctaatga    720

<210> SEQ ID NO 86
<211> LENGTH: 705
<212> TYPE: DNA
<213> ORGANISM: Artificial Sequence
<220> FEATURE:
<223> OTHER INFORMATION: sequences are synthesized by recombinant method

<400> SEQUENCE: 86
atgggctggt cctgcatcat tctgtttctg gtggctaccg ccaccggcgt gcactctgat     60
atccagatga cccagtctcc ttccagcctg tctgcctctg tgggcgacag agtgaccatc    120
acctgtctgg cttctcagac catcggcacc tggctggcct ggtatcagca gaagcctgga    180
aaggccccta agctgctgat ctacgctgcc acatctctgg ccgatggcgt gccatctaga    240
ttctctggct ctggctccgg caccgacttt accctgacaa tcagttccct gcagcctgag    300
gacttcgcca cctactactg ccagcagctg tactctaccc cttggacctt ggcggaggc    360 accaagctgg aaatcaagag aaccgtggcc gctccttccg tgttcatctt cccaccatct    420
gacgagcagc tgaagtctgg caccgcttct gtcgtgtgcc tgctgaacaa cttctaccct    480
cgggaagcca aggtgcagtg gaaggtggac aatgccctgc agtccggcaa ctcccaagag    540
tctgtgaccg agcaggactc caaggactct acctacagcc tgtcctccac actgaccctg    600
```

```
tctaaggccg actacgagaa gcacaaggtg tacgcctgtg aagtgaccca ccagggactg      660
tctagccccg tgaccaagtc tttcaacaga ggcgagtgct aatga                     705

<210> SEQ ID NO 87
<211> LENGTH: 720
<212> TYPE: DNA
<213> ORGANISM: Artificial Sequence
<220> FEATURE:
<223> OTHER INFORMATION: sequences are synthesized by recombinant method

<400> SEQUENCE: 87
atgggctggt cctgcatcat tctgtttctg gtggctaccg ccaccggcgt gcactctcag       60 tctgtttttga ctcagcctcc ttccgtgtct gccgctcctg gccagaaagt gaccatctct      120
tgctccggct cctcctccaa catcggcaac aactatgtgt cttggtacgt gcagctgccc      180
ggcacagctc ctaagctgct gatctacgac aacaacaagc ggttctccgg cgtgcccgac      240
agattctctg gctctaagtc tggcaccagc gctaccctgg gaatcacagg attgcagaca      300
ggcgacgagg ccgattacta ctgtggcgct tgggacggct ctctgaggga agctgttttt      360
ggcggaggca ccaaagtgac cgtgctgaga gctgctggac agcctaaagc cgctcctagc      420
gtgaccctgt ttcctccatc ttctgaggaa ctgcaggcca acaaggctac cctcgtgtgc      480
ctgatctctg acttttaccc tggcgctgtg accgtggcct ggaaggctga tagttctcct      540
gtgaaggccg gcgtggaaac caccacacct tccaagcagt ccaacaacaa atacgccgcc      600
tcctcctacc tgtctctgac ccctgaacag tggaagtccc accggtccta ctcttgccaa      660
gtgacccatg agggctccac cgtggaaaag acagtggccc ctaccgagtg ctcctaatga      720

<210> SEQ ID NO 88
<211> LENGTH: 431
<212> TYPE: DNA
<213> ORGANISM: Artificial Sequence
<220> FEATURE:
<223> OTHER INFORMATION: sequences are synthesized by recombinant method

<400> SEQUENCE: 88
atgggctggt cctgcatcat tctgtttctg gtggctaccg ccaccggcgt gcactctcag       60
gttcagttgc aacagtctgg ccctgaactc gtcagacccg gcgtgtccgt gaagatcagc      120
tgtaaaggct ccggctacac cttcaccgac tacgccatgc actgggtcaa gcagtctcac      180
gccgagtctc tggaatggat cggcctgatc tctacctact acggcgacgc cggctacaac      240
cagaagttca aggataaggc cacaatgacc gtggacatct cctcctccac cgcctacctg      300
gaactggcta gactgaccctc tgaggactcc gccatctact actgcgccag agccgactcc      360
tctggcaact ctttgatta ctggggccag ggcaccctgg tcaccgtttc tagtgcttcc      420
acaaagggcc c                                                           431

<210> SEQ ID NO 89
<211> LENGTH: 443
<212> TYPE: DNA
<213> ORGANISM: Artificial Sequence
<220> FEATURE:
<223> OTHER INFORMATION: sequences are synthesized by recombinant method

<400> SEQUENCE: 89
atgggctggt cctgcatcat tctgtttctg gtggctaccg ccaccggcgt gcactctgaa       60
gttcagttgc agcagtctgg ccccgagctt gtgaaacctg gcgcctctgt gaagatgtcc      120
```

```
tgcaaggcct ctggctacac cttcgctcac aactggattc actgggtcaa gcagaagcca      180
ggccagggac ttgagtggat cggctacatc aaccctggca ccgactacac cgagtactcc      240
cagagattca agggcaaagc taccctgacc tccgacaagt cctcctccac cgcttacatg      300
gaactgtcca gcctgacctc tgaggactcc gccgtgtact actgcgccag aagaaagctg      360
tacggcaact tcgtggacta cgccatggat tattgggggcc agggcaccct ggttaccgtg      420
tctgctgctt ctacaaaggg ccc                                               443
```

<210> SEQ ID NO 90
<211> LENGTH: 431
<212> TYPE: DNA
<213> ORGANISM: Artificial Sequence
<220> FEATURE:
<223> OTHER INFORMATION: sequences are synthesized by recombinant method

<400> SEQUENCE: 90

```
atgggctggt cctgcatcat tctgtttctg gtggctaccg ccaccggcgt gcactctcag       60
gttcagttgc aagagtctgg ccctggcctg gtcaagcctt ctcagaccct gtctctgacc      120
tgcaccgtgt ccggctattc catcacctcc ggctactact ggaactggat cagacagcac      180
cccggcaaag gcctggaatg gatcggctac atctcttacg acggcggcaa caagtacaac      240
cccagcctga gtccagagt gaccatctct cgggacacct ccaagaacca gttctccctg      300
aagctgtcct ctgtgaccgc tgccgatacc gccgtgtact actgtgcccg cgatctggat      360
ggctacgagt ctatggatta ttggggccag ggcacctccg tgaccgtgtc ctctgcttct      420
acaaagggcc c                                                           431
```

<210> SEQ ID NO 91
<211> LENGTH: 434
<212> TYPE: DNA
<213> ORGANISM: Artificial Sequence
<220> FEATURE:
<223> OTHER INFORMATION: sequences are synthesized by recombinant method

<400> SEQUENCE: 91

```
atgggctggt cctgcatcat tctgtttctg gtggctaccg ccaccggcgt gcactctcag       60
gttcagttgc aagagtctgg ccctggcctg gtcaagcctt ctcagaccct gtctctgacc      120
tgcaccgtgt ccggctactc catcacctcc acctactact ggaactggat cagacagcac      180
cccggcaaag gcctggaatg gatcggctac atctcctacg acggcaccaa caagtacaac      240
cccagcctga gtccagagt gaccatctct cgggacacct ccaagaacca gttctccctg      300
aagctgtcct ctgtgaccgc tgccgatacc gccgtgtact actgcgccag agatgactac      360
gacagatccc cttggtttgc ctattggggc agggcacac tggtcaccgt ttccagtgct      420
tctaccaagg gccc                                                         434
```

<210> SEQ ID NO 92
<211> LENGTH: 419
<212> TYPE: DNA
<213> ORGANISM: Artificial Sequence
<220> FEATURE:
<223> OTHER INFORMATION: sequences are synthesized by recombinant method

<400> SEQUENCE: 92

```
atgggctggt cctgcatcat tctgtttctg gtggctaccg ccaccggcgt gcactctcag       60
gttcagttgc aacagtctgg ccctgaactc gtcagaccg gcgtgtccgt gaagatcagc      120
tgtaaaggct ccggctacac cttcaccgat tacgccctgc actgggtcaa gcagtctcac      180
```

-continued

```
gctgagtctc tggaatggat cggcgtgatc tccacctact acggcgacgc ctcctacaac    240
cagaagttca aggacaaggc cacaatgacc gtggacatct cctcctccac cgcctacctg    300
gaactggcta gactgacctc tgaggactcc gccatctact actgcgccag agatggctac    360
ctggattatt ggggccaggg cacactggtc accgtgtcct ctgcttctac aaagggccc    419

<210> SEQ ID NO 93
<211> LENGTH: 976
<212> TYPE: DNA
<213> ORGANISM: Artificial Sequence
<220> FEATURE:
<223> OTHER INFORMATION: sequences are synthesized by recombinant method

<400> SEQUENCE: 93
gggcccctcc gtgttccctc tggccccttg ctcccggtcc acctccgagt ctaccgccgc     60
tctgggctgc ctggtgaaag actacttccc cgagcccgtg accgtgtcct ggaactctgg    120
cgccctgacc agcggcgtgc acaccttccc tgccgtgctg cagtcctccg gcctgtactc    180
cctgtcctcc gtggtgaccg tgccctcctc cagcctgggc accaagacct acacctgtaa    240
cgtggaccac aagccctcca acaccaaggt ggacaagcgg gtggaatcta agtacggccc    300
tccctgcccc ccctgccctg cccctgaatt ctgggcgga ccttccgtgt tcctgttccc    360
cccaaagccc aaggacaccc tgatgatctc ccggaccccc gaagtgacct gcgtggtggt    420
ggacgtgtcc caggaagatc ccgaggtgca gttcaattgg tacgtggacg gcgtggaagt    480
gcacaacgcc aagaccaagc ccagagagga acagttcaac tccacctacc gggtggtgtc    540
tgtgctgacc gtgctgcacc aggactggct gaacggcaaa gagtacaagt gcaaggtgtc    600
caacaagggc ctgccctcca gcatcgaaaa gaccatctcc aaggccaagg gccagccccg    660
cgagccccag gtgtacaccc tgccccctag ccaggaagag atgaccaaga accaggtgtc    720
cctgacctgt ctggtgaaag gcttctaccc ctccgatatc gccgtggaat gggagtccaa    780
cggccagccc gagaacaact acaagaccac cccccctgtg ctggactccg acggctcctt    840
cttcctgtac tctcggctga ccgtggacaa gtcccggtgg caggaaggca acgtgttctc    900
ctgctccgtg atgcacgagg ccctgcacaa ccactacacc cagaagtccc tgtccctgag    960
cctgggcaag tgatga                                                    976

<210> SEQ ID NO 94
<211> LENGTH: 976
<212> TYPE: DNA
<213> ORGANISM: Artificial Sequence
<220> FEATURE:
<223> OTHER INFORMATION: sequences are synthesized by recombinant method

<400> SEQUENCE: 94
gggcccctcc gtgttccctc tggccccttg ctcccggtcc acctccgagt ctaccgccgc     60
tctgggctgc ctggtgaaag actacttccc cgagcccgtg accgtgtcct ggaactctgg    120
cgccctgacc agcggcgtgc acaccttccc tgccgtgctg cagtcctccg gcctgtactc    180
cctgtcctcc gtggtgaccg tgccctcctc cagcctgggc accaagacct acacctgtaa    240
cgtggaccac aagccctcca acaccaaggt ggacaagcgg gtggaatcta agtacggccc    300
tccctgcccc ccctgccctg cccctgaatt ctgggcgga ccttccgtgt tcctgttccc    360
cccaaagccc aaggacaccc tgatgatctc ccggaccccc gaagtgacct gcgtggtggt    420
ggacgtgtcc caggaagatc ccgaggtgca gttcaattgg tacgtggacg gcgtggaagt    480
```

-continued

```
gcacaacgcc aagaccaagc ctagagagga acagttcaac agcacctaca gagtggtgtc      540
cgtgctgacc gtgctgcacc aggattggct gaacggcaaa gagtacaagt gcaaggtgtc      600
caacaagggc ctgggctcca gcatcgaaaa gaccatctcc aaggctaagg gccagcctcg      660
ggaacctcag gtttacaccc tgcctccaag ccaagaggaa atgaccaaga atcaggtgtc      720
cctgacctgt ctcgtgaagg gcttctaccc ttctgatatc gccgtggaat gggagtccaa      780
cggccagcct gagaacaact acaagaccac acctccagtg ctggactccg acggctcttt      840
cttcctgtat tcccgcctga ccgtggacaa gtccagatgg caagagggca cgtgttctc      900 ctgcagcgtg ctgcatgagg ctctgcactc ccactacacc cagaagtctc tgtctctgtc      960
cctgggcaag tgataa                                                      976
```

<210> SEQ ID NO 95
<211> LENGTH: 327
<212> TYPE: PRT
<213> ORGANISM: Artificial Sequence
<220> FEATURE:
<223> OTHER INFORMATION: sequences are synthesized by recombinant method

<400> SEQUENCE: 95

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
        275             280             285

Arg Leu Thr Val Asp Lys Ser Arg Trp Gln Glu Gly Asn Val Phe Ser
    290             295             300

Cys Ser Val Met His Glu Ala Leu His Asn His Tyr Thr Gln Lys Ser
305             310             315             320

Leu Ser Leu Ser Leu Gly Lys
            325
```

<210> SEQ ID NO 96
<211> LENGTH: 327
<212> TYPE: PRT
<213> ORGANISM: Artificial Sequence
<220> FEATURE:
<223> OTHER INFORMATION: sequences are synthesized by recombinant method

<400> SEQUENCE: 96

```
Ala Ser Thr Lys Gly Pro Ser Val Phe Pro Leu Ala Pro Cys Ser Arg
1               5               10              15

Ser Thr Ser Glu Ser Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Lys Thr
65              70              75              80

Tyr Thr Cys Asn Val Asp His Lys Pro Ser Asn Thr Lys Val Asp Lys
            85              90              95

Arg Val Glu Ser Lys Tyr Gly Pro Pro Cys Pro Pro Cys Pro Ala Pro
            100             105             110

Glu Phe Leu Gly Gly Pro Ser Val Phe Leu Phe Pro Pro Lys Pro Lys
        115             120             125

Asp Thr Leu Met Ile Ser Arg Thr Pro Glu Val Thr Cys Val Val Val
        130             135             140

Asp Val Ser Gln Glu Asp Pro Glu Val Gln Phe Asn Trp Tyr Val Asp
145             150             155             160

Gly Val Glu Val His Asn Ala Lys Thr Lys Pro Arg Glu Glu Gln Phe
            165             170             175

Asn Ser Thr Tyr Arg Val Val Ser Val Leu Thr Val Leu His Gln Asp
            180             185             190

Trp Leu Asn Gly Lys Glu Tyr Lys Cys Lys Val Ser Asn Lys Gly Leu
        195             200             205

Gly Ser Ser Ile Glu Lys Thr Ile Ser Lys Ala Lys Gly Gln Pro Arg
    210             215             220

Glu Pro Gln Val Tyr Thr Leu Pro Pro Ser Gln Glu Glu Met Thr Lys
225             230             235             240

Asn Gln Val Ser Leu Thr Cys Leu Val Lys Gly Phe Tyr Pro Ser Asp
            245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
        275             280             285

Arg Leu Thr Val Asp Lys Ser Arg Trp Gln Glu Gly Asn Val Phe Ser
    290             295             300
```

-continued

```
Cys Ser Val Leu His Glu Ala Leu His Ser His Tyr Thr Gln Lys Ser
305                 310                 315                 320

Leu Ser Leu Ser Leu Gly Lys
                325

<210> SEQ ID NO 97
<211> LENGTH: 17
<212> TYPE: PRT
<213> ORGANISM: Artificial Sequence
<220> FEATURE:
<223> OTHER INFORMATION: sequences are synthesized by recombinant method

<400> SEQUENCE: 97

Lys Ser Ser Gln Ser Val Leu Tyr Ser Ser Asn Gln Lys Asn Tyr Leu
1               5                   10                  15

Ala

<210> SEQ ID NO 98
<211> LENGTH: 9
<212> TYPE: PRT
<213> ORGANISM: Artificial Sequence
<220> FEATURE:
<223> OTHER INFORMATION: sequences are synthesized by recombinant method

<400> SEQUENCE: 98

Gln Gln Tyr Tyr Ser Tyr Pro Tyr Thr
1               5
```

ANTI-PROPERDIN ANTIBODIES AND PREPARATION THEREOF

CROSS-REFERENCE TO RELATED APPLICATIONS

This application is the U.S. national phase of International Application No. PCT/IB2021/050115 filed Jan. 8, 2021, which designated the U.S. and claims priority to IN 202021000807 filed Jan. 8, 2020, the entire contents of each of which are hereby incorporated by reference.

REFERENCE TO SEQUENCE LISTING SUBMITTED ELECTRONICALLY

The content of the electronically submitted sequence listing (Name: 40620267 Sequence_Listing.txt; Size: 71,652 bytes; and Date of Creation: Sep. 8, 2025) is incorporated herein by reference in its entirety.

FIELD OF THE INVENTION

The present invention relates to an antibody or antigen-binding portion thereof that can bind to properdin (factor P). The antibody according to the present invention is further used in the preparation of a drug for treating diseases through inhibition of alternative complement pathway.

BACKGROUND OF THE INVENTION

Scientists have strived for decades to develop drugs to treat complement-mediated diseases. By the end of the 20$^{th}$ century, many anti-complement agents had shown promise in vitro and in animal models, but few drug candidates had progressed to humans and those that did were not developed further. Among the preclinical molecules being tested at that time were antibodies against complement components which blocked their function. For example, the blockade of function of C5 using the anti-mouse C5 and anti-human C5 monoclonal antibodies, was readily established using both, in vitro and in vivo animal disease models. By the early 21$^{st}$ century the humanised anti-human C5 monoclonal antibody, eculizumab, was progressing through clinical development and, in 2007, it was approved by the FDA for use in the rare but devastating disease, paroxysmal nocturnal haemoglobin-uria (PNH). This clinical validation of anti-complement therapy was a landmark in complement drug discovery; this breakthrough, combined with ground-breaking data emerging from genome wide association studies (GWAS), which demonstrated key roles of complement in wide-spread disease, drove a renaissance in anti-complement drug discovery. This has brought us to the current day with many new drugs in this area that are progressing through late stage clinical development and numerous others in discovery or preclinical stages. (1)

However, high expectations raised by a drug candidate developed for ocular indications (i.e., the Factor D (FD)-targeting mAb, lampalizumab) failed to translate into meaningful clinical responses in phase III trials, indicating that individual challenges related to drug bioavailability or efficacy remain to be addressed. The recent FDA approval of a long-acting version of eculizumab (ALXN1210/ravuli-zumab, Ultomiris, Alexion), which features an extended plasma residence and only requires administration every 8 weeks instead of biweekly, is an important step in improving patient management but cannot be considered a bona fide new drug entry in the field. With the current clinical availability of only a single complement specific drug, which evidently cannot cater for all complement-associated clinical indications, the need for disease-tailored therapeutic approaches is becoming ever more urgent. (2)

However, it is to be noted that, the development of drugs targeting complement pathway is associated with a number of challenges, including the sheer number of proteins that one has to choose from, the quantity of circulating or membrane bound proteins of each such target, the natural central role of complement in fighting infection and the safety impact of regulating it too strongly, and the identification of an appropriate disease, or drug indication. In a number of diseases, complement plays a driving role in pathogenesis, whereas in others, complement is an 'exacerbator' of disease, inducing increased pathology initiated by a different disease trigger, thus driving inflammation and tissue damage.

Nevertheless, the number of potential drugs in the complement system is expanding as the role of complement beyond lysis and in cross-talk with other biological systems, such as coagulation, is becoming clearer. There are drugs in development which target each of the three pathways in the complement system and these drugs include small molecules, peptides, biologics, antibodies and DNA-based therapeutics.

Due to the cascade nature of complement pathway and the large number of proteins—both soluble and membrane bound—that it is comprising of, selecting distinct points of intervention may result in different therapeutic effects. In most cases of trigger, the complement pathway is activated by foreign or altered surfaces. In the classical pathway, recognition of immune complexes (and other non-immunoglobulin moieties) by C1q activates the associated serine proteases, C1r and C1s, which cleave the plasma proteins C2 and C4 to form a C3 convertase complex (C4b2a) on the activating surface. The same result is achieved when pattern recognition proteins of the lectin pathway (mannose-binding lectin [MBL], ficolins, collectins) bind to carbohydrate patterns on the pathogen surface and induce MBL-associated serine proteases to cleave C2/C4. The alternative pathway, through an interplay with the proteases, factor B and D (FB, FD), and surface-bound C3b, forms another type of C3 convertase. In all three complement pathways, the point of convergence is the generation of one or the other C3 convertases that activate C3, resulting in at least two significant events on the affected cell surface. One is the deposition of C3b on the target surface (making it a candidate for opsonisation by macrophages) and the simultaneous release of anaphylatoxin, C3a. The other is the formation of C3bBb (C3 convertase) and its stabilization by properdin for the assembly of C5 convertases, which cleave C5. The alternative pathway is the only pathway that remains constitutively active providing a constant minimal background activity ready to amplify with the availability of the right trigger. Whereas the released anaphylatoxin, C5a, is amongst the strongest chemoattractants and pro-inflammatory modulators, working primarily via binding to C5a receptor 1 (C5aR1), the C5b fragment can induce the assembly of membrane attack complex (MAC) that damage or induce lysis of the attacked cells. (1)

More than 20, therapeutic agents targeting distinct components and effector pathways of the complement cascade are now in clinical development for various indications. (2)

The amplification loop of the alternative pathway is a major driving force behind complement activation and often determines the onset of C5 convertase formation, thereby initiating subsequent C5 cleavage and terminal pathway activation. Even in diseases where pathological mechanisms are mediated by the lectin or classical pathways, blockade of the alternative pathway may provide therapeutic benefit due to the reduction of the effect generated through the amplification loop. Therefore, a designed specific intervention of only the amplification loop is considered an attractive proposition in drug development as this would allow the lectin and classical pathways to remain at least partly functional to fight infections; while the blocking of the alternative pathway would control collateral damage to normal tissue.

Within the amplification loop there are multiple druggable targets, e.g., C3 (or C3b), FB, FD and FP (properdin), and all have been targeted in drug development. (1) Despite the progression of drug leads to late-stage clinical development, even more than a decade after the launch of eculizumab, the complement drug market still lacks any new approved therapeutics directed against alternate targets in the cascade. Emerging cases of insufficient response to anti-C5 therapy and the appreciation that multiple triggers and complex genetic traits may convolute a patient's basal complement activity in yet-poorly defined ways, point to the need for more comprehensive patient stratification and robust monitoring during anti-complement treatment of the diseases currently treated with eculizumab.

Though the approval of eculizumab drastically changed the landscape of PNH by introducing the first aetiological therapy for these patients, unmet clinical needs have emerged, including the genetically driven refractory phenotype to anti-C5 in certain patients, the residual haemolysis of C3-opsonized PNH cells in extravascular compartments, and the pharmacokinetic/Pharmacodynamics (PK/PD) breakthrough haemolysis observed in certain cases that evoke strong complement activation (that is, acute infections), irrespective of drug dosing levels. (2).

It is important to note that anti-C5 therapy is associated with the risk of life-threatening and fatal meningococcal infections which may become rapidly life-threatening or fatal if not recognized and treated early. (3)

It is therefore quite conceivable that in most of the complement mediated disease situations a complete inhibition of MAC formation originating from all complement pathways is not essential, and turning down, rather than turning off, complement is likely to be sufficient to confer therapeutic effect while permitting sufficient portion of complement activity remaining to protect from critical infections. The aim of such treatments would be to reverse dysregulation and restore homeostasis. In this context, the amplification loop represents an excellent target. Reducing cycling through the amplification loop by increasing loop regulation or reducing availability of convertase could enable fine-tuning of therapy to ameliorate pathology while retaining the protective roles of complement in immune defence. This will be a significant advantage for treating elderly and infection-vulnerable individuals in the community. Several AP-specific drugs are in phase 2 development, including inhibitors of FB and FD. Other drugs which have modulatory properties are on the horizon; delivery of functional domains of regulators such as FH can directly modulate the convertase enzymes, as in the preclinical molecule AMY201 (Amyndas), a truncated, recombinant form of FH engineered to bind with superior efficacy to target surfaces. Finally, it may be possible to block natural modifiers of complement; properdin stabilises the AP convertase enzymes and MASP3 activates FD, interference at these levels using drugs such as CLG561 (anti-properdin, Novartis) or OMS906 (preclinical anti-MASP3, Omeros) may nudge the complement system towards restored homeostasis. (4)

The present invention is related to antibodies targeting properdin (factor P) to inhibit alternative pathway.

Monoclonal antibodies to properdin are known in the art and have been described, for example, in WO 2006131874, WO 2009110918, WO 201109494, WO 2013006449 and WO 2018140956. Various antibodies have been developed which bind activated properdin, but to the best of our knowledge, none has been approved yet. There is one antibody CLG561 targeting properdin, which is in early clinical stage where it has been evaluated in combination with an anti-C5 antibody. (5)

Thus, there is still an unmet need to effectively regulate properdin activity and thus control alternative complement pathway. Therefore, present invention provides an anti-properdin antibody which can be developed to treat related diseases.

SUMMARY OF THE INVENTION

The present invention provides an antibody or antigen-binding portion thereof that can bind to properdin (factor P). The antibody of the current invention leads to selective inhibition of alternative complement pathway while allowing the classical and lectin pathways to continue. Further, the antibody of the present invention may have modified or reduced binding to FcγRs to minimize its ADCC activity. The present invention provide an antibody that comprises an amino acid sequence to minimise its CDC activity. The antibody according to the present invention has higher FcRn binding affinity and therefore the antibody according to the present invention may have long circulating half-life in the body of the patient and it can be given at a reduced dosing frequency. The antibody according to the present invention can further be used in the preparation of a drug for treating diseases through inhibition of alternative complement pathway.

5 serum (NHS) at both concentrations tested. All tested mAbs showed significant inhibition of MAC formation.

Figure 5:
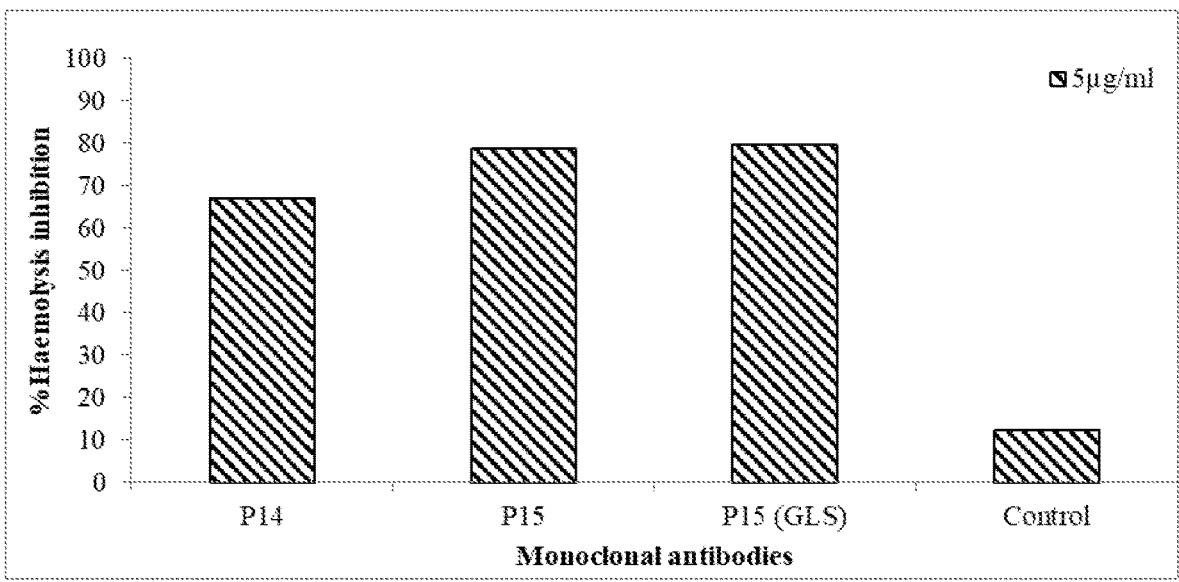

FIG. 5 demonstrates the inhibition of human serum induced haemolysis of self-RBCs caused by CD55 and CD59 dysfunction using the anti-properdin mAbs of the current invention. Human RBCs are generally not lysed in the presence of autologous human serum. However, in the presence of anti-CD55 and anti-CD59 antibodies, the regulation of the complement pathway is disrupted leading to the haemolysis of self-RBCs by autologous serum. The said lysis was inhibited by each of the tested anti-properdin mAbs.

Figure 6:
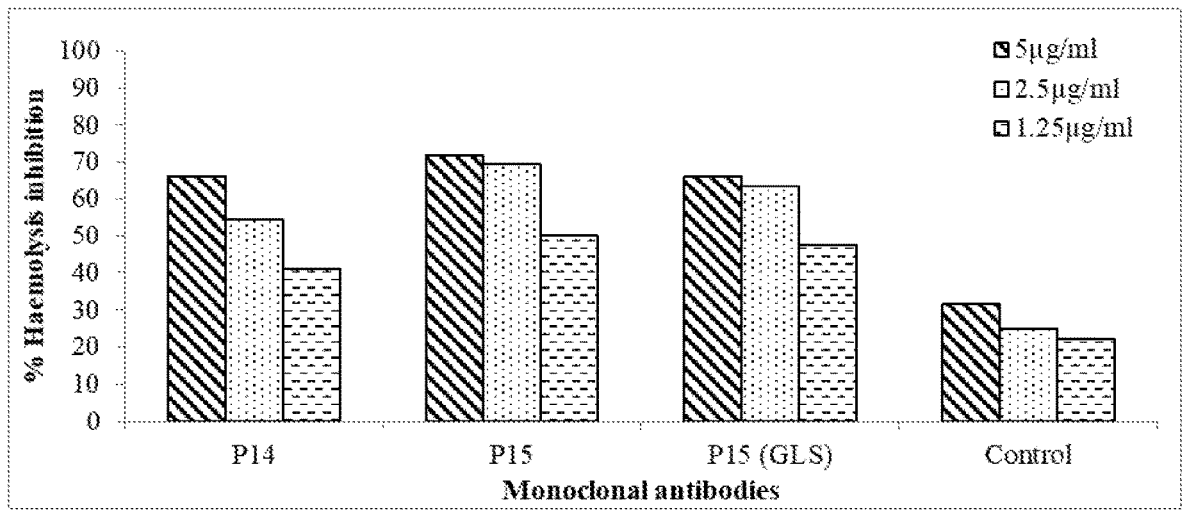

FIG. 6 demonstrates the inhibition of human serum induced haemolysis of pronase treated self-RBC by all the tested anti properdin mAbs of the current invention.

Figure 7:
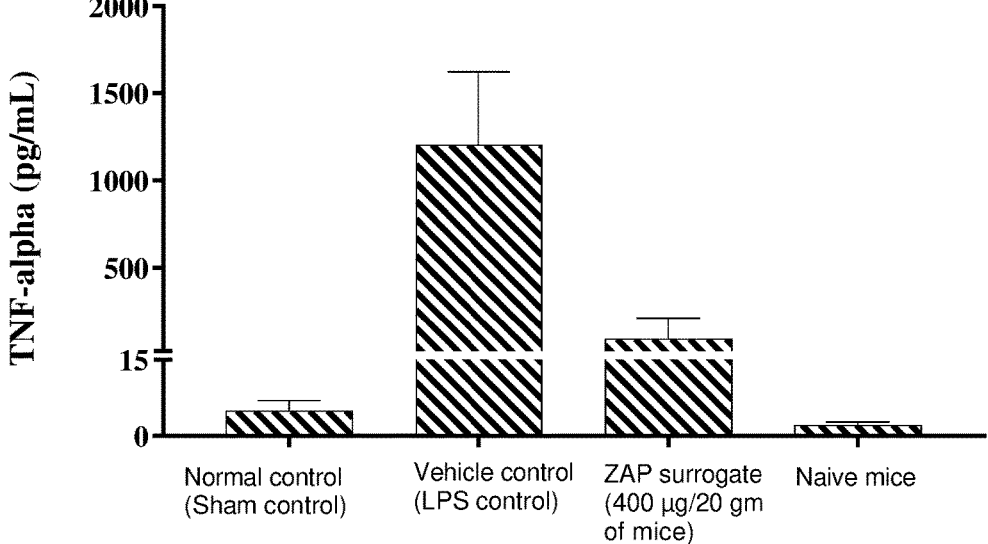

FIG. 7 demonstrates the decrease of intratracheal LPS instillation induced TNF-α production in mice by rabbit anti-mouse properdin mAb (surrogate antibody of the anti-properdin antibody of the current invention).

Figure 8:
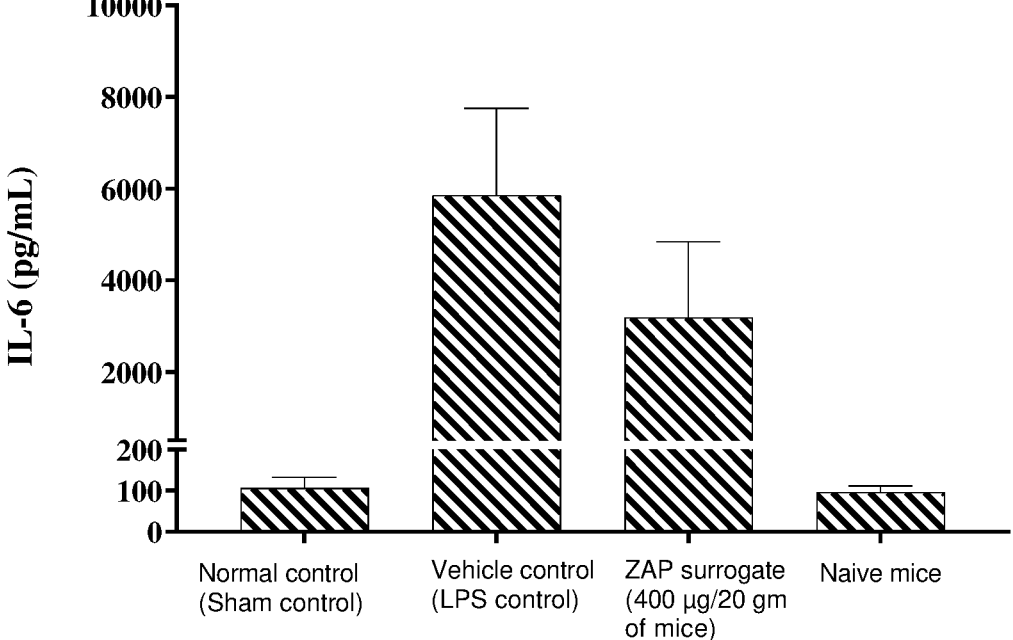

FIG. 8 demonstrates the decrease of intratracheal LPS instillation induced IL-6 production in mice by rabbit anti-mouse properdin mAb (surrogate antibody of the anti-properdin antibody of the current invention).

DEFINITIONS

The term "antibody" as referred to herein includes whole antibodies and any antigen-binding fragments (i.e., "antigen-binding portion") or single chains thereof. An "antibody" refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hyper variability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells such as, NK cells, T cells, macrophages and dendritic cells etc.) and the first component (C1q) of the classical complement system.

The term "operatively linked" is intended to mean that an antibody gene is ligated into a vector such that transcriptional and translational control sequences within the vector serve their intended function of regulating the transcription and translation of the antibody gene.

The term "$K_a$" is the association rate of a particular antibody-antigen interaction, whereas the term "$K_d$" is the dissociation rate of a particular antibody-antigen interaction. The term "$K_D$" is an affinity rate constant, which is obtained from the ratio of $K_d$ to $K_a$. It can be measured by using surface plasma resonance method which is well known in the art.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "bispecific antibody" refers to a homogeneous antibody population involved in the highly specific recognition and binding of two different antigenic determinants, or epitopes.

The term "recombinant antibody", as used herein, includes all antibodies that are prepared, expressed, created or isolated by recombinant means. In certain embodiments, however, such recombinant antibodies can be obtained by in vitro mutagenesis and thus the amino acid sequences of the $V_H$ and $V_L$ regions of the recombinant antibodies as described herein are sequences that may not naturally exist within the human antibody germline repertoire in vivo.

The term "human antibody" includes antibodies having variable and constant regions (if present) derived from human immunoglobulin sequences, preferably human germline sequences.

The term "chimeric antibody and antigen-binding fragments thereof", as used herein comprises portions from two or more different species (e.g., mouse and human). Chimeric antibodies can be produced with mouse variable regions of desired specificity fused to human constant domains (for example, as described in U.S. Pat. No. 4,816,567). In this manner, non-human antibodies can be modified to make them more suitable for human clinical application (e.g., methods for treating or preventing a complement-mediated disorder in a subject).

The term "humanized" as used herein, forms of non-human (for example, murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

The term "pharmaceutical formulation" refers to preparations, which are in such form as to permit the biological activity of the active ingredients to be unequivocally effective. The term "pharmaceutical formulation" or "pharmaceutical composition" or "composition" can be used here interchangeably.

The term "excipient" refers to an agent that may be added to a formulation to stabilize the active drug substance in the formulated form to adjust and maintain osmolality and pH of the pharmaceutical preparations. Examples of commonly used excipients include, but are not limited to, sugars, polyols, amino acids, surfactants, and polymers. "Pharmaceutically acceptable" excipients are those which can reasonably be administered to a subject mammal to provide an effective dose of the active ingredient employed.

The term "treatment" or "therapeutics" as used herein, refers to any treatment of a disease in a mammal, particularly in a human. It includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The terms "patient" and "subject" are used interchangeably and are used in their conventional sense to refer to a living organism suffering from or prone to a condition that can be prevented or treated by administration of a composition of the present invention, and includes both humans and non-human animals. Examples of subjects include, but are not limited to, humans, chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, adult, juvenile and new born individuals are of interest.

TABLE 1

| Abbreviations of amino acid as used in the current application | | |
| --- | --- | --- |
| Full Name | Abbreviation (3 Letter) | Abbreviation (1 Letter) |
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Other Abbreviations Used in the Current Patent Application

ADCC: Antibody-dependent cellular cytotoxicity
aHUS: atypicai hemoiytic uremic syndrome
CDC: Complement-dependent cytotoxicity
CDR: Complementarity determining region CH: Constant region of heavy chain
CL: Constant region of light chain
DEPC: diethyl pyro carbonate
EDTA: Ethylene diamine tetra acetic acid
EGTA: Ethylene glycol-bis(β-aminoethyl ether)-N,N,N', N'-tetra acetic acid
FcRn: Neonatal Fc receptor
FR: Framework region
HCVR: Heavy chain variable region HC: Heavy chain
IPTG: Isopropyl β-D-1-thiogalactopyranoside
i.v.: Intravenous
$K_a$: Association constant
$K_d$: Dissociation constant
$K_D$: Equilibrium dissociation constant
LCVR: Light chain variable region
LC: Light chain
LPS: Lipopolysaccharide
mAb: Monoclonal antibody
MAC: Membrane attack complex
NHS: Normal human serum
OD: Optical density
P20: Polysorbate 20
PBS: Phosphate buffer saline
PF buffer: Periplasmic fraction buffer
Pfx: Proof reading DNA polymerase, Pfx™ from Invitrogen
PNH: Paroxysmal nocturnal hemoglobinuria
RBC: Red blood cell
RPM: Revolutions per minute
RPMI: Roswell park memorial institute
sc: Subcutaneous
scFv: Single chain fragment variable
SEQ/seq: Sequence
SPR: Surface plasmon resonance
TMA: Thrombotic micro angiopathy
TMB: 3, 3', 5, 5'-Tetramethylbenzidin
$V_H$: Variable region of heavy chain
$V_L$: Variable region of light chain

EMBODIMENTS OF THE INVENTION

The disclosure of the present invention relates to novel anti-properdin antibodies that can be used for therapeutic purposes.

In one embodiment, the anti-properdin antibody or antigen binding portion thereof of the present invention binds with high affinity to human properdin.

In one embodiment, the current invention provides an anti-properdin antibody or antigen binding portion thereof comprising:

(a) CDRH1 of the general formula (I): G-Y-$X_{1a}$-$X_{2a}$-$X_{3a}$-$X_{4a}$-$X_{5a}$-$X_{6a}$-$X_{7a}$;

(b) CDRH2 of the general formula (II): $X_{1b}$-I-$X_{2b}$-$X_{3b}$-$X_{4b}$-$X_{5b}$-$X_{6b}$-$X_{7b}$;

(c) CDRH3 of the general formula (III): $X_{1c}$-$X_{2c}$-$X_{3c}$-$X_{4c}$-$X_{5c}$-$X_{6c}$-$X_{7c}$-$X_{8c}$-$X_{9c}$-$X_{10c}$-$X_{11c}$-$X_{12c}$-$X_{13c}$-$X_{14c}$;

(d) CDRL1 of the general formula (IV): $X_{1d}$-$X_{2d}$-$X_{3d}$-$X_{4d}$-$X_{5d}$-$X_{6d}$-$X_{7d}$-$X_{8d}$-$X_{9d}$-$X_{10d}$-$X_{11d}$-$X_{12d}$-$X_{13d}$-$X_{14d}$-$X_{15d}$-$X_{16d}$-$X_{17d}$;

(e) CDRL2 of the general formula (V): $X_{1e}$-$X_{2e}$-$X_{3e}$-$X_{4e}$-$X_{5e}$-$X_{6e}$-$X_{7e}$ and (f) CDRL3 of the general formula (VI): $X_{1f}$-$X_{2f}$-$X_{3f}$-$X_{4f}$-$X_{5f}$-$X_{6f}$-$X_{7f}$-$X_{8f}$-$X_{9f}$-$X_{10f}$-$X_{11f}$ wherein, $X_{1a}$ is an amino acid selected from serine and threonine;

$X_{2a}$ is an amino acid selected from phenylalanine and isoleucine;

$X_{3a}$ is an amino acid selected from threonine and alanine;

$X_{4a}$ is an amino acid selected from aspartic acid, serine and histidine;

$X_{5a}$ is an amino acid selected from tyrosine, asparagine, glycine and threonine;

Each of $X_{6a}$ and $X_{7a}$ may be present or absent and when present, is tyrosine amino acid;

$X_{1b}$ is an amino acid selected from valine, leucine, tyrosine and glutamic acid;

$X_{2b}$ is an amino acid selected from serine, asparagine and aspartic acid;

$X_{3b}$ is an amino acid selected from threonine, proline and tyrosine;

$X_{4b}$ is an amino acid selected from tyrosine, glycine, aspartic acid and serine;

$X_{5b}$ is an amino acid selected from tyrosine, threonine, glycine and alanine;

$X_{6b}$ is an amino acid selected from glycine, aspartic acid and threonine;

$X_{7b}$ is an amino acid selected from aspartic acid, tyrosine and asparagine;

$X_{1c}$ is an amino acid selected from aspartic acid, glutamic acid, alanine, and arginine;

$X_{2c}$ is an amino acid selected from leucine, aspartic acid, lysine and glycine;

$X_{3c}$ is an amino acid selected from aspartic acid, tyrosine, serine and leucine;

$X_{4c}$ is an amino acid selected from glycine, aspartic acid, arginine, tyrosine, leucine, serine and lysine;

$X_{5c}$ is an amino acid selected from tyrosine, arginine, aspartic acid, and glycine;

$X_{6c}$ is an amino acid selected from glutamic acid, serine, phenylalanine, tyrosine and asparagine;

$X_{7e}$ is an amino acid selected from serine, proline, aspartic acid, and phenylalanine or may be absent;

$X_{8c}$ is an amino acid selected from methionine, tryptophan, phenylalanine and valine or may be absent;

$X_{9c}$ is an amino acid selected from aspartic acid, and phenylalanine or may be absent;

Each of $X_{10c}$ and $X_{11c}$ may be present or absent and when present, is an amino acid independently selected from tyrosine and alanine;

Each of $X_{12c}$, $X_{13e}$ and $X_{14c}$ may be present or absent and when present, is an amino acid independently selected from methionine, aspartic acid and tyrosine;

$X_{1d}$ is an amino acid selected from arginine, lysine, leucine, serine, tyrosine and glutamic acid;

$X_{2a}$ is an amino acid selected from proline, serine, alanine, leucine, glycine and glutamime;

$X_{3d}$ is an amino acid selected from serine, aspartic acid, arginine and tryptophan;

$X_{4d}$ is an amino acid selected from glutamine, glycine, serine and leucine;

$X_{5d}$ is an amino acid selected from aspartic acid, serine, threonine, proline and leucine;

$X_{6d}$ is an amino acid selected from isoleucine, valine, leucine, serine, asparagine, phenylalanine and glycine;

$X_{7d}$ is an amino acid selected from asparagine, leucine, glycine, proline, isoleucine, lysine and histidine;

$X_{8d}$ is an amino acid selected from asparagine, aspartic acid, threonine, glycine, arginine, glutamine and tyrosine;

$X_{9d}$ is an amino acid selected from tyrosine, isoleucine, tryptophan, asparagine, glycine, valine, histidine and serine; $X_{10d}$ is an amino acid selected from leucine, asparagine, threonine, lysine, arginine and serine;

$X_{11d}$ is an amino acid selected from serine, glycine, alanine, tyrosine, proline, aspartic acid and asparagine;

$X_{12d}$ is an may be absent;

$X_{13d}$ is an amino acid selected from threonine, serine, asparagine and lysine or may be absent;

Each of $X_{14d}$, $X_{15d}$, $X_{16d}$ and $X_{17d}$ may be present or absent and when present, is an amino acid independently selected from tyrosine, leucine, asparagine and alanine;

$X_{1e}$ is an amino acid selected from aspartic acid, tryptophan, tyrosine, leucine and alanine;

$X_{2e}$ is an amino acid selected from asparagine, alanine, threonine and valine;

$X_{3e}$ is an amino acid selected from asparagine, serine and threonine;

$X_{4e}$ is an amino acid selected from lysine, threonine, arginine and serine;

$X_{5e}$ is an amino acid selected from arginine and leucine;

$X_{6e}$ is an amino acid selected from phenylalanine, glutamic acid, histidine, aspartic acid and alanine;

$X_{7e}$ is an amino acid selected from serine and aspartic acid; In one of the embodiments, CDR3 of the light chain (herein after referred as CDRL3) of the anti-properdin antibody or antigen binding portion thereof of the present invention has an amino acid sequence of $X_{1f}$-$X_{2f}$-$X_{3f}$-$X_{4f}$-$X_{5f}$-$X_{6f}$-$X_{7f}$-$X_{8f}$-$X_{9f}$-$X_{10f}$-$X_{11f}$ wherein $X_{1f}$ is an amino acid selected from histidine, glutamine, tryptophan, alanine, glycine and methionine;

$X_{2f}$ is an amino acid selected from glutamine, alanine and threonine;

$X_{3f}$ is an amino acid selected from tyrosine, glycine, leucine, arginine, tryptophan and glutamine;

$X_{4f}$ is an amino acid selected from leucine, asparagine, threonine, tyrosine, glutamine and aspartic acid;

$X_{5f}$ is an amino acid selected from serine, threonine, histidine, alanine and glycine;

$X_{6f}$ is an amino acid selected from serine, leucine, phenylalanine, threonine, isoleucine and tyrosine;

$X_{7f}$ is an amino acid selected from tyrosine, proline and leucine;

$X_{8f}$ is an amino acid selected from threonine, proline, tyrosine, tryptophan and arginine;

$X_{9f}$ is an amino acid selected from threonine and glutamic acid or may be absent;

$X_{10f}$ is an amino acid selected from alanine and leucine or no amino acid and $X_{11f}$ is valine amino acid or may be absent.

In one embodiment, the amino acid sequence of constant region of anti-properdin antibody comprises of the $IgG_1$, $IgG_2$, $IgG_3$, $IgG_4$, $IgG_2/G_4$, IgA, IgE, IgM or IgD constant region, preferably the $IgG_1$ or $IgG_4$.

In another embodiment, one or more anti-properdin antibodies of the present invention has modified or reduced or no ADCC and/or CDC activity. In one of the embodiments, the anti-properdin antibody or antigen binding portion thereof has reduced potential to cause the safety issue of ADCC and CDC.

In one of the embodiments, one or more anti-properdin antibodies of the present invention has reduced or no ADCP activity.

In one of the embodiments, the anti-properdin antibody or antigen binding portion thereof of the present invention has a $K_D$ of $10^{-8}$ M or less, more preferably $10^{-10}$ M or less for properdin antigen. $K_D$ value is a measurement of the binding affinity of the antibody towards its target antigen.

In one of the embodiments, the anti-properdin antibody or antigen binding portion thereof of the present invention cross-reacts with properdin from species other than human.

In one of the embodiments, the anti-properdin antibody or antigen binding portion thereof of the present invention has higher binding specificity towards human properdin.

In one of the embodiments, an anti-properdin antibody or antigen binding portion thereof of the present invention has an increased half-life in subject as compared to the anti-properdin antibody with conventional Fc fragment.

In one embodiment, the anti-properdin antibody or antigen binding portion thereof according to the present invention blocks the function of properdin in mediating alternate complement pathway activation.

In one embodiment, the anti-properdin antibody or antigen binding portion thereof according to the present invention prevents the binding of properdin to target cells.

In one embodiment, the anti-properdin antibody or antigen binding portion thereof according to the present invention can prevent the increased binding of C3b to the target cell surface.

In one embodiment, the anti-properdin antibody or antigen binding portion thereof according to the present invention regulates the MAC formation on the target cell surface and thereby preventing the lysis of cells.

In one embodiment, the anti-properdin antibody or antigen binding portion thereof according to the present invention can minimise the formation of anaphylatoxins, C3a and C5a.

In one embodiment, the anti-properdin antibody or antigen binding portion thereof according to the present invention prevents the complement mediated lysis of the target cells.

In one embodiment, the anti-properdin antibody or antigen binding portion thereof according to the present invention has improved circulating half-life.

In another embodiment, the anti-properdin antibody or antigen binding portion is able to bind to the monkey properdin enabling ease of drug development by providing a relevant animal pharmacology and toxicology model.

In one of the embodiments, the present invention provides a composition comprising an anti-properdin antibody that specifically binds human properdin (factor P) and an acceptable carrier.

In another embodiment, the anti-properdin antibody or antigen binding portion thereof of the present invention can be used for the treatment of disease where activity of properdin is detrimental such as infections, various cancers, auto immune disorders and other disorders such as PNH, aHUS where complement activity is amplified.

DETAILED DESCRIPTION OF THE INVENTION

In one embodiment, the anti-properdin antibody or antigen binding portion thereof of the present invention binds with high affinity to human properdin.

Amino Acid Sequences of the Anti-Properdin Antibody

In one of the embodiments, CDR1 of the heavy chain (herein after referred as CDRH1) of the anti-properdin antibody or antigen binding portion thereof of the present invention has an amino acid sequence of the general formula (I): $G$-$Y$-$X_{1a}$-$X_{2a}$-$X_{3a}$-$X_{4a}$-$X_{5a}$-$X_{6a}$-$X_{7a}$ wherein, $X_{1a}$ is an amino acid selected from serine and threonine;

$X_{2a}$ is an amino acid selected from phenylalanine and isoleucine;

$X_{3a}$ is an amino acid selected from threonine and alanine;

$X_{4a}$ is an amino acid selected from aspartic acid, serine and histidine;

$X_{5a}$ is an amino acid selected from tyrosine, asparagine, glycine and threonine;

Each of $X_{6a}$ and $X_{7a}$ may be present or absent and when present, is tyrosine amino acid.

In one of the embodiments, CDR2 of the heavy chain (herein after referred as CDRH2) of the anti-properdin antibody or antigen binding portion thereof of the present invention has an amino acid sequence of $X_{1b}$-$I$-$X_{2b}$-$X_{3b}$-$X_{4b}$-$X_{5b}$-$X_{6b}$-$X_7$b wherein, $X_{1b}$ is an amino acid selected from valine, leucine, tyrosine and glutamic acid;

$X_{2b}$ is an amino acid selected from serine, asparagine and aspartic acid;

$X_{3b}$ is an amino acid selected from threonine, proline and tyrosine;

$X_{4b}$ is an amino acid selected from tyrosine, glycine, aspartic acid and serine;

$X_{5b}$ is an amino acid selected from tyrosine, threonine, glycine and alanine;

$X_{6b}$ is an amino acid selected from glycine, aspartic acid and threonine;

$X_{7b}$ is an amino acid selected from aspartic acid, tyrosine and asparagine.

In one of the embodiments, CDR3 of the heavy chain (herein after referred as CDRH3) of the anti-properdin antibody or antigen binding portion thereof of the present invention has an amino acid sequence of $X_{1c}$-$X_{2c}$-$X_{3c}$-$X_{4c}$-$X_{5c}$-$X_{6c}$-$X_{7c}$-$X_{8c}$-$X_{9c}$-$X_{10c}$-$X_{11c}$-$X_{12c}$-$X_{13c}$-$X_{14c}$ wherein, $X_{1c}$ is an amino acid selected from aspartic acid, glutamic acid, alanine, and arginine;

$X_{2c}$ is an amino acid selected from leucine, aspartic acid, lysine and glycine;

$X_{3c}$ is an amino acid selected from aspartic acid, tyrosine, serine and leucine;

$X_{4c}$ is an amino acid selected from glycine, aspartic acid, arginine, tyrosine, leucine, serine and lysine;

$X_{5c}$ is an amino acid selected from tyrosine, arginine, aspartic acid, and glycine;

$X_{6c}$ is an amino acid selected from glutamic acid, serine, phenylalanine, tyrosine and asparagine;

$X_{7c}$ is an amino acid selected from serine, proline, aspartic acid, and phenylalanine or no amino acid;

$X_{8c}$ is an amino acid selected from methionine, tryptophan, phenylalanine and valine or no amino acid;

$X_{9c}$ is an amino acid selected from aspartic acid, and phenylalanine or no amino acid;

Each of $X_{10c}$ and $X_{11c}$ is present or absent and when present, is an amino acid independently selected from tyrosine and alanine;

Each of $X_{12c}$, $X_{13c}$ and $X_{14c}$ is present or absent and when present, is an amino acid independently selected from methionine, aspartic acid and tyrosine.

In one of the embodiments, CDR1 of the light chain (herein after referred as CDRL1) of the anti-properdin antibody or antigen binding portion thereof of the present invention has an amino acid sequence of $X_{1d}$-$X_{2d}$-$X_{3d}$-$X_{4d}$-$X_{5d}$-$X_{6d}$-$X_{7d}$-$X_{8d}$-$X_{9d}$-$X_{10d}$-$X_{11d}$-$X_{12d}$-$X_{13d}$-$X_{14d}$-$X_{15d}$-$X_{16d}$-$X_{17d}$ wherein, $X_{1d}$ is an amino acid selected from arginine, lysine, leucine, serine, tyrosine and glutamic acid;

$X_{2d}$ is an amino acid selected from proline, serine, alanine, leucine, glycine and glutamime;

$X_{3d}$ is an amino acid selected from serine, aspartic acid, arginine and tryptophan;

$X_{4d}$ is an amino acid selected from glutamine, glycine, serine and leucine;

$X_{5d}$ is an amino acid selected from aspartic acid, serine, threonine, proline and leucine;

$X_{6d}$ is an amino acid selected from isoleucine, valine, leucine, serine, asparagine, phenylalanine and glycine;

$X_{7d}$ is an amino acid selected from asparagine, leucine, glycine, proline, isoleucine, lysine and histidine;

$X_{8d}$ is an amino acid selected from asparagine, aspartic acid, threonine, glycine, arginine, glutamine and tyrosine;

$X_{9d}$ is an amino acid selected from tyrosine, isoleucine, tryptophan, asparagine, glycine, valine, histidine and serine;

$X_{10d}$ is an amino acid selected from leucine, asparagine, threonine, lysine, arginine and serine;

$X_{11d}$ is an amino acid selected from serine, glycine, alanine, tyrosine, proline, aspartic acid and asparagine;

$X_{12d}$ is an amino acid selected from lysine, valine, threonine, alanine and glutamine or no amino acid;

$X_{13d}$ is an amino acid selected from threonine, serine, asparagine and lysine or no amino acid;

Each of $X_{14d}$, $X_{15d}$, $X_{16d}$ and $X_{17d}$ is present or absent and when present, is an amino acid independently selected from tyrosine, leucine, asparagine and alanine. In one of the embodiments, CDR2 of the light chain (herein after referred as CDRL2) of the anti-properdin antibody or antigen binding portion thereof of the present invention has an amino acid sequence of $X_{1e}$-$X_{2e}$-$X_{3e}$-$X_{4e}$-$X_{5e}$-$X_{6e}$-$X_{7e}$ wherein, $X_{1e}$ is an amino acid selected from aspartic acid, tryptophan, tyrosine, leucine and alanine;

$X_{2e}$ is an amino acid selected from asparagine, alanine, threonine and valine;

$X_{3e}$ is an amino acid selected from asparagine, serine and threonine;

$X_{4e}$ is an amino acid selected from lysine, threonine, arginine and serine;

$X_{5e}$ is an amino acid selected from arginine and leucine;

$X_{6e}$ is an amino acid selected from phenylalanine, glutamic acid, histidine, aspartic acid and alanine;

$X_{7e}$ is an amino acid selected from serine and aspartic acid

In one of the embodiments, CDR3 of the light chain (herein after referred as CDRL3) of the anti-properdin antibody or antigen binding portion thereof of the present invention has an amino acid sequence of $X_{1f}$-$X_{2f}$-$X_{3f}$-$X_{4f}$-$X_{5f}$-$X_{6f}$-$X_{7f}$-$X_{8f}$-$X_{9f}$-$X_{10f}$-$X_{11f}$ $X_{1f}$ is an amino acid selected from histidine, glutamine, tryptophan, alanine, glycine and methionine;

$X_{2f}$ is an amino acid selected from glutamine, alanine and threonine;

$X_{3f}$ is an amino acid selected from tyrosine, glycine, leucine, arginine, tryptophan and glutamine;

$X_{4f}$ is an amino acid selected from leucine, asparagine, threonine, tyrosine, glutamine and aspartic acid;

$X_{5f}$ is an amino acid selected from serine, threonine, histidine, alanine and glycine;

$X_{6f}$ is an amino acid selected from serine, leucine, phenylalanine, threonine, isoleucine and tyrosine;

$X_{7f}$ is an amino acid selected from tyrosine, proline and leucine;

$X_{8f}$ is an amino acid selected from threonine, proline, tyrosine, tryptophan and arginine;

$X_{9f}$ is an amino acid selected from threonine and glutamic acid or no amino acid;

$X_{10f}$ is an amino acid selected from alanine and leucine or no amino acid;

$X_{11f}$ is valine amino acid or no amino acid

In one of the embodiments, CDRH1, CDRH2, CDRH3, CDRL1, CDRL2 and CDRL3 of anti-properdin antibody or antigen binding portion thereof of the present invention is selected from the amino acid sequences as given below in table 2.

TABLE 2

Amino acid sequences of CDR regions of anti-properdin antibodies

| Sequence ID No. | CDR region | Amino acid sequence of CDR region |
|---|---|---|
| 1 | CDRH1 | GYTFTDY |
| 2 | CDRH1 | GYTFAHN |
| 3 | CDRH1 | GYSITSGYY |
| 4 | CDRH1 | GYSITSTYY |
| 5 | CDRH1 | GYSFTSY |
| 6 | CDRH2 | VISTYYGD |
| 7 | CDRH2 | LISTYYGD |
| 8 | CDRH2 | YINPGTDY |
| 9 | CDRH2 | YISYDGGN |
| 10 | CDRH2 | YISYDGTN |
| 11 | CDRH2 | EIDPSAGY |
| 12 | CDRH3 | DGYLDY |
| 13 | CDRH3 | ADSSGNFFDY |
| 14 | CDRH3 | RKLYGNFVDYAMDY |
| 15 | CDRH3 | DLDGYESMDY |
| 16 | CDRH3 | DDYDRSPWFAY |
| 17 | CDRH3 | EGYRYFDV |
| 18 | CDRH3 | EGYKYFDV |
| 19 | CDRL1 | SGSSSNIGNNYVS |
| 20 | CDRL1 | KSSQSLLYSSNQKNYLA |
| 21 | CDRL1 | RPSQDINNYLS |
| 22 | CDRL1 | KSSQSLLDINGKTYLN |
| 23 | CDRL1 | LASQTIGTWLA |
| 24 | CDRL1 | RLDGSSPGNNYVS |
| 25 | CDRL1 | SGSSSNIRGTPTT |
| 26 | CDRL1 | SGSSSNLGVKDVN |
| 27 | CDRL1 | YPRLLFKGNNYVS |
| 28 | CDRL1 | SGSSSNHQHRPAS |
| 29 | CDRL1 | EQWSPGHGNNYVS |
| 30 | CDRL2 | DNNKRFS |
| 31 | CDRL2 | WASTRES |
| 32 | CDRL2 | YTSRLHS |
| 33 | CDRL2 | LVSKLDS |
| 34 | CDRL2 | AATSLAD |
| 35 | CDRL3 | GAWDGSLREAV |
| 36 | CDRL3 | QQYYSYPYTL |
| 37 | CDRL3 | HQYLSSYT |

TABLE 2-continued

Amino acid sequences of CDR regions of
anti-properdin antibodies

| Sequence ID No. | CDR region | Amino acid sequence of CDR region |
|---|---|---|
| 38 | CDRL3 | QQGNTLPPT |
| 39 | CDRL3 | WQGTHFPYT |
| 40 | CDRL3 | QQLYSTPWT |
| 41 | CDRL3 | AARQHLLREAV |
| 42 | CDRL3 | GAWDASLREAV |
| 43 | CDRL3 | MTQNGILREAV |

Accordingly, in another embodiment, the present invention provides an anti-properdin antibody, or antigen-binding portion thereof, comprising: a heavy chain variable region that comprises CDRH1, CDRH2, and CDRH3 sequences; and a light chain variable region that comprises CDRL1, CDRL2, and CDRL3 sequences, wherein:

(a) the heavy chain variable region CDRH3 comprising an amino acid sequence selected from the group consisting of SEQ ID NOs: 12, 13, 14, 15, 16, 17 and 18, and conservative modifications thereof; (b) light chain variable region CDRL3 comprising an amino acid sequence selected from the group consisting of SEQ ID NOs: 35, 36, 37, 38, 39, 40, 41, 42 and 43, and conservative modifications thereof.

In another preferred embodiment, the heavy chain variable region CDRH2 comprising an amino acid sequence selected from the group consisting of SEQ ID NOs: 6, 7, 8, 9, 10 and 11, and conservative modifications thereof; and light chain variable region CDRL2 comprising an amino acid sequence selected from the group consisting of SEQ ID NOs: 30, 31, 32, 33 and 34 and conservative modifications thereof.

In another preferred embodiment, heavy chain variable region CDRH1 comprising an amino acid sequence selected from the group consisting of SEQ ID NOs: 1, 2, 3, 4 and 5, and conservative modifications thereof; and the light chain variable region CDRL1 comprising an amino acid sequence selected from the group consisting of SEQ ID NOs: 19, 20, 21, 22, 23, 24, 25, 26, 27, 28 and 29 and conservative modifications thereof.

In another embodiment, the present invention provides an antibody, or antigen-binding portion thereof comprising:

(a) a heavy chain variable region CDRH1 comprising an amino acid sequence selected from the group consisting of SEQ ID NOs: 1, 2, 3, 4 and 5;

(b) a heavy chain variable region CDRH2 comprising an amino acid sequence selected from the group consisting of SEQ ID NOs: 6, 7, 8, 9, 10 and 11;

(c) a heavy chain variable region CDRH3 comprising an amino acid sequence selected from the group consisting of SEQ ID NOs: 12, 13, 14, 15, 16, 17 and 18;

(d) a light chain variable region CDRL1 comprising an amino acid sequence selected from the group consisting of SEQ ID NOs: 19, 20, 21, 22, 23, 24, 25, 26, 27, 28, and 29;

(e) a light chain variable region CDRL2 comprising an amino acid sequence selected from the group consisting of SEQ ID NOs: 30, 31, 32, 33, and 34; and (f) a light chain variable region CDRL3 comprising an amino acid sequence selected from the group consisting of SEQ ID NOs: 35, 36, 37, 38, 39, 40, 41, 42 and 43; wherein the antibody specifically binds properdin, preferably human properdin.

In one of the embodiments, HCVR and LCVR of anti-properdin antibody or antigen binding portion thereof of the present invention is selected from the amino acid sequences as given in below table 3.

TABLE 3

Amino acid sequence of variable region of anti-properdin antibodies

| Seq ID No. | Variable region | Amino acid sequence of variable region |
|---|---|---|
| 44 | HCVR | QVQLQQSGPELVRPGVSVKISCKGSGYTFTDYALHWVKQSHAESLEWIGVISTYYGDASYNQ KFKDKATMTVDISSSTAYLELARLTSEDSAIYYCARDGYLDYWGQGTLVTVSS |
| 45 | HCVR | QVQLQQSGPELVRPGVSVKISCKGSGYTFTDYAMHWVKQSHAESLEWIGLISTYYGDAGYNQ KFKDKATMTVDISSSTAYLELARLTSEDSAIYYCARADSSGNFFDYWGQGTLVTVSS |
| 46 | HCVR | EVQLQQSGPELVKPGASVKMSCKASGYTFAHNWIHWVKQKPGQGLEWIGYINPGTDYTEYSQ RFKGKATLTSDKSSSTAYMELSSLTSEDSAVYYCARRKLYGNFVDYAMDYWGQGTLVTVSA |
| 47 | HCVR | QVQLQESGPGLVKPSQTLSLTCTVSGYSITSGYYWNWIRQHPGKGLEWIGYISYDGGNKYNP SLKSRVTISRDTSKNQFSLKLSSVTAADTAVYYCARDLDGYESMDYWGQGTSVTVSS |
| 48 | HCVR | QVQLQESGPGLVKPSQTLSLTCTVSGYSITSTYYWNWIRQHPGKGLEWIGYISYDGTNKYNP SLKSRVTISRDTSKNQFSLKLSSVTAADTAVYYCARDDYDRSPWFAYWGQGTLVTVSS |
| 49 | HCVR | QVQLQQPGAELVKPGASVILSCKASGYSFTSYWVHWVKQRPGQGLEWIGEIDPSAGYTNFNQ KFRDMATLTVDKSSSTAYMQLSSLTSEDSAVYFCTREGYRYFDVWGAGTTVTVSS |
| 50 | HCVR | QVQLKESGAELVRPGVSVKISCKGSGYTFTDYAMHWVKQSHAKSLEWIGVISTYYGDASYNQ KFKGKATMTVDKSSSTAYMELARLTSEDSAIYYCARDGYLDYWGQGTTLTVSS |
| 51 | HCVR | GAELVRPGVSVKISCKGSGYTFTDYAMHWVKQSHAKSLEWIGLISTYYGDARYNQKFRGKAT MTVDKSSSTAYMELARLTSEDSAIYYCARADSSGNFFDYWGQGTTLTVSSAKTTPPSV |
| 52 | HCVR | GAELAKPGASVKMSCKASGYTFAHNWMHWVKQRPGQGLEWIGYINPGTDYTEYSQRFKDKAT LTADKSSSTAYMQLSSLTSEDSAVYYCARRKLYGNFVDYAMDYWGQGTSVTVSSAKTTPPSV YPLA |

TABLE 3-continued

Amino acid sequence of variable region of anti-properdin antibodies

| Seq ID No. | Variable region | Amino acid sequence of variable region |
|---|---|---|
| 53 | HCVR | GPGLVKPSQSLSLTCSVTGYSITSGYYWNWIRQFPGNKLEWMGYISYDGGNIYNPSLKNRIS ITRDTSKNQFFLKLNSVTSEDTATYYCARDLDGYESMDYWGQGTSVTVSSAKTTPPSVYPLA |
| 54 | HCVR | KPSQSLSLTCSVTGYSITSTYYWNWIRQFPGNKLEWMGYISYDGTNKYNPSLKNRISITRDT SKNRFFLKLNSVTTEDTATYYCAGDDYDRSPWFAYWGQGTLVTVSAAKTTPPSV |
| 55 | HCVR | QVQLVQSGAEVKKPGASVKVSCKASGYSFTSYWMHWVRQAPGQGLEWMGEIDPSAGYTNYNQ KFTGRVTMTRDTSTSTVYMELSSLRSEDTAVYYCTREGYKYFDVWGAGTTVTVSS |
| 56 | LCVR | QSVLTQPPSVSAAPGQKVTISCSGSSSNIGNNYVSWYVQLPGTAPKLLIYDNNKRFSGVPDR FSGSKSGTSATLGITGLQTGDEADYYCGAWDGSLREAVFGGGTKVTVLR |
| 57 | LCVR | DIVMTQSPDSLAVSLGERATINCKSSQSLLYSSNQKNYLAWYQQKPGQPPKLLIYWASTRES GVPDRFSGSGSGTDFTLTISSLQAEDVAVYYCQQYYSYPYTFGGGTKLEIK |
| 58 | LCVR | DIVMTQSPDSLAVSLGERATINCKSSQSVLYSSNQKNYLAWYQQKPGQPPKLLIYWASTRES GVPDRFSGSGSGTDFTLTISSLQAEDVAVYYCHQYLSSYTFGQGTKVEIKR |
| 59 | LCVR | DIQMTQSPSSLSASVGDRVTITCRPSQDINNYLSWYQQKPGKAPKLLIYYTSRLHSGVPSRF SGSGSGTDFTFTISSLQPEDIATYYCQQGNTLPPTFGQGTKVEIKR |
| 60 | LCVR | DIVMTQSPLSLSVTPGQPASISCKSSQSLLDINGKTYLNWYLQKPGQSPQLLIYLVSKLDSG VPDRFSGSGSGTDFTLKISRVEAEDVGVYYCWQGTHFPYTFGQGTKVEIKR |
| 61 | LCVR | DIQMTQSPSSLSASVGDRVTITCLASQTIGTWLAWYQQKPGKAPKLLIYAATSLADGVPSRF SGSGSGTDFTLTISSLQPEDFATYYCQQLYSTPWTFGGGTKLEIKR |
| 62 | LCVR | QSVLTQPPSVSAAPGQKVTISCSGSSSNIGNNYVSWYVQLPGTAPKLLIYDNNKRFSGVPDR FSGSKSGTSATLGITGLQTGDEADYYCGAWDGSLREAVFGGGTKVTVLRPLDPKISELKLL KVV |
| 63 | LCVR | SSLAVSAGEKVTMSCKSSQSVLYSSNQKNYLAWYQQKPGQSPKLLIYWASTRESGVPDRFTG SGSGTDFTLTISSVQAEDLAVYYCHQYLSSYT |
| 64 | LCVR | PSSLAVSVGEKVTLNCKSSQSLLYSSNQKNYLAWYQQKPGQSPKLLINWASTRESGVPDRCT GSGSGTDFTLTISNVKAEDLAVYYCQQYYSYPYTL |
| 65 | LCVR | LTLSVTFGQPASISCKSSQSLLDINGKTYLNWLLQRPGQSPKRLIYLVSKLDSGVPDRFTGS GSGTDFTLKISRVEAEDLGIYYCWQGTHFPYT |
| 66 | LCVR | DIVLTQSPASQSASLGESVTITCLASQTIGTWLAWYQQKPGKSPQLLIYAATSLADGVPSRF SGSGSGTKFSFKISSLQAEDFVSYYCQQLYSTPWTFGGGTKLEIKR |
| 67 | LCVR | QSVLTQPPSVSAAPGQKVTISCRLDGSSPGNNYVSWYVQLPGTAPKLLIYDNNKRFSGVPDR FSGSKSGTSATLGITGLQTGDEADYYCAARQHLLREAVFGGGTKVTVLR |
| 68 | LCVR | QSVLTQPPSVSAAPGQKVTISCSGSSSNIRGTPTTWYVQLPGTAPKLLIYDNNKRFSGVPDR FSGSKSGTSATLGITGLQTGDEADYYCGAWDGSLREAVFGGGTKVTVLR |
| 69 | LCVR | QSVLTQPPSVSAAPGQKVTISCSGSSSNLGVKDVNWYVQLPGTAPKLLIYDNNKRFSGVPDR FSGSKSGTSATLGITGLQTGDEADYYCGAWDASLREAVFGGGTKVTVLR |
| 70 | LCVR | QSVLTQPPSVSAAPGQKVTISCYPRLLFKGNNYVSWYVQLPGTAPKLLIYDNNKRFSGVPDR FSGSKSGTSATLGITGLQTGDEADYYCGAWDGSLREAVFGGGTKVTVLR |
| 71 | LCVR | QSVLTQPPSVSAAPGQKVTISCSGSSSNHQHRPASWYVQLPGTAPKLLIYDNNKRFSGVPDR FSGSKSGTSATLGITGLQTGDEADYYCMTQNGILREAVFGGGTKVTVLR |
| 72 | LCVR | QSVLTQPPSVSAAPGQKVTISCSGSSSNIGNNYVSWYVQLPGTAPKLLIYDNNKRFSGVPDR FSGSKSGTSATLGITGLQTGDEADYYCMTQNGILREAVFGGGTKVTVLR |
| 73 | LCVR | QSVLTQPPSVSAAPGQKVTISCRLDGSSPGNNYVSWYVQLPGTAPKLLIYDNNKRFSGVPDR FSGSKSGTSATLGITGLQTGDEADYYCMTQNGILREAVFGGGTKVTVLR |
| 74 | LCVR | QSVLTQPPSVSAAPGQKVTISCSGSSSNIRGTPTTWYVQLPGTAPKLLIYDNNKRFSGVPDR FSGSKSGTSATLGITGLQTGDEADYYCMTQNGILREAVFGGGTKVTVLR |
| 75 | LCVR | QSVLTQPPSVSAAPGQKVTISCSGSSSNLGVKDVNWYVQLPGTAPKLLIYDNNKRFSGVPDR FSGSKSGTSATLGITGLQTGDEADYYCMTQNGILREAVFGGGTKVTVLR |
| 76 | LCVR | QSVLTQPPSVSAAPGQKVTISCYPRLLFKGNNYVSWYVQLPGTAPKLLIYDNNKRFSGVPDR FSGSKSGTSATLGITGLQTGDEADYYCMTQNGILREAVFGGGTKVTVLR |
| 77 | LCVR | QSVLTQPPSVSAAPGQKVTISCSGSSSNIGNNYVSWYVQLPGTAPKLLIYDNNKRFSGVPDR FSGSKSGTSATLGITGLQTGDEADYYCAARQHLLREAVFGGGTKVTVLR |

TABLE 3-continued

Amino acid sequence of variable region of anti-properdin antibodies

| Seq ID No. | Variable region | Amino acid sequence of variable region |
|---|---|---|
| 78 | LCVR | QSVLTQPPSVSAAPGQKVTISCSGSSSNIRGTPTTWYVQLPGTAPKLLIYDNNKRFSGVPDR FSGSKSGTSATLGITGLQTGDEADYYCAARQHLLREAVFGGGTKVTVLR |
| 79 | LCVR | QSVLTQPPSVSAAPGQKVTISCEQWSPGHGNNYVSWYVQLPGTAPKLLIYDNNKRFSGVPDR FSGSKSGTSATLGITGLQTGDEADYYCAARQHLLREAVFGGGTKVTVLR |
| 80 | LCVR | QSVLTQPPSVSAAPGQKVTISCYPRLLFKGNNYVSWYVQLPGTAPKLLIYDNNKRFSGVPDR FSGSKSGTSATLGITGLQTGDEADYYCAARQHLLREAVFGGGTKVTVLR |
| 81 | LCVR | QSVLTQPPSVSAAPGQKVTISCSGSSSNHQHRPASWYVQLPGTAPKLLIYDNNKRFSGVPDR FSGSKSGTSATLGITGLQTGDEADYYCAARQHLLREAVFGGGTKVTVLR |
| 82 | LCVR | QSVLTQPPSVSAAPGQKVTISCRLDGSSPGNNYVSWYVQLPGTAPKLLIYDNNKRFSGVPDR FSGSKSGTSATLGITGLQTGDEADYYCGAWDGSLREAVFGGGTKVTVLR |
| 83 | LCVR | QSVLTQPPSVSAAPGQKVTISCSGSSSNHQHRPASWYVQLPGTAPKLLIYDNNKRFSGVPDR FSGSKSGTSATLGITGLQTGDEADYYCGAWDGSLREAVFGGGTKVTVLR |

In one of the embodiments, variable region of heavy chain of anti-properdin antibody or antigen binding portion thereof of the present invention comprising of CDRH1, CDRH2 and CDRH3 comprising amino acid sequences selected from below given table 4.

TABLE 4

CDR regions of HCVR sequences of anti-properdin antibodies

| Seq ID No. of HCVR | CDR regions of HCVR sequences | | |
|---|---|---|---|
| | CDRH1 | CDRH2 | CDRH3 |
| 44 | GYTFTDY (SEQ ID NO: 1) | VISTYYGD (SEQ ID NO: 6) | DGYLDY (SEQ ID NO: 12) |
| 45 | GYTFTDY (SEQ ID NO: 1) | LISTYYGD (SEQ ID NO: 7) | ADSSGNFFDY (SEQ ID NO: 13) |
| 46 | GYTFAHN (SEQ ID NO: 2) | YINPGTDY (SEQ ID NO: 8) | RKLYGNFVDYAMDY (SEQ ID NO: 14) |
| 47 | GYSFTSGYY (SEQ ID NO: 3) | YISYDGGN (SEQ ID NO: 9) | DLDGYESMDY (SEQ ID NO: 15) |
| 48 | GYSITSTYY (SEQ ID NO: 4) | YISYDGTN (SEQ ID NO: 10) | DDYDRSPWFAY (SEQ ID NO: 16) |
| 49 | GYSFTSY (SEQ ID NO: 5) | EIDPSAGY (SEQ ID NO: 11) | EGYRYFDV (SEQ ID NO: 17) |
| 50 | GYTFTDY (SEQ ID NO: 1) | VISTYYGD (SEQ ID NO: 6) | DGYLDY (SEQ ID NO: 12) |
| 51 | GYTFTDY (SEQ ID NO: 1) | LISTYYGD (SEQ ID NO: 7) | ADSSGNFFDY (SEQ ID NO: 13) |
| 52 | GYTFAHN (SEQ ID NO: 2) | YINPGTDY (SEQ ID NO: 8) | RKLYGNFVDYAMDY (SEQ ID NO: 14) |

TABLE 4-continued

CDR regions of HCVR sequences of anti-properdin antibodies

| Seq ID No. of HCVR | CDR regions of HCVR sequences | | |
|---|---|---|---|
| | CDRH1 | CDRH2 | CDRH3 |
| 53 | GYSFTSGYY (SEQ ID NO: 3) | YISYDGGN (SEQ ID NO: 9) | DLDGYESMDY (SEQ ID NO: 15) |
| 54 | GYSITSTYY (SEQ ID NO: 4) | YISYDGTN (SEQ ID NO: 10) | DDYDRSPWFAY (SEQ ID NO: 16) |
| 55 | GYSFTSY (SEQ ID NO: 5) | EIDPSAGY (SEQ ID NO: 11) | EGYKYFDV (SEQ ID NO: 18) |

In one of the embodiments, variable region of light chain of anti-properdin antibody or antigen binding portion thereof of the present invention has combination of amino acid sequences of CDRL1, CDRL2 and CDRL3 selected from below given table 5.

TABLE 5

CDR regions of LCVR sequences of anti-properdin antibodies

| Seq ID No. of LCVR | CDR regions of LCVR sequences | | |
|---|---|---|---|
| | CDRL1 | CDRL2 | CDRL3 |
| 56 | SGSSSNIGNNYVS (SEQ ID NO: 19) | DNNKRFS (SEQ ID NO: 30) | GAWDGSLREAV (SEQ ID NO: 35) |
| 57 | KSSQSLLYSSNQKNYLA (SEQ ID NO: 20) | WASTRES (SEQ ID NO: 31) | QQYYSYPYT (SEQ ID NO: 98) |
| 58 | KSSQSVLYSSNQKNYLA (SEQ ID NO: 97) | WASTRES (SEQ ID NO: 31) | HQYLSSYT (SEQ ID NO: 37) |

TABLE 5-continued

| Seq ID No. of LCVR | CDR regions of LCVR sequences of anti-properdin antibodies | | |
|---|---|---|---|
| | CDRL1 | CDRL2 | CDRL3 |
| 59 | RPSQDINNYLS (SEQ ID NO: 21) | YTSRLHS (SEQ ID NO: 32) | QQGNTLPPT (SEQ ID NO: 38) |
| 60 | KSSQSLLDINGKTYLN (SEQ ID NO: 22) | LVSKLDS (SEQ ID NO: 33) | WQGTHFPYT (SEQ ID NO: 39) |
| 61 | LASQTIGTWLA (SEQ ID NO: 23) | AATSLAD (SEQ ID NO: 34) | QQLYSTPWT (SEQ ID NO: 40) |
| 62 | SGSSSNIGNNYVS (SEQ ID NO: 19) | DNNKRFS (SEQ ID NO: 30) | GAWDGSLREAV (SEQ ID NO: 35) |
| 63 | KSSQSVLYSSNQKNYLA (SEQ ID NO: 97) | WASTRES (SEQ ID NO: 31) | HQYLSSYT (SEQ ID NO: 37) |
| 64 | KSSQSLLYSSNQKNYLA (SEQ ID NO: 20) | WASTRES (SEQ ID NO: 31) | QQYYSYPYTL (SEQ ID NO: 36) |
| 65 | KSSQSLLDINGKTYLN (SEQ ID NO: 22) | LVSKLDS (SEQ ID NO: 33) | WQGTHFPYT (SEQ ID NO: 39) |
| 66 | LASQTIGTWLA (SEQ ID NO: 23) | AATSLAD (SEQ ID NO: 34) | QQLYSTPWT (SEQ ID NO: 40) |
| 67 | RLDGSSPGNNYVS (SEQ ID NO: 24) | DNNKRFS (SEQ ID NO: 30) | AARQHLLREAV (SEQ ID NO: 41) |
| 68 | SGSSSNIRGTPTT (SEQ ID NO: 25) | DNNKRFS (SEQ ID NO: 30) | GAWDGSLREAV (SEQ ID NO: 35) |
| 69 | SGSSSNLGVKDVN (SEQ ID NO: 26) | DNNKRFS (SEQ ID NO: 30) | GAWDASLREAV (SEQ ID NO: 42) |
| 70 | YPRLLFKGNNYVS (SEQ ID NO: 27) | DNNKRFS (SEQ ID NO: 30) | GAWDGSLREAV (SEQ ID NO: 35) |
| 71 | SGSSSNHQHRPAS (SEQ ID NO: 28) | DNNKRFS (SEQ ID NO: 30) | MTQNGILREAV (SEQ ID NO: 43) |
| 72 | SGSSSNIGNNYVS (SEQ ID NO: 19) | DNNKRFS (SEQ ID NO: 30) | MTQNGILREAV (SEQ ID NO: 43) |
| 73 | RLDGSSPGNNYVS (SEQ ID NO: 24) | DNNKRFS (SEQ ID NO: 30) | MTQNGILREAV (SEQ ID NO: 43) |
| 74 | SGSSSNIRGTPTT (SEQ ID NO: 25) | DNNKRFS (SEQ ID NO: 30) | MTQNGILREAV (SEQ ID NO: 43) |
| 75 | SGSSSNLGVKDVN (SEQ ID NO: 26) | DNNKRFS (SEQ ID NO: 30) | MTQNGILREAV (SEQ ID NO: 43) |
| 76 | YPRLLFKGNNYVS (SEQ ID NO: 27) | DNNKRFS (SEQ ID NO: 30) | MTQNGILREAV (SEQ ID NO: 43) |

TABLE 5-continued

| Seq ID No. of LCVR | CDR regions of LCVR sequences of anti-properdin antibodies | | |
|---|---|---|---|
| | CDRL1 | CDRL2 | CDRL3 |
| 77 | SGSSSNIGNNYVS (SEQ ID NO: 19) | DNNKRFS (SEQ ID NO: 30) | AARQHLLREAV (SEQ ID NO: 41) |
| 78 | SGSSSNIRGTPTT (SEQ ID NO: 25) | DNNKRFS (SEQ ID NO: 30) | AARQHLLREAV (SEQ ID NO: 41) |
| 79 | EQWSPGHGNNYVS (SEQ ID NO: 29) | DNNKRFS (SEQ ID NO: 30) | AARQHLLREAV (SEQ ID NO: 41) |
| 80 | YPRLLFKGNNYVS (SEQ ID NO: 27) | DNNKRFS (SEQ ID NO: 30) | AARQHLLREAV (SEQ ID NO: 41) |
| 81 | SGSSSNHQHRPAS (SEQ ID NO: 28) | DNNKRFS (SEQ ID NO: 30) | AARQHLLREAV (SEQ ID NO: 41) |
| 82 | RLDGSSPGNNYVS (SEQ ID NO: 24) | DNNKRFS (SEQ ID NO: 30) | GAWDGSLREAV (SEQ ID NO: 35) |
| 83 | SGSSSNHQHRPAS (SEQ ID NO: 28) | DNNKRFS (SEQ ID NO: 30) | GAWDGSLREAV (SEQ ID NO: 35) |

Accordingly, the present invention provides an anti-properdin antibody, or antigen-binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs: 44, 45, 46, 47, 48, 49, 50, 51, 52, 53, 54 and 55;

(b) the light chain variable region comprises an amino acid sequence that is at least 80% homologous to an amino acid sequence selected from the group consisting of SEQ ID NOs: 56, 57, 58, 59, 60, 61, 62, 63, 64, 65, 66, 67, 68, 69, 70, 71, 72, 73, 74, 75, 76, 77, 78, 79, 80, 81, 82 and 83.

Preferably, the present invention provides an anti-properdin antibody, or antigen-binding portion thereof, comprising a heavy chain variable region and a light chain variable region, wherein:

(a) the heavy chain variable region comprises an amino acid sequence selected from the group consisting of SEQ ID NOs: 44, 45, 46, 47, 48, 49, 50, 51, 52, 53, 54 and 55;

(b) the light chain variable region comprises an amino acid sequence selected from the group consisting of SEQ ID NOs: 56, 57, 58, 59, 60, 61, 62, 63, 64, 65, 66, 67, 68, 69, 70, 71, 72, 73, 74, 75, 76, 77, 78, 79, 80, 81, 82 and 83.

A preferred combination of CDRs of anti-properdin antibody or antigen-binding portion thereof according to the present invention comprises:

(a) a heavy chain variable region CDRH1 comprising SEQ ID NO: 1;

(b) a heavy chain variable region CDRH2 comprising SEQ ID NO: 7;

(c) a heavy chain variable region CDRH3 comprising SEQ ID NO: 13;

(d) a light chain variable region CDRL1 comprising SEQ ID NO: 20;

(e) a light chain variable region CDRL2 comprising SEQ ID NO: 31; and (f) a light chain variable region CDRL3 comprising SEQ ID NO: 37

Another preferred combination of CDRs of anti-properdin antibody or antigen-binding portion thereof according to the present invention comprises:

(a) a heavy chain variable region CDRH1 comprising SEQ ID NO: 1;

(b) a heavy chain variable region CDRH2 comprising SEQ ID NO: 7;

(c) a heavy chain variable region CDRH3 comprising SEQ ID NO: 13;

(d) a light chain variable region CDRL1 comprising SEQ ID NO: 21;

(e) a light chain variable region CDRL2 comprising SEQ ID NO: 32; and (f) a light chain variable region CDRL3 comprising SEQ ID NO: 38

Another preferred combination of CDRs of anti-properdin antibody or antigen-binding portion thereof according to the present invention comprises:

(a) a heavy chain variable region CDRH1 comprising SEQ ID NO: 1;

(b) a heavy chain variable region CDRH2 comprising SEQ ID NO: 7;

(c) a heavy chain variable region CDRH3 comprising SEQ ID NO: 13;

(d) a light chain variable region CDRL1 comprising SEQ ID NO: 21;

(e) a light chain variable region CDRL2 comprising SEQ ID NO: 32; and (f) a light chain variable region CDRL3 comprising SEQ ID NO: 36

Another preferred combination of CDRs of anti-properdin antibody or antigen-binding portion thereof according to the present invention comprises:

(a) a heavy chain variable region CDRH1 comprising SEQ ID NO: 2;

(b) a heavy chain variable region CDRH2 comprising SEQ ID NO: 8;

(c) a heavy chain variable region CDRH3 comprising SEQ ID NO: 14;

(d) a light chain variable region CDRL1 comprising SEQ ID NO: 20;

(e) a light chain variable region CDRL2 comprising SEQ ID NO: 31; and (f) a light chain variable region CDRL3 comprising SEQ ID NO: 36

Another preferred combination of CDRs of anti-properdin antibody or antigen-binding portion thereof according to the present invention comprises:

(a) a heavy chain variable region CDRH1 comprising SEQ ID NO: 3;

(b) a heavy chain variable region CDRH2 comprising SEQ ID NO: 9;

(c) a heavy chain variable region CDRH3 comprising SEQ ID NO: 15;

(d) a light chain variable region CDRL1 comprising SEQ ID NO: 22;

(e) a light chain variable region CDRL2 comprising SEQ ID NO: 33; and (f) a light chain variable region CDRL3 comprising SEQ ID NO: 39

Another preferred combination of CDRs of anti-properdin antibody or antigen-binding portion thereof according to the present invention comprises:

(a) a heavy chain variable region CDRH1 comprising SEQ ID NO: 4;

(b) a heavy chain variable region CDRH2 comprising SEQ ID NO: 10;

(c) a heavy chain variable region CDRH3 comprising SEQ ID NO: 16;

(d) a light chain variable region CDRL1 comprising SEQ ID NO: 23;

(e) a light chain variable region CDRL2 comprising SEQ ID NO: 34; and (f) a light chain variable region CDRL3 comprising SEQ ID NO: 40

Another preferred combination of CDRs of anti-properdin antibody or antigen-binding portion thereof according to the present invention comprises:

(a) a heavy chain variable region CDRH1 comprising SEQ ID NO: 5;

(b) a heavy chain variable region CDRH2 comprising SEQ ID NO: 11;

(c) a heavy chain variable region CDRH3 comprising SEQ ID NO: 18;

(d) a light chain variable region CDRL1 comprising SEQ ID NO: 29;

(e) a light chain variable region CDRL2 comprising SEQ ID NO: 30; and (f) a light chain variable region CDRL3 comprising SEQ ID NO: 41

Another preferred combination of CDRs of anti-properdin antibody or antigen-binding portion thereof according to the present invention comprises:

(a) a heavy chain variable region CDRH1 comprising SEQ ID NO: 5;

(b) a heavy chain variable region CDRH2 comprising SEQ ID NO: 11;

(c) a heavy chain variable region CDRH3 comprising SEQ ID NO: 17;

(d) a light chain variable region CDRL1 comprising SEQ ID NO: 29;

(e) a light chain variable region CDRL2 comprising SEQ ID NO: 30; and (f) a light chain variable region CDRL3 comprising SEQ ID NO: 41

Another preferred combination of CDRs of anti-properdin antibody or antigen-binding portion thereof according to the present invention comprises:

(a) a heavy chain variable region CDRH1 comprising SEQ ID NO: 1;

(b) a heavy chain variable region CDRH2 comprising SEQ ID NO: 6;

(c) a heavy chain variable region CDRH3 comprising SEQ ID NO: 12;

(d) a light chain variable region CDRL1 comprising SEQ ID NO: 19;

(e) a light chain variable region CDRL2 comprising SEQ ID NO: 30; and (f) a light chain variable region CDRL3 comprising SEQ ID NO: 35

A preferred combination of HCVR and LCVR of anti-properdin antibody or antigen-binding portion thereof according to the present invention comprises:

(a) a heavy chain variable region comprising the amino acid sequence of SEQ ID NO: 51; and (b) a light chain variable region comprising the amino acid sequence of SEQ ID NO: 63

Another preferred combination of HCVR and LCVR of anti-properdin antibody or antigen-binding portion thereof according to the present invention comprises:

(a) a heavy chain variable region comprising the amino acid sequence of SEQ ID NO: 52; and (b) a light chain variable region comprising the amino acid sequence of SEQ ID NO: 64

Yet another preferred combination of HCVR and LCVR of anti-properdin antibody or antigen-binding portion thereof according to the present invention comprises:

(a) a heavy chain variable region comprising the amino acid sequence of SEQ ID NO: 53; and (b) a light chain variable region comprising the amino acid sequence of SEQ ID NO: 65

Another preferred combination of HCVR and LCVR of anti-properdin antibody or antigen-binding portion thereof according to the present invention comprises:

(a) a heavy chain variable region comprising the amino acid sequence of SEQ ID NO: 54; and (b) a light chain variable region comprising the amino acid sequence of SEQ ID NO: 66

Another preferred combination of HCVR and LCVR of anti-properdin antibody or antigen-binding portion thereof according to the present invention comprises:

(a) a heavy chain variable region comprising the amino acid sequence of SEQ ID NO: 45; and (b) a light chain variable region comprising the amino acid sequence of SEQ ID NO: 57

Yet another preferred combination of HCVR and LCVR of anti-properdin antibody or antigen-binding portion thereof according to the present invention comprises:

(a) a heavy chain variable region comprising the amino acid sequence of SEQ ID NO: 45; and (b) a light chain variable region comprising the amino acid sequence of SEQ ID NO: 58

Another preferred combination of HCVR and LCVR of anti-properdin antibody or antigen-binding portion thereof according to the present invention comprises:

(a) a heavy chain variable region comprising the amino acid sequence of SEQ ID NO: 45; and (b) a light chain variable region comprising the amino acid sequence of SEQ ID NO: 59

Yet another preferred combination of HCVR and LCVR of anti-properdin antibody or antigen-binding portion thereof according to the present invention comprises:

(a) a heavy chain variable region comprising the amino acid sequence of SEQ ID NO: 46; and (b) a light chain variable region comprising the amino acid sequence of SEQ ID NO: 57

Another preferred combination of HCVR and LCVR of anti-properdin antibody or antigen-binding portion thereof according to the present invention comprises:

(a) a heavy chain variable region comprising the amino acid sequence of SEQ ID NO: 47; and (b) a light chain variable region comprising the amino acid sequence of SEQ ID NO: 60

Another preferred combination of HCVR and LCVR of anti-properdin antibody or antigen-binding portion thereof according to the present invention comprises:

(a) a heavy chain variable region comprising the amino acid sequence of SEQ ID NO: 48; and (b) a light chain variable region comprising the amino acid sequence of SEQ ID NO: 61

Another preferred combination of HCVR and LCVR of anti-properdin antibody or antigen-binding portion thereof according to the present invention comprises:

(a) a heavy chain variable region comprising the amino acid sequence of SEQ ID NO: 55; and (b) a light chain variable region comprising the amino acid sequence of SEQ ID NO: 79

Yet another preferred combination of HCVR and LCVR of anti-properdin antibody or antigen-binding portion thereof according to the present invention comprises:

(a) a heavy chain variable region comprising the amino acid sequence of SEQ ID NO: 55; and (b) a light chain variable region comprising the amino acid sequence of SEQ ID NO: 56

Yet another preferred combination of HCVR and LCVR of anti-properdin antibody or antigen-binding portion thereof according to the present invention comprises:

(a) a heavy chain variable region comprising the amino acid sequence of SEQ ID NO: 50; and (b) a light chain variable region comprising the amino acid sequence of SEQ ID NO: 62

Another preferred combination of HCVR and LCVR of anti-properdin antibody or antigen-binding portion thereof according to the present invention comprises:

(a) a heavy chain variable region comprising the amino acid sequence of SEQ ID NO: 44; and (b) a light chain variable region comprising the amino acid sequence of SEQ ID NO: 56

Yet another preferred combination of HCVR and LCVR of anti-properdin antibody or antigen-binding portion thereof according to the present invention comprises:

(a) a heavy chain variable region comprising the amino acid sequence of SEQ ID NO: 49; and (b) a light chain variable region comprising the amino acid sequence of SEQ ID NO: 62

The antibodies according to the present invention can be full-length (for example, an $IgG_1$ or $IgG_4$ or $IgG_2$ antibody) or may comprise only an antigen-binding portion (for example, a Fab, $F(ab')_2$ or scFv fragment), and optionally be modified to effect functionality, e.g., to eliminate residual effector functions such as ADCC and CDC activity. Human antibodies can exist in two forms that are associated with hinge heterogeneity. In one form, an antibody comprises a stable four-chain construct of approximately 150-160 kDa in which the dimers are held together by an inter chain heavy chain disulfide bond. In a second form, the dimers are not linked via inter chain disulfide bonds and a molecule of about 75-80 kDa is formed composed of a covalently coupled light and heavy chain (half-antibody). The later form have been extremely difficult to separate, even after affinity purification. The frequency of appearance of the second form in various intact IgG isotypes is due to, but not limited to, structural differences associated with the hinge region isotype of the antibody. A single amino acid substitution in the hinge region of the human $IgG_4$ hinge can significantly reduce the appearance of the second form (6) to levels typically observed using a human $IgG_1$ hinge. Full-length antibodies comprising CDRs or variable regions of the present invention further comprise said single amino acid substitution (i.e., S228P) when it is developed in $IgG_4$ form.

In a further embodiment, the antibody or antigen-binding portion thereof targeting properdin antigen according to the present invention is murine, chimeric, human, or humanized in nature, preferably chimeric or human or humanized in nature, more preferably humanized in nature.

Preferably, the antibodies, preferably monoclonal antibodies of the present application, include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Generally, a humanized antibody has one or more amino acid residues introduced into it from a non-human source. Methods of preparing humanized antibodies are generally well known in the art. For example, humanization can be essentially performed following the method of Winter and co-workers (7, 8 9 and 10), by substituting rodent frameworks or CDR sequences for the corresponding sequences of a human antibody. In some embodiments, humanized forms of non-human (e.g., mouse) antibodies are human antibodies (recipient antibody) in which the CDR region amino acid residues of the non-human antibody (e.g., mouse, rat, rabbit, or non-human primate antibody) having the desired specificity, affinity, and binding capacity are grafted onto the framework scaffold of a human antibody.

In some instances, one or more framework region amino acid residues of the human immunoglobulin are also replaced by corresponding amino acid residues of the non-human antibody (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

In another aspect, anti-properdin antibody according to the present invention has increased FcRn binding and increased half-life with modified or reduced or no ADCC and/or CDC activity. The anti-properdin antibody according to the present invention can be given to the subject with reduced dose and with a better dose regimen due to increased half-life as compared to known anti-properdin antibodies. In one of the embodiments, the anti-properdin antibody according to the present invention has amino acid sequences of constant region of $IgG_4$ with P329G and/or M428L & N434S mutation. The constant region of anti-properdin antibody with mentioned all three mutations in IgG4 constant region is referred herein as IgG4 (GLS). In one of the aspects, anti-properdin antibody according to the present invention has reduced or no ADCP activity.

In one of the embodiments, the anti-properdin antibody according to the present invention is monoclonal antibody or bispecific antibody or polyclonal antibody, preferably monoclonal antibody.

Preparation of Antibodies

Antibodies according to the current invention are generated in mouse using standard methods well known in the art. The monoclonal antibodies of the present invention are converted into a humanized version for therapeutic use. The hybridoma cell lines discussed herein can readily be generated by those of ordinary skill in the art, given the guidance provided herein. Development of anti-properdin scFv phage display library was done after amplifying variable heavy (VH) and variable light (VL) genes from spleen RNA of the immunized mice. Both the $V_H$ and $V_L$ were joined with a peptide linker and cloned in phage display vector as described herein. Panning and screening for specific properdin binders were performed.

Further Modifications in CDR and Framework Region

The present invention encompasses antibodies having one or more mutations in the CDR and/or variable region described herein, that may have similar functional characteristics and biological activity as described for antibodies provided herein. These mutations are known to the person skilled in the art and well within the scope of the current invention.

Further Modifications in Constant Region

The present invention encompasses antibodies having one or more mutations in the hinge, CH2 or CH3 region that may be desirable, for example, to improve the circulating half-life of the antibody in subject, to completely abolish immune effector functions, to enhance effector functions, etc. These mutations are known to the person skilled in the art (11, 12).

Immunoconjugates and Bispecific Antibodies

An immunoconjugate comprising an antibody of the present invention, or antigen-binding portion thereof, linked to another therapeutic agent, such as a cytotoxin or a radioactive isotope can also be developed. A bispecific molecule comprising an antibody, or antigen-binding portion thereof, of the present invention, linked to a second functional moiety having a different binding specificity than said antibody, or antigen-binding portion thereof can be developed. In one of the embodiments, the second functional moiety according to the present invention can bind to antigen selected from C3, C5, C5a, C5b, C3a, C3b, Factor B, Factor H and C1q. Methods of making bispecific antibodies are known in the art.

Nucleic Acid Molecules Encoding Anti-Properdin Antibodies, Vectors and Host Cells In one embodiment, the present invention provides nucleic acid molecules encoding the antibodies, or antigen-binding portions thereof as well as expression vectors comprising such nucleic acids and host cells comprising such expression vectors. In the present application, pZRCIII vector is used for the cloning and expression of anti-properdin antibodies of the present invention. pZRCIII vector is described in patent document WO 2012/046255A2. The host cell according to the present invention is prokaryotic or eukaryotic cell, preferably the host cell is an *E. coli* cell or a mammalian cell, such as a CHO cell.

Combination of Anti-Properdin of the Present Invention with Other Drugs

The present invention provides a combination comprising at least two or more antibodies or antigen binding portion thereof wherein at least one antibody or antigen binding portion thereof is anti-properdin antibody of the present invention. The combination according to the present invention may comprise second antibody or antigen binding portion thereof selected from anti-C3 antibody, anti-C5 antibody, anti-C5a antibody, anti-C5b antibody, anti-C3a antibody, anti-C3b antibody, anti-Factor B antibody, eculizumab, lampalizumab, ravulizumab, anti-properdin antibody in combination with anti-properdin antibody or antigen binding portion thereof the present invention. In another embodiment, the present invention provides a combination comprising of anti-properdin antibody or antigen binding portion(s) thereof and a peptide or a combination comprising anti-properdin antibody or antigen binding portion(s) thereof and a cytokine (preferably interleukin).

Pharmaceutical Compositions

A pharmaceutical composition, containing one or a combination of monoclonal antibodies, or antigen-binding portion(s) thereof, of the present invention formulated together with a pharmaceutically acceptable carrier can be developed. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or to different epitopes on different target antigens or that have complementary activities.

Therapeutic Uses

The anti-properdin antibody or antigen-binding portion thereof or combination according to the current invention or bispecific antibodies or immunoconjugates according to the current invention can be used in therapeutic methods for the treatment of diseases mediated, directly or indirectly, by a component of the alternative complement pathway, and/or by a factor generated following activation of the alternative complement pathway.

In one embodiment of the present invention, the antibodies can be used to inhibit complement activation via the alternative pathway in vivo in subjects, including humans, suffering from disease such as, but not limited to, haematological disorders, chronic renal disorders, ocular inflammatory disorders, various cancers, autoimmune disease and inflammations.

In one embodiment of the present invention, the antibodies can be used to inhibit complement activation via the alternative pathway in vivo in subjects, including humans, suffering from disease or disorders such as, but not limited to, atypical haemolytic uraemic syndrome, haematopoietic stem cell (HSC) transplant-associated TMA (TA-TMA); pregnancy-related HELLP (haemolysis, elevated liver enzymes, low platelets) syndrome; and infection-related or medication-related TMAs, atherosclerosis, paroxysmal nocturnal hemoglobinuria, ischaemia-reperfusion (I/R) organ injury, age-related macular degeneration (AMD), geographic atrophy, ischemia-reperfusion following acute myocardial infarction, Henoch-Schonlein purpura nephritis, immune complex vasculitis, rheumatoid arthritis, arteritis, aneurysm, stroke, cardiomyopathy, sepsis-associated inflammation, haemodialysis-induced inflammation, C3 glomerulopathies, hemorrhagic shock, crush injury, multiple organ failure, hypovolemic shock and intestinal ischemia, transplant rejection, cardiac surgery, percutaneous transluminal coronary angioplasty (PTCA), spontaneous abortion, neuronal injury, Severe acute respiratory syndrome such as Coronavirus Disease 2019 (COVID-19), Middle East respiratory syndrome, viral pneumonia, spinal cord injury, myasthenia gravis, Huntington's disease, amyotrophic lateral sclerosis, multiple sclerosis, Guillain Barre syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, organ transplantation, periodontal disease, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation, and macular degeneration. In vivo inhibition of alternative complement pathway activation is accomplished by administering the antibody to the subject.

The present invention is illustrated with the following non-limiting examples which should not be interpreted as limiting the scope of the invention in any way.

EXAMPLES

The following examples are put forth so as to provide to those of ordinary skills in the art with a disclosure and description of how the methods and antibodies claimed herein are performed. They are intended to purely exemplify only and are not intended to limit the scope of the disclosure. The other antibodies of the present invention can be developed using method as described in provided examples with suitable modifications. Such modifications are well known to the person skilled in the art.

Example 1: Immunization of Mice with Human Properdin Antigen for Binder Generation Four healthy female BALB/c mice were used for the immunization study. Two of them were kept as placebo control in which only PBS was used for the immunization. The other two mice were immunized with human properdin. To demonstrate that the antigenic preparation was capable of inducing anti-properdin antibodies in a highly sensitive species, one rabbit was used as another control for immunization with the same antigen preparation so as to monitor the immune responses at various stages of the immunization processes. All animals were acclimatized for 2 days in the animal research facility before starting the immunization study. Commercially available human properdin protein (Quidel cat #A412) was used for immunization. Protein emulsion was made by mixing 400 µg of human properdin (in 400 µL PBS) and 400 µL of complete Freund's adjuvant (CFA) in a total volume of 800 µL in a siliconized 5 mL screw cap glass vial and vortexing the mixture for 10-15 minutes for emulsion preparation. On day 0, a single dose of 100 µg emulsified protein in a volume of 200 µl (0.5 µg/µL) was injected subcutaneously at four sites on the back of each mouse.

Simultaneously, on day 0, 200 µg of protein emulsion in 400 µL (0.5 µg/µL) was injected subcutaneously at 4 sites on the back of the rabbit.

Incomplete Freund's adjuvant (IFA) was used for the subsequent immunizations (boosters). Four boosters were given to the animals at an interval of 15 days after each immunization. Protein emulsion was made by mixing 200 µg properdin (in 400 µL PBS) and 400 µL of incomplete Freund's adjuvant (IFA). The mixture was vortexed in a siliconized 5 mL screw cap glass vial for 10-15 minutes for emulsion preparation. Each booster dose in mice was administered as single dose of 50 µg of protein emulsion in 200 µL. Booster dose in rabbit was given with 100 µg of protein in 400 µL. Health of the mice and rabbit were monitored daily. To test the antibody titers generated against human properdin antigen, blood was collected from rabbit 4-5 days prior to each booster. Serum was prepared from the blood and used in ELISA for determination of human properdin specific antibodies. Mice were sacrificed 15 days after the 4th booster dose and spleens were collected either for hybridoma generation or for preparing total RNA for phage library generation.

Example 2: Generation of Anti-Properdin Binders after Mouse Immunization

Hybridoma Generation

After fourth booster, the mice were sacrificed and the spleens were removed and chopped in to small pieces and passed through the cell strainer. Subsequently cells were resuspended in cold RPMI (Roswell Park Memorial Institute,) 1640 with 10% FBS and centrifuged at 300 g for 5 minutes. The cell pellet was resuspended in RPMI 1640 with 1% FBS, filtered through a 50 μM syringe filter (BD #340603) and collected by centrifugation.

Polyethylene glycol based protocol was used for hybridoma fusions as described earlier (13, 14). Single cell suspensions were prepared from the spleen of immunized mice as explained above and used for fusion with Sp2/0 myeloma cells (ATCC). Sp2/0 and spleen cells (1:5 ratio) were fused using polyethylene glycol (M.W. 1500, Sigma). Post fusion, the cells were adjusted to a concentration of $0.5 \times 10^6$ cells/mL in RPMI media (Sigma) supplemented with 10% fetal bovine serum (Gibco) and 1× hypoxanthine-aminopterin-thymidine medium (HAT) (Sigma) for selection of hybridomas. Two hundred microliters of this cell suspension was added to each well of 96 well culture plates to generate minipools. After about ten days, culture supernatants were tested in ELISA for binding to purified human native properdin. Properdin reactive minipools were further expanded to 24 well and 6 well plates and T-flasks. The anti-properdin antibody samples from culture supernatants of selected minipools were tested for their binding to human properdin in ELISA.

Based on the results of human properdin reactivity in ELISA, eleven minipools were further short-listed to carry out single cell limiting dilution. For limiting dilution exercise, minipools were plated at a dilution of 1 cell/well in a 96 well culture plate in RPMI media supplemented with 10% fetal bovine serum. Cells were allowed to grow further and expanded to 24 well and 6 well plates and T-flasks. Cell culture supernatants were tested again for their binding to human properdin in ELISA. 104 selected hybridoma clones were grown in serum free production media (BD Cell mAb Medium, Quantum Yield; BD Bioscience) and the culture supernatants were collected for antibody purification by Protein A affinity chromatography. These purified antibody candidates were further tested for their binding affinities in SPR based assay. Four hybridoma derived anti-properdin clones designated 103B2 ($V_H$ SEQ ID 54; $V_L$ SEQ ID 66), 124F9 ($V_H$ SEQ ID 53; $V_L$ SEQ ID 65), 137D4 ($V_H$ SEQ ID 52; $V_L$ SEQ ID 64) and 149F8 ($V_H$ SEQ ID 51; $V_L$ SEQ ID 63) were found to be the best performers from the whole group.

All the 4 clones were found to show good affinities in nM range for human properdin (table 6). Anti-properdin hybridoma mAbs 103B2, 124F9, 137D4 and 149F8 along with other anti-properdin binders coming from phage display library were further humanized and described in example 6.

TABLE 6

Kinetic rate constants of anti-properdin antibodies for human properdin

| Sample ID | ka (1/Ms) | kd (1/s) | $K_D$ (M) |
|---|---|---|---|
| 103B2 | 6.96E+05 | 5.09E−04 | 7.31E−10 |
| 124F9 | 4.50E+05 | 3.62E−03 | 8.04E−09 |

TABLE 6-continued

Kinetic rate constants of anti-properdin antibodies for human properdin

| Sample ID | ka (1/Ms) | kd (1/s) | $K_D$ (M) |
|---|---|---|---|
| 137D4 | 3.53E+05 | 3.02E−04 | 8.54E−10 |
| 149F8 | 1.04E+06 | 7.87E−03 | 7.60E−09 |

ScFv Library Generation by Phage Display Method

For scFv library generation, the immunization protocol as described in example 1 was followed. Spleen from one sacrificed mouse was harvested 15 days after the 4th boost and transferred directly into 10 mL normal saline in a 50 mL polypropylene tube. Spleen was then weighed in diethyl pyrocarbonate (DEPC) treated 1.6 mL centrifuge tube. Total RNA was isolated using Trizol method as follows. Maintaining a temperature of 4° C., the spleen was first minced with surgical blade in a petri dish until a homogenous suspension of spleen cells was formed. Two mL of trizol was added to 90-130 mg of spleen followed by mixing with pipetting and then by vortexing. The process of mincing was repeated until a homogenous mixture of spleen cells and trizol was formed. After that, chloroform (200 μL) was added to the homogenate, mixed and incubated at room temperature for 5 minutes. Homogenate was then centrifuged and supernatant was taken and equal amount of isopropyl alcohol was added for precipitation of RNA. RNA suspension was again centrifuged and pellet was washed with ice cold 70% ethanol. After three washes, the pellet containing total RNA was resuspended in DEPC treated water and left overnight for dissolving at 4° C.

mRNA was then isolated from total RNA as per the manufacturer's instructions (PolyATtract® mRNA Isolation Systems, Cat: Z5300, Promega). Isolated mRNA was used for cDNA preparation using SuperScript™ III first-strand synthesis system (Cat No: 18080051, Invitrogen) following manufacturer's instructions.

Amplification of $V_H$ and $V_L$: Primer sets (Mouse IgG Library Primer Set, Cat No: F2010, Progen) were used for amplifying variable regions of heavy and light chains from cDNA using PCR method following manufacturer's instructions. The amplified $V_H$ and $V_L$ fragments were analyzed on agarose gel and purified from the gel using QIAquick™ gel extraction kit (Qiagen cat no 28706).

Purified $V_H$ and $V_L$ were then cloned sequentially into phagemid vector one after another (pSEX81, Cat No: PR3005, Progen™). In the first ligation, $V_H$ fragment and vector both were restriction digested with NcoI and HindIII, purified from gel and ligated together. Ligation product was transformed into electrocompetent TG1 cells (Cat No: 60502-1, Lucigen™). The $V_L$ fragment and $V_H$ fragment containing vector DNA was again restriction digested with MluI and NotI restriction enzymes, purified and ligated together. The vector containing both the $V_H$ and $V_L$ fragments was transformed into electro competent cells as above. Transformed cells were plated on 2×YT agar plates containing ampicillin (100 μg/mL). A library of transformed cells produced thus was scrapped off from the agar plates and stored in 50% glycerol at −80° C. until further use.

Example 3: ScFv Phage Production from scFv Library and Purification Thereof

Flasks containing 2×YT media with carbenicillin or ampicillin (100 μL/mL) were inoculated with the cells from the glycerol stock of the above described library at the initial concentration of 0.06 $OD_{600}$. Cultures were grown at 37° C. with shaking at 250 rpm till they reach an $OD_{600}$ of upto ~0.4-0.6. Helper phages either, VCSM13 (Agilent, Cat no. 200251) or M13KO7 (GE healthcare, Cat no. 27152401), were then added to the culture at a multiplicity of infection (MOI) of 20, and incubated first without shaking at 37° C. for 40 minutes, followed by another 40 minutes of incubation at 37° C. with shaking. Kanamycin was then added to the media and culture was grown overnight at 26° C. at 150 rpm. Overnight phage culture was centrifuged at 4000 g and cell pellet was discarded. PEG (20%)/NaCl (2.5M) solution at a ratio of 1:5 was added to the supernatant in order to precipitate the phages. Resuspended solution was incubated on ice for 20 minutes followed by centrifugation at 14,000 g for 15 minutes at 4° C. Supernatant was discarded and pellet was resuspended in 1 mL of sterile PBS with 0.01% sodium azide. Phages were stored at 4° C. until further use.

Example 4: Biopanning of Anti-Properdin scFv Expressing Phages

ScFv library ($1\times10^{12}$ pfu) prepared in example 3 was screened for anti-properdin binders. First round of panning against properdin antigen was performed using antigen-immobilized, Immunotubes (Quidel, USA) that were prepared by incubating them with a 5 µg/mL properdin solution in carbonate buffer (0.1 M, pH 9.6) overnight at 4° C. Immunotubes were washed 3 times with PBS and then incubated with phages in PBS for 2 h at 25° C. with constant rotation. The tubes were washed ten times with 4 mL PBS with Tween®20 (0.1%) and subsequently 10 times with PBS. The bound phages were eluted with glycine-HCL pH 2.1 (0.1 M). The eluted phages were rescued by infection of TG1 E. coli cells, plated, and phages produced as described in example 3.

Second and third round of panning were performed on the properdin antigen coated immunotubes in such a manner that output phages from first round of panning ($1\times10^{11}$ CFU) and second ($1\times10^{10}$ CFU) round of panning were used, as input phages for second and third round of panning, respectively. Phages after third round of panning were infected in TG1 cells as mentioned before and phagemid DNA was isolated for scFv cloning in suitable expression vector.

Example 5: Screening of Individual scFv Clones as Soluble Antibody Fragment Proteins The scFv genes from the enriched library produced after 3 rounds of panning was cloned into the expression vector pOPE101 (Progen™, Germany) such that the individual scFv clones could be produced as HIS-tagged fusion products. Both the vector DNA (pOPE101) and phagemid DNA were digested with restriction enzymes (NcoI and NotI) to isolate vector and scFv gene, respectively. Both restriction digested vector and scFv gene were ligated and transformed to TG1 electrocompetent cells. Transformed cells were plated on to the 2×YT agar plates containing carbenicillin antibiotic. Individual clones were picked from the 2×YT agar plates and cultured in 15 mL tube with 5 mL of 2×YT media containing carbenicillin or ampicillin (100 µL/mL) overnight at 32° C. at 200 rpm. Next day, cultures were reinoculated to fresh 2×YT medium containing carbenicillin (100 µg/mL) and glucose (0.1%) at a volumetric ratio of 1:200. Cultures were grown until the $OD_{600}$ reached ~0.6-0.8. After that 1 mM Isopropyl β-D-1-thiogalactopyranoside (IPTG) was added to the culture and grown overnight at 30° C. at 200 rpm. Overnight culture was spun at 10,800 g for 15 minutes and supernatant was removed. Cell pellet was resuspended in $\frac{1}{20}^{th}$ volume of the original culture in buffer (30 mM Tris-Cl, pH 7.0, 20% Sucrose and 1 mM EDTA) and incubated on ice for 30 minutes. Resuspended pellet was centrifuged at 10,800 g for 15 minutes and supernatant was collected as the periplasmic fraction containing the soluble His-tagged scFv. This periplasmic fraction was used in immunoassays to study properdin-binding.

Properdin antigen was coated on polystyrene plates (100 ng/100 µL/well), overnight at 4° C. After washing the plate twice, periplasmic fraction (1/10 v/v) was added and incubated for 1 h at 25° C. Plates were washed 4× with PBST followed by addition of 100 µL (1:5000 v/v) mouse anti-HIS antibody (GE healthcare, Cat no. 27471001) for 1 h. Plates were washed again as described earlier and an HRP-conjugated, goat anti-mouse antibody (Santa Cruz Biotech, Cat no. SC-2031) was added (1:5000) to the plate and incubated for another 1 h at 25° C. At the end of this incubation, the substrate 3, 3', 5, 5'-Tetramethylbenzidine (TMB) was added after four washes. Absorbance at 450 nm was measured with TECAN INFINITE® M1000pro after 5 minute of colour development. An individual clone was considered to be positive, if the OD signal was at least three times above the background (blank wells) (i.e., signal-to-background ratio is >3).

Example 6: Humanization of Hybridoma and Phage Display Library-Derived Murine Anti-Properdin Monoclonal Antibodies Murine binders were humanized by CDR grafting method where framework regions (FR1-4) from the murine antibodies were replaced with the FR regions of the human antibodies. Before grafting, the FRs from the human antibodies were identified on the basis of having the closest match of the murine protein sequence with the human germline antibody. In the present invention, $V_H$ and $V_L$ of the murine binders (SEQ ID No 49 and 62) were humanized and then recombined with $IgG_4$ constant regions to obtain a full-length humanized antibody. Afterwards few amino acid residues in the FR were mutated back to original amino acids present in the murine sequence to regain their functional activity (SEQ ID 55 and 56). (15, 16)

Similarly, $V_H$ (SEQ ID No 50, 51, 52, 53, and 54) and $V_L$ (SEQ ID No 63, 64, 65 and 66) of other murine antibodies were humanized by CDR grafting using their best matching template of human FRs in human germline database to get humanized $V_H$ (SEQ ID No 44, 45, 46, 47 and 48) and $V_L$ (SEQ ID No 57, 58, 60 and 61).

Example 7: Construction of Dual Assembly pZRCIII Hyg Anti-Properdin $IgG_4$ Vectors Chemically synthesized genes including, three Kappa light chain genes [P13(SEQ ID No. 84); P14 LC (SEQ ID No. 85); P15 LC (SEQ ID No. 86)]; and one Lambda light chain gene [E12 LC (SEQ ID No. 87)] with XhoI and KpnI overhangs and five variable regions of heavy chains [P12HC (SEQ ID No. 88), P13HC (SEQ ID No. 89), P14HC (SEQ ID No. 90), P15HC (SEQ ID No. 91) and E12HC (SEQ ID No. 92)] with SalI and ApaI overhangs cloned in pMA/pMK vectors were obtained from Geneart, Germany.

All the four light chains genes (SEQ ID 84, 85, 86 and 87) were isolated from these constructs after digestion with XhoI and KpnI. The pZRCIIIHyg-IgG4 cloning vector was digested with XhoI and KpnI and the linearized vector was ligated with the digested LC genes, individually. pZRCIII vector is prepared as described in patent document WO 2012/046255A2 with constant region of $IgG_4$. The ligation product was transformed in *E. coli* Top10F' and the transformants were scored on the basis of antibiotic resistance. The clones were analysed by restriction digestion and DNA sequencing by Sanger's method. These intermediate vectors containing light chain genes in transcriptional assembly no. 1 were named as pZRCIII Hyg P13LC, pZRCIII Hyg P14LC, pZRCIII Hyg P15LC and pZRCIII Hyg E12LC.

Plasmid DNA prepared from intermediate LC vectors pZRCIII Hyg P13LC, pZRCIII Hyg P14LC, pZRCIII Hyg P15LC and pZRCIII Hyg E12LC were digested with SalI and ApaI to allow the cloning of heavy chain variable region in frame with the $IgG_4$ constant region (SEQ ID No. 93) already existing in the vectors. Heavy chain variable regions containing pMA/pMK plasmid DNA obtained from Geneart were digested with SalI and ApaI. These digested heavy chain variable regions were ligated with the SalI and ApaI digested intermediate vectors in the following combinations—P13 LC (SEQ ID 84) with P12 HC (SEQ ID 88); P13 LC (SEQ ID 84) with P13 HC (SEQ ID 89); P14LC (SEQ ID 85) with P14HC (SEQ ID 90); P15 LC (SEQ ID 86) with P15 HC (SEQ ID 91) and E12 LC (SEQ ID 87) with E12 HC (SEQ ID 92). The ligation product was transformed in *E. coli* Top10F' and transformants were scored based on the kanamycin resistance. The clones were confirmed on the basis of restriction digestion and Sangers sequencing and were named as pZRCIII Hyg P13LC-P12HC (corresponding amino acid sequence of $V_H$ and $V_L$: SEQ ID No. 45 and 57, respectively; referred here in as P12), pZRCIII Hyg P13LC-P13HC (corresponding amino acid sequence of $V_H$ and $V_L$: SEQ ID No. 46 and 57, respectively; referred here in as P13), pZRCIII Hyg P14LC-P14HC (corresponding amino acid sequence of $V_H$ and $V_L$: SEQ ID No. 47 and 60, respectively; referred here in as P14), pZRCIII Hyg P15LC-P15HC (corresponding amino acid sequence of $V_H$ and $V_L$: SEQ ID No. 48 and 61, respectively; referred here in as P15) and pZRCIII Hyg E12LC-E12HC (corresponding amino acid sequence of $V_H$ and $V_L$: SEQ ID No. 44 and 56, respectively; referred here in as P11).

Example 8: Preparation of Dual Vector with $IgG_4$ (GLS) Modified Constant Region It was anticipated that ADCC or CDC effector functions were not required for the anti-properdin mAbs. In order to have least of these effector functions, three mutations namely P329G, M428L and N434S were incorporated in anti-properdin mAbs constructs prepared in above described examples. The mAb candidates, which contains all the three mentioned mutations incorporated in IgG4 constant region were termed as IgG4 (GLS). The constant region of pZRCIII hyg P15LC-P15HC vector construct as described in above example was replaced with IgG4 (GLS) (SEQ ID No.94). To prepare IgG4 (GLS) constant region fragment (SEQ ID NO.96), three mutations, namely P329G, M428L and N434S were incorporated in IgG4 constant region by mutagenic PCR. This purified PCR fragment of ~976 base pair (SEQ ID No.94) with ApaI overhang at 5' and NotI overhangs at 3' termini and pZRCIII Hyg P15 LC-P15HC were digested with restriction enzymes ApaI and NotI. The digestion of vector with ApaI and NotI released IgG4 constant region of ~976 bp and larger fragment of ~12,174 bp, comprising rest of the vector elements. The ~12,174 bp fragment was gel extracted and purified. Similarly, the digested PCR product was purified and ligated with the purified vector fragment. The ligation product was transformed in *E. coli* Top10F'. Transformants were scored on the basis of kanamycin resistance. The ligation product was transformed in *E. coli* Top10F'. Transformants were scored on the basis of kanamycin resistance. The clones were confirmed by restriction digestion and Sanger's sequencing and named as pZRCIII Hyg P15LC-P15HC (IgG4 GLS) [corresponding amino acid sequence of $V_H$ and $V_L$: SEQ ID No. 48 and 61, respectively; corresponding amino acid sequence of Fc region: SEQ ID NO. 96; referred here in as P15 (GLS)].

Example 9: Generation of CHO-S Cell Lines Expressing Humanized Anti-Properdin Antibodies (IgG4 Vectors)

This example describes the generation of transfected pools expressing full-length humanized anti properdin antibodies. Vector constructs as mentioned below were used for transfections.

IgG4 Mammalian Vectors Constructs pZRCIII Hyg P13LC-P12HC, pZRCIII Hyg P13LC-P13HC, pZRCIII Hyg P14LC-P14HC, pZRCIII Hyg P15LC-P15HC, pZRCIII Hyg E12LC-E12HC and pZRCIII Hyg P15LC-P15HC (IgG4 GLS). Plasmids were linearized with AscI restriction enzyme prior to transfection. Chinese Hamster ovary is one of the suitable hosts for expression of monoclonal antibodies. Freestyle CHO-S cells (Invitrogen) were used as host for transfection. Cells (0.5 million/mL) were seeded ~24 hours prior to transfection to have cells in the exponential phase. Transfections were performed by electroporation technique utilizing Neon Transfection system (Invitrogen) following manufacturer's instructions. Post transfection, cells were plated in 24 well cell culture plates containing 1 mL of pre-warmed ProCHO5 Serum Free media (Lonza, Switzerland). Cells were incubated in a humidified incubator at 37° C. in presence of 5% $CO_2$. These transfected pools were selected in the presence of 600 μg/mL of Hygromycin (Invitrogen) in ProCHO5 medium in 24 well culture plate. During the selection process, the cell numbers of all the pools were regularly monitored and regular media exchanges were given. Once the selection was accomplished, cells were further expanded to culture plates, T-flasks and culti-tubes (TPP).

Fed-batch cultures were performed for all selected pools in shake flasks (Corning™) for recombinant protein production of all anti-properdin antibody candidates. Cells were seeded at a density of $0.3 \times 10^6$ cells/mL in Power CHO-2 CD production medium from Lonza. Flasks were incubated in a humidifed Kuhner shaker at 37° C. temperature, 5% $CO_2$ level with shaking speed of 110 RPM. A fixed daily feeding regimen was followed during the culture for all the pools using chemically defined feeds from Hyclone™, GE. Feeding was initiated post 72 hours of culture and continued till the batch was harvested.

The culture supernatants were collected for antibody purification by Protein A affinity chromatography. These purified antibody candidates were further tested in vitro.

Example 10: Determination of Kinetic Rate Constants of Binding of Anti-Properdin Candidates to Properdin Using the Surface Plasmon Resonance Method The kinetic rate constants for the binding of anti properdin candidates to native human purified properdin (Quidel; Cat No: A412) were determined by Surface plasmon resonance-based measurement using the ProteOn™ XPR36 (Bio-Rad).

All binding measurements were performed in PBS (pH 7.4, 0.005% Surfactant P20) at 25° C. To measure the binding rate constants of properdin to the mAbs, human properdin was immobilized onto a GLC sensor chip using amine coupling chemistry. Five dilutions of affinity purified mAbs were prepared and were injected onto the flow cell at a flow rate of 100 µL/minute. The data, in the form of sensograms were analysed using data-fitting programs integrated in the ProteOn™ system. Binding affinities in terms of $K_D$ value are provided for tested antibodies in table 7.

TABLE 7

Kinetic rate constants of humanized anti-properdin antibodies for human properdin

| Sample ID | $k_a$ (1/Ms) | $k_d$ (1/s) | $K_D$ (M) |
|---|---|---|---|
| P11 (humanized version of E12 ) | 4.20E+05 | 8.67E−04 | 2.07E−09 |
| P13 (humanized version of 137D4) | 1.98E+06 | 1.10E−03 | 5.57E−10 |
| P14 (humanized version of 124F9) | 5.40E+05 | 1.51E−03 | 2.81E−09 |
| P15 (humanized version of 103B2) | 9.25E+05 | 1.42E−04 | 1.54E−10 |
| P15 (GLS) (humanized version of 103B2 with GLS in constant region) | 7.92E+05 | 1.28E−04 | 1.62E−10 |

Example 11: Determination of Kinetic Rate Constants of Anti-Properdin Antibodies to Recombinant Human Neonatal Fc Receptor (rhFcRn)

The kinetic constants for the binding of antibodies to recombinant human neonatal Fc receptor (hFcRn) were determined by Surface plasmon resonance-based measurement using the ProteOn™ XPR36 (Bio-Rad). Recombinant rhFcRn receptor (Sino Biologics) was immobilized on a GLC chip following manufacturer's instruction. To measure the association rate constant ($k_a$) and dissociation rate constant ($k_d$), five dilutions of affinity purified antibodies were prepared and injected at a flow rate of 100 µL/minute with an association time of 180s and dissociation time of 600s. Reactions were carried in PBS (pH 6.0, 0.005% Surfactant P20) at 25° C. After each sample run, the chip surface was regenerated using PBS, pH 7.4. The data, in the form of sensograms, was analysed using the data-fitting programs in the ProteOn™ system. The kinetic constants of rhFcRn binding to P15 antibody and P15 (GLS) antibody are shown in table 8. P15 (GLS) was observed to have higher affinity ($K_D$) for rhFcRn.

TABLE 8

Kinetic rate constants of humanized anti-properdin antibodies for hFcRn

| Sample ID | $k_a$ (1/Ms) | $k_d$ (1/s) | $K_D$ (M) |
|---|---|---|---|
| P15 (GLS) (humanized version of 103B2 with GLS in constant region) | 5.02E+05 | 3.29E−02 | 6.60E−08 |
| P15 (humanized version of 103B2) | 2.27E+05 | 1.25E−01 | 5.54E−07 |

Example 12: Determination of Binding of Murine Anti-Properdin mAb to Native Human Properdin by ELISA Wells of F16 Maxisorp™ Immuno module (Nunc™) 96 micro plates were coated by adding 100 µL of purified human factor P (Quidel) at 250 ng/mL overnight at 4° C. humidified chamber. After the coating solution was removed by flicking of the plate, 300 µL of blocking solution-5% skimmed milk in PBST (PBS containing 0.05% Tween® 20) was added to each well for one hour to block the non-specific sites. An hour later, the wells were then washed with wash buffer (0.5% skimmed milk in PBST). Fifty microliters of culture supernatants from each fusion well were collected and diluted with ELISA assay diluent (0.5% skimmed milk in PBS). After one hour of incubation, the wells were washed with wash buffer. The bound murine antibodies were then detected by reaction with horseradish peroxidase (HRP) conjugated goat anti mouse IgG (Santa Cruz Biotechnology, Inc) at a dilution of 1:5000 made in assay diluent. This was followed by 4× washes with PBST. Peroxidase substrate solution containing 0.1% 3,3,5,5 tetramethyl benzidine (Sigma) and 0.0003% hydrogen peroxide (Sigma) was then added to the wells for color development for 30 minutes. The reaction was terminated by addition of 100 µL of 1 M $H_2SO_4$. The OD at 450 nm of the reaction mixture was read with the ELISA reader (Tecan Lifesciences).

Figure 1:
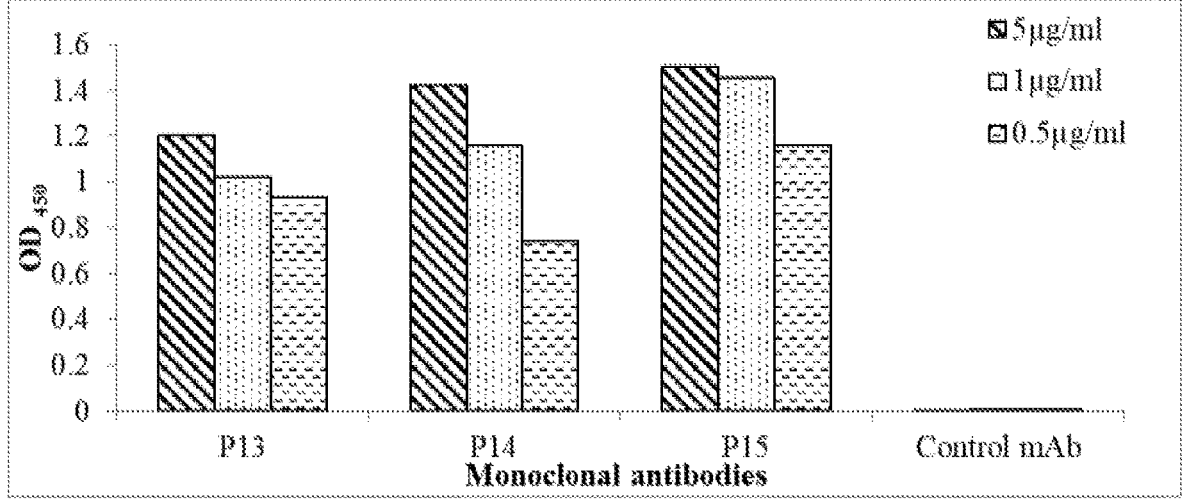
FIG. 1 demonstrates the dose-dependent binding of anti-properdin binders to the native purified human properdin. Tested anti-human properdin mAbs of the present invention showed significant binding to native antigen.

Example 13: Determination of Binding of Humanized Anti-Properdin mAbs to Native Human Properdin by ELISA After humanization, antibody genes were synthesized, transfected, expressed and purified as explained earlier in examples 7 and 9. The purified antibody protein candidates namely P13, P14 and P15 were tested for their binding specificity towards the human properdin antigen. In brief, for testing binding of anti-properdin antibodies to native human properdin, plates were coated with the human properdin antigen (Quidel Cat no. A412) at a concentration of 50 ng/50 µL/well in carbonate buffer (0.1M, pH 9.6). Plates were incubated overnight at 4° C. followed by washing and blocking with 5% skimmed milk (1×PBS, pH-7.4). Blocked plates were washed with 1×PBS and purified mAbs were then added to the antigen coated wells (0.5-1 µg/100 µL/well) and incubated for 1 hour at 37° C. under shaking condition. Plates were washed thrice with PBST (0.1% Tween®20 in 1×PBS, pH-7.4). Horse radish peroxidase (HRP)-conjugated, goat anti-human IgG (SantaCruz, Cat no. sc2453) was added to each well at 1:10000 dilution (100 µL/well) followed by incubation for 1 h at 37° C. under shaking condition. Plates were washed with PBST (0.1% Tween®20 in 1×PBS, pH-7.4) followed by 2 washes with 1×PBS. Subsequently, o-phenylenediamine dihydrochloride (OPD)/$H_2O_2$ (100 µL/well) was added to the wells followed by stopping the reaction after 15 minute with 100 µL of 1N $H_2SO_4$ and reading the plate at 450 nm. The clones were considered positive (FIG. 1) for properdin binding, if signal to background ratio is >3 times. The positive clones were tested for their affinities in SPR (surface plasmon resonance) and functional activities were compared in the haemolytic assay.

Example 14: Haemolytic Assay for the Shortlisted Anti-Properdin Candidates to Determine The Functional Activity of the Individual mAbs Anti-properdin antibody candidates were examined for their ability to inhibit the alternative complement pathway using the rabbit erythrocytes lysis assay in which the classical complement pathway has been blocked using EGTA and the lysis of rabbit RBCs was carried out only by the alternative pathway in NHS with the formation of MAC on the surface of rabbit RBCs (17). Desired anti-properdin antibody candidates are expected to inhibit this alternative pathway to varying degrees depending upon their affinity to properdin and their site of binding. Anti-properdin antibody candidates developed according to the current invention are therefore expected to prevent the lysis of rabbit RBCs in the presence of human serum. The percent inhibition of hae-molysis at a given antibody dilution/concentration for a given monoclonal antibody was calculated for each antibody and at all dilutions tested and compared between individual candidates.

Figure 2A:
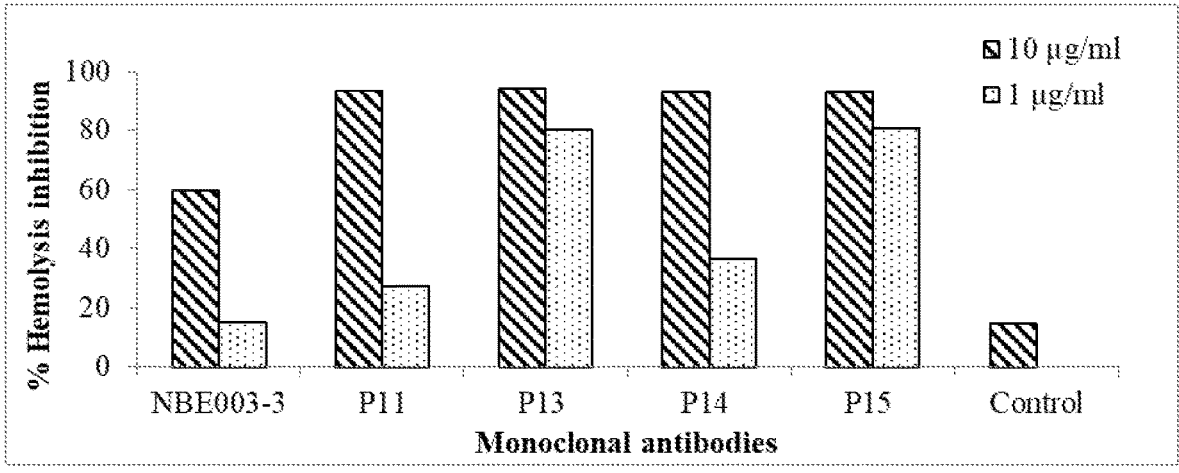
FIGS. 2a & 2b demonstrate that the anti-human properdin mAbs of the current invention inhibit the human alternate complement mediated rabbit red blood cells (RBCs) lysis. This lysis was almost completely inhibited by each of the tested anti-properdin mAbs. The isotype control mAb was used as the negative control and showed only negligible inhibition of lysis.
Figure 2B:
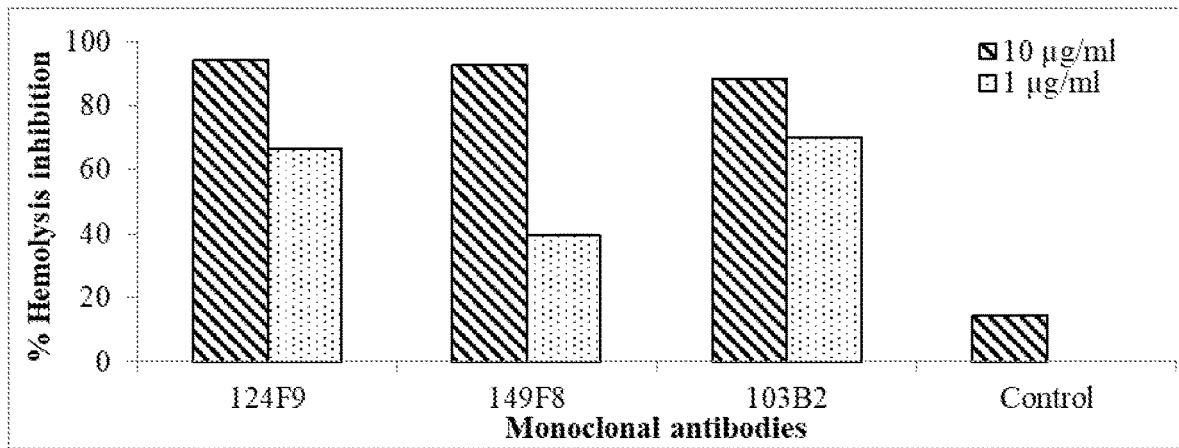

Fresh rabbit RBCs were collected in the Alsever's solution and washed 5 times with assay buffer (150 mM NaCl, 20 mM HEPES, 25 mM MgCl$_2$ and 20 mM EGTA). Washed RBCs were resuspended in the assay buffer at the required concentration. Different concentrations of each of the anti-properdin antibody samples (Humanised anti-properdin antibodies—NBE003-3, P11, P13, P14, P15 and murine anti-properdin antibodies—124F9, 149F8, 103B20) were incubated with the human serum (25%) for 30 minute at 37° C. These were then added to fixed number of rabbit erythrocytes and incubated further for 50 minutes at 37° C. The treated cells were then centrifuged and supernatants were measured for released haemoglobin by measuring absorbance at 405/595 wavelength. The percentage reduction in the released haemoglobin in the presence of anti-properdin antibodies of the current invention or negative antibody control (IgG2) was calculated against lysis obtained by incubating rabbit RBCs with human serum without any test antibody. This lysis was considered as 100%. As shown in the FIG. 2a (for humanized anti-properdin monoclonal antibodies) & 2b (murine anti-for properdin monoclonal antibodies), all the tested anti-properdin mAbs inhibited the human serum-mediated haemolysis of rabbit RBCs in a dose dependent manner. These results show that anti-properdin monoclonal antibodies prepared according to the present invention can significantly inhibit the alternative complement pathway.

Example 15: Cross-Reactive Haemolytic Assay of Shortlisted Anti-Properdin Candidates to Monkey Serum Anti-properdin antibody candidates were examined for their ability to cross-react with monkey properdin by blocking the activity of complement in monkey serum in a rabbit RBC lysis assay. Functional assay was performed essentially as described in Example 14 using monkey serum instead of NHS. The anti-properdin mAbs of the present invention that have the ability to cross-react with monkey properdin are expected to prevent the lysis of rabbit RBCs by blocking the MAC formation mediated by the alternative complement pathway.

Figure 3A:
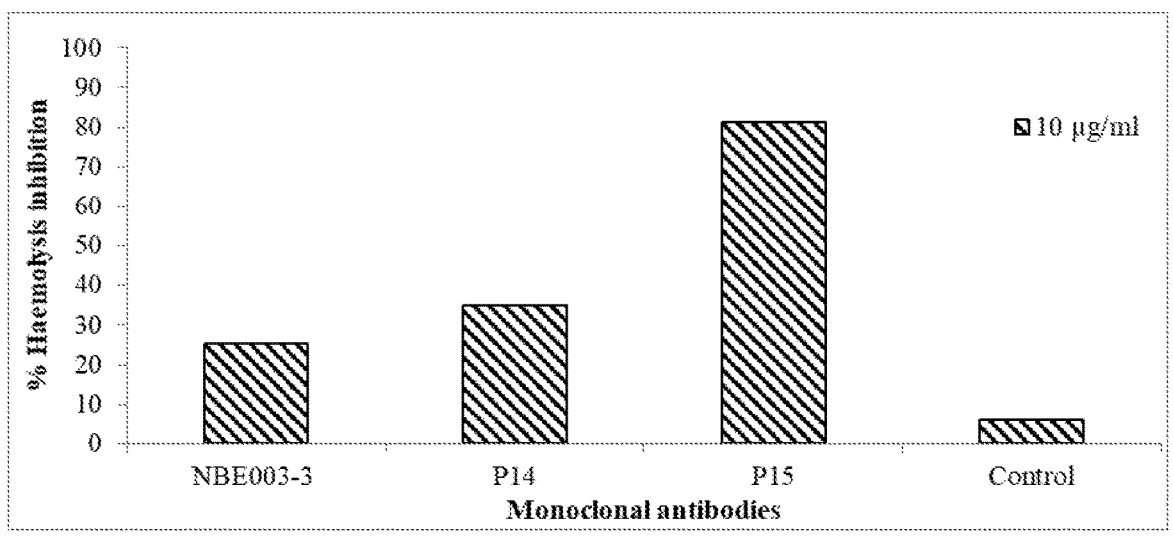
FIG. 3a demonstrates the cross-reactivity of anti-properdin mAbs with monkey properdin in its serum. All tested humanized anti-human properdin mAbs of the current invention were able to inhibit lysis of rabbit RBCs mediated by monkey alternate complement system from monkey serum.

Fresh rabbit RBCs were collected in the Alsever's solution and washed 5 times with assay buffer (150 mM NaCl, 20 mM HEPES, 25 mM MgCl$_2$ and 20 mM EGTA). Washed RBCs were resuspended in the assay buffer at the required concentration. Different concentrations of each of the anti-properdin antibody mAbs (NBE003-3, P14 and P15) were incubated with the monkey serum (25%) for 30 minute at 37° C. These were then added to fixed number of rabbit erythrocytes and incubated further for 50 minutes at 37° C. The treated cells were then centrifuged and supernatants were measured for released haemoglobin by measuring absorbance at 405/595 wavelength. The percentage reduction in the released haemoglobin in the presence of anti-properdin antibodies of the present invention was calculated against erythrocyte lysis observed in the presence of monkey serum without any antibody. This lysis was considered as 100%. As shown in the FIG. 3a, anti-properdin antibodies of the present invention prevent the haemolysis of rabbit RBCs in the presence of monkey serum.

Figure 3B:
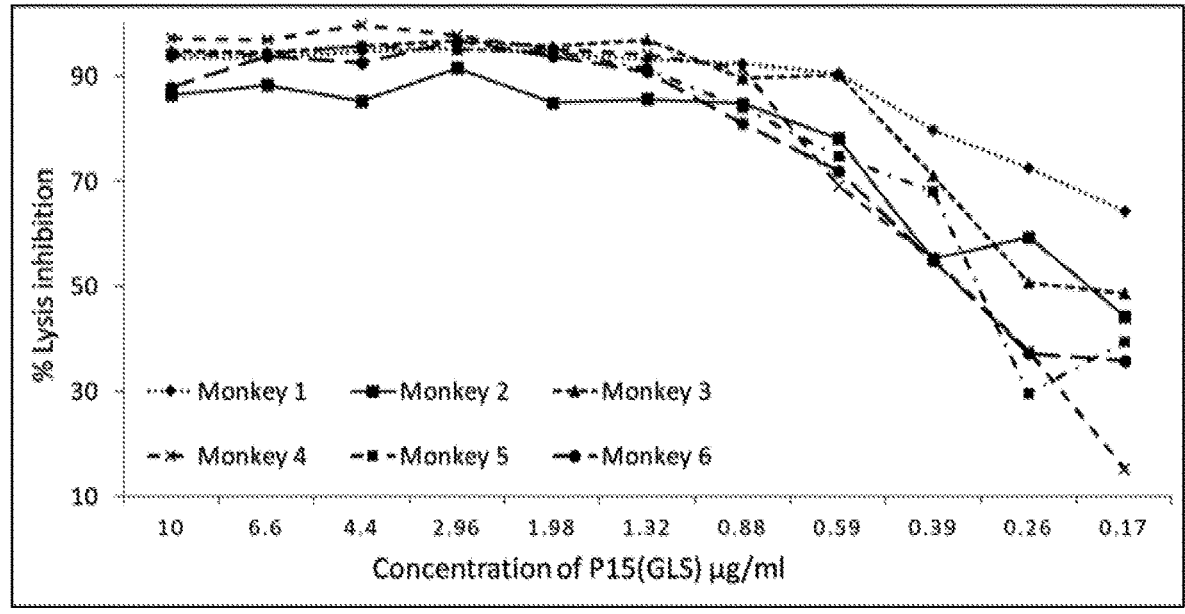
FIG. 3b demonstrates the haemolysis inhibition activity of anti-properdin mAb P15 (GLS) in six different monkeys. P15 (GLS) was able to inhibit 85-95% lysis of rabbit RBCs mediated by monkey serum in different monkeys.

Anti properdin antibody candidate P15 (GLS) was also examined for its ability to block complement activity in six different monkey serum. The functional assay was performed as described above using rabbit RBCs and serum from six different monkeys. Lysis inhibition was performed using P15 (GLS) at concentration ranging from 10-0.17 µg/ml. As shown in FIG. 3b, anti-properdin antibody of the present invention, P15 (GLS), prevents the haemolysis of rabbit RBCs in the presence of monkey serum. These results confirmed cross-reactivity of monoclonal antibodies with monkey properdin in its serum. The antibodies of the present invention can also be used directly in animal pharmacology and toxicology studies required during drug development without requiring the use of surrogate antibodies.

Example 16: LPS AP Assay for the Selected Candidates to Determine the Functionality of Anti-Properdin Antibodies Alternative complement pathway in serum can be activated by lipopolysaccharide (LPS) from *Salmonella typhosa* (18). Purified LPS can be used to produce alternative complement pathway mediated MAC formation on the ELISA plate surface (19, 20). The ability of anti-properdin antibody candidates of the current invention to inhibit such MAC formation was tested in this assay system.

Microtitre plate (Nunc™) was coated with LPS from *S. typhosa* (Sigma, cat No: L6386), at 2 µg/50 µL/well in PBS. Plate was then incubated overnight at 4° C. After washing, plate was washed 2 times with 1×PBS and blocked for 1 h with 1% BSA (300 µL/well) at 37° C. Meanwhile, NHS (12.5% in HEPES buffer (20 mM) containing 150 mM NaCl, 20 mM MgCl$_2$ and 6.25 mM EGTA) was pre-incubated, with either anti-properdin mAb (P14, P15 or P15 (GLS)), or isotype control antibody at 37° C., under shaking condition, for 1 h. This pre-incubated mixture of serum and antibody was then transferred to the above described, washed, LPS-coated plate and incubated for 1 h to allow for the activation of the alternative complement pathway and MAC formation. Plate was washed 3 times with 1×PBS and mouse anti-human MAC antibody at 1:5000 dilution (volume) was added and incubated for 60 minutes at 37° C. Plate was again washed 3 times with 1×PBS and 100 µL (1:10000 v/v) HRP-conjugated anti-mouse IgG (Santa Cruz, Cat no. sc-58935) was added to each well and incubated for 60 minutes at 37° C. Plates were finally washed 6 times with 1×PBS and ELISA colour was developed after adding TMB/H$_2$O$_2$ for 15 minutes and OD taken at 450 nm after stopping the reaction using 100 µL/well 1N H$_2$SO$_4$.

Figure 4:
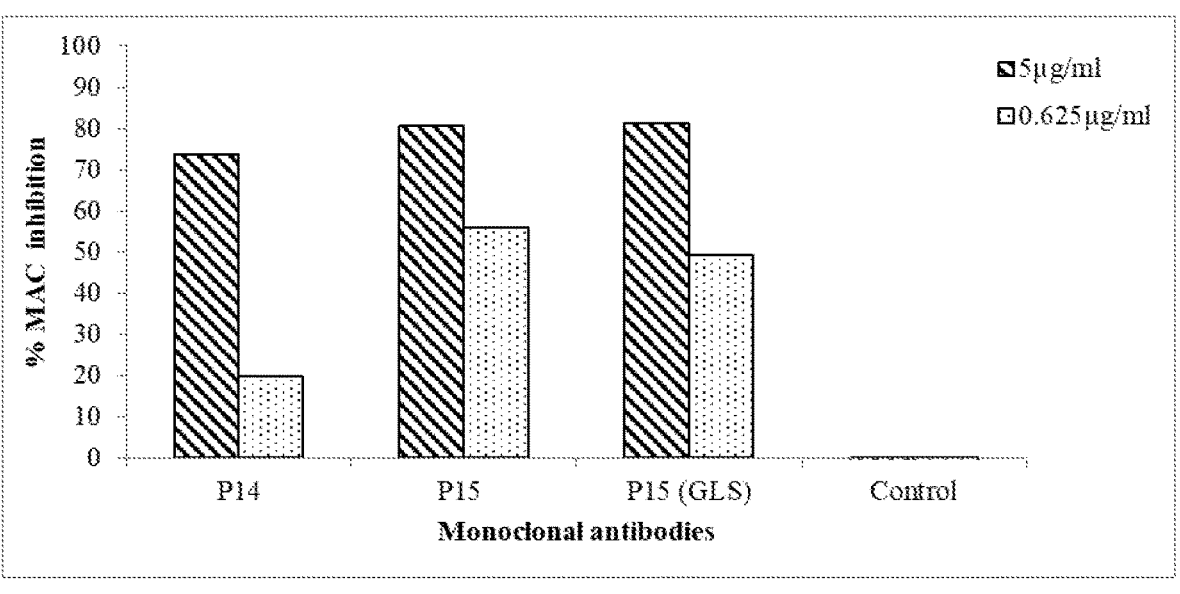
FIG. 4 demonstrates the dose-dependent inhibition of LPS-induced complement activation by all the tested mAbs of the current invention. All tested mAbs effectively inhibited complement activation mediated by normal human

The assay demonstrated (FIG. 4) that the anti-properdin mAbs of the current invention (P14, P15 and P15 (GLS)) inhibited that component of the LPS-mediated complement pathway in NHS that remained functional in the presence of EGTA; and this was observed to be in a dose dependent manner.

Example 17: Human RBCs Lysis Inhibition Assay Using Anti-CD55 and Anti-CD59

In a normal healthy individual, the serum does not cause the lysis of self RBCs. This is despite the constitutively active nature of the alternative complement pathway and possible because of the presence of natural complement inhibitory factors present both in serum (e.g., Factor H) and on the surface of cells that come in contact with plasma (e.g., CD55 and CD59). The absence of these inhibitory factors is known to cause severe disease pathology (e.g., PNH and aHUS etc.).

Haemolytic assays using RBCs and serum obtained from normal healthy individuals were setup on the lines of those described above for the rabbit RBC lysis assay, except for the fact that the regulation of complement pathway was inhibited by the addition of anti-CD55 and anti-CD59 antibodies. In the presence of these inhibitors, the serum from an otherwise normal healthy volunteers were able to lyse his/her own RBCs in vitro, due to the removal of inhibition and activation of complement pathway.

Reported (21) study demonstrating the similar mechanism of complement regulation was followed for experiments described herein with minor changes. In brief, normal human RBCs (25 million cells per reaction) were added to a solution (100 μL final volume) composed of gelatin veronal buffer (GVB++) (Sigma-Aldrich) supplemented with $Mg^{2+}$ (25 mM)-EGTA (20 mM), and anti-human CD55 (clone BRIC216) and anti-human CD59 (clone MEM-43) antibodies (final concentration: 10 μg/mL as shown in FIG. 5; AbD Serotec) incubated for 1 hour at RT. NHS (75 μL) with control mAb or with anti-properdin antibody of the current invention (both at 5 μg/mL) was added to the RBCs to make the final reaction volume to 200 μL and incubated for 4 h at 37° C. Reaction mixtures were centrifuged (1500 rpm for 5 minute) to pellet down non-lysed erythrocytes. Degree of erythrocyte lysis was measured by OD at 405/595 nm of an aliquot of the recovered supernatant. Percentage lysis inhibition was calculated by normalizing the OD value to that of lysed erythrocytes (preincubated with anti-CD55 and anti-CD59 antibodies) in the presence of NHS. This lysis in the absence of any anti-properdin antibody or control antibody was considered as 100% lysis. The humanized antibodies of the current invention (P14, P15 and P15 (GLS)) were able to significantly inhibit the lysis of human RBCs in PNH like conditions as shown in FIG. 5.

Example 18: Pronase Treated Human RBCs Lysis Inhibition Assay

The natural regulation of complement with regulators expressing on the cell surface of normal cells can also be eliminated by treatment of cells with proteases like pronase (22). Proteases have been used earlier to modify normal human RBC to convert them into complement sensitive PNH-like cells. Haemolytic assays were performed as described previously using pronase-treated, normal human RBCs. Pronase treatment leads to the lysis of normal human RBCs with their own serum because of activation of alternate complement pathway.

Normal human erythrocytes (25 million cells per reaction) were added to a solution (100 μL final volume) composed of gelatin veronal buffer (GVB++) (Sigma-Aldrich) supplemented with $Mg^{2+}$ (25 mM)-EGTA (20 mM). These RBCs were treated with pronase enzyme (5 mg/mL) for 30 minutes at 37° C. NHS (50 μL) pre-incubated with or without anti-properdin antibody at different concentrations (5, 2.5 and 1.25) for 30 minute was added to the pronase-treated RBCs to make a final reaction volume of 200 μL and incubated for 4 h at 37° C. Reaction mixtures were centrifuged (1500 rpm) for 5 minutes to pellet non-lysed erythrocytes. Degree of RBCs lysis was measured by OD at 405/595 nm of an aliquot of the recovered supernatant. Percentage lysis inhibition was calculated by normalizing the OD value to that of lysed erythrocytes (pronase treated) in the presence of NHS. This lysis in the absence of any anti-properdin antibody or control antibody was considered as 100% lysis. Anti-properdin mAbs of the current invention (P14, P15 and P15 (GLS)) were able to inhibit the complement-mediated lysis of pronase treated human RBCs in the presence of NHS as shown in FIG. 6.

Example 19: Determination of the Efficacy of Anti Properdin Antibodies in a Mouse Model Of LPS Induced Lung Injury Intratracheal LPS instillation has been known to induce lung injury with the elevation of cytokines in the bronchoalveolar lavage (BAL) fluid. Decrease in the cytokine due to any therapeutic administration is considered to be efficacious. For the experiment Balb/c mice were weighed and randomized. The mice were randomized into four groups. One group was kept as sham control to determine the increase in cytokine levels due to the procedure of intratracheal instillation. While in another group the anti-properdin surrogate (rabbit anti-mouse properdin) sera was administered by i.v. route at a concentration of 400 μg/20 g mice. The rabbit anti-mouse-properdin antibody used herein is referred to as ZAP surrogate. In the vehicle control (disease control) only placebo was administered at a similar volume to the anti-properdin surrogate sera by the i.v. route. An animal group without any disease induction was also studied to determine any change in the basal cytokine levels. Post the administration of surrogate anti-properdin sera or placebo, LPS (Sigma) was intratrachealy instilled in each mice. The animals were humanely sacrificed 6 hours after the LPS instillation and the BAL washings was collected from each mice and evaluated for the levels of TNF-α and IL-6 using ELISA. Anti-properdin mAbs (ZAP surrogate) were able to decrease inflammatory cytokines in the bronchoalveolar lavage (BAL) fluid as shown in FIGS. 7 and 8. These results demonstrate that anti-properdin treatment is efficacious in treating lung injury. For both TNF-α (555268) and IL-6 (555240) ELISA, kits manufactured by BD biosciences was used. The procedures was undertaken as per the kit instructions. The absorbance was read at 450 nm with a correction at absorbance at 570 nm.

List of Nucleotide and Amino Acid Sequences Used in the Present Invention:

```
SEQ ID No. 84: P13 light chain
ATGGGCTGGTCCTGCATCATTCTGTTTCTGGTGGCTACCGCCACCGGCGTGCACTCTGATATCGTGATGACCCAGTCT

CCTGACAGCCTGGCTGTGTCTCTGGGCGAGAGAGCCACCATCAACTGCAAGTCCTCTCAGTCCCTGCTGTACTCCTCC

AACCAGAAGAACTACCTGGCCTGGTATCAGCAGAAGCCCGGACAGCCTCCTAAGCTGCTGATCTACTGGGCCTCCACC

AGAGAATCTGGCGTGCCAGATAGATTCTCCGGCTCTGGCTCTGGCACCGACTTTACCCTGACAATCAGCTCTCTGCAG

GCCGAGGATGTGGCCGTGTACTACTGCCAGCAGTACTACAGCTACCCCTACACCTTTGGCGGAGGCACCAAGCTGGAA
```

-continued

ATCAAGAGAACCGTGGCCGCTCCTTCCGTGTTCATCTTCCCACCATCTGACGAGCAGCTGAAGTCCGGCACAGCTTCT

GTCGTGTGCCTGCTGAACAACTTCTACCCTCGGGAAGCCAAGGTGCAGTGGAAGGTGGACAATGCCCTGCAGTCCGGC

AACTCCCAAGAGTCTGTGACCGAGCAGGACTCCAAGGACTCTACCTACAGCCTGTCCTCCACACTGACCCTGTCTAAG

GCCGACTACGAGAAGCACAAGGTGTACGCCTGTGAAGTGACCCACCAGGGACTGTCTAGCCCCGTGACCAAGTCTTTC

AACAGAGGCGAGTGCTAATGA

SEQ ID No. 85: P14 light chain
ATGGGCTGGTCCTGCATCATTCTGTTTCTGGTGGCTACCGCCACCGGCGTGCACTCTGATATCGTGATGACCCAGTCT

CCTCTGAGCCTGTCTGTGACACCTGGCCAGCCTGCCTCCATCTCTTGCAAGTCATCTCAGTCCCTGCTGGACATCAAC

GGCAAGACCTACCTGAACTGGTATCTGCAGAAGCCCGGCCAGTCTCCACAGCTGCTGATCTACCTGGTGTCCAAGCTG

GATTCTGGCGTGCCCGACAGATTTTCCGGCTCTGGCTCTGGCACCGACTTCACCCTGAAGATTTCCAGAGTGGAAGCC

GAGGACGTGGGCGTGTACTACTGTTGGCAGGGCACCCACTTTCCATACACCTTCGGCCAGGGCACCAAGGTGGAAATC

AAGAGAACCGTGGCCGCTCCTTCCGTGTTCATCTTCCCACCATCTGACGAGCAGCTGAAGTCCGGCACAGCTTCTGTC

GTGTGCCTGCTGAACAACTTCTACCCTCGGGAAGCCAAGGTGCAGTGGAAGGTGGACAATGCCCTGCAGTCCGGCAAC

TCCCAAGAGTCTGTGACCGAGCAGGACTCCAAGGACTCTACCTACTCTCTGTCCTCCACACTGACCCTGTCCAAGGCC

GACTACGAGAAGCACAAGGTGTACGCCTGTGAAGTGACCCACCAGGGACTGTCTAGCCCCGTGACCAAGTCTTTCAAC

AGAGGCGAGTGCTAATGA

SEQ ID No. 86: P15 light chain
ATGGGCTGGTCCTGCATCATTCTGTTTCTGGTGGCTACCGCCACCGGCGTGCACTCTGATATCCAGATGACCCAGTCT

CCTTCCAGCCTGTCTGCCTCTGTGGGCGACAGAGTGACCATCACCTGTCTGGCTTCTCAGACCATCGGCACCTGGCTG

GCCTGGTATCAGCAGAAGCCTGGAAAGGCCCCTAAGCTGCTGATCTACGCTGCCACATCTCTGGCCGATGGCGTGCCA

TCTAGATTCTCTGGCTCTGGCTCCGGCACCGACTTTACCCTGACAATCAGTTCCCTGCAGCCTGAGGACTTCGCCACC

TACTACTGCCAGCAGCTGTACTCTACCCCTTGGACCTTTGGCGGAGGCACCAAGCTGGAAATCAAGAGAACCGTGGCC

GCTCCTTCCGTGTTCATCTTCCCACCATCTGACGAGCAGCTGAAGTCTGGCACCGCTTCTGTCGTGTGCCTGCTGAAC

AACTTCTACCCTCGGGAAGCCAAGGTGCAGTGGAAGGTGGACAATGCCCTGCAGTCCGGCAACTCCCAAGAGTCTGTG

ACCGAGCAGGACTCCAAGGACTCTACCTACAGCCTGTCCTCCACACTGACCCTGTCTAAGGCCGACTACGAGAAGCAC

AAGGTGTACGCCTGTGAAGTGACCCACCAGGGACTGTCTAGCCCCGTGACCAAGTCTTTCAACAGAGGCGAGTGCTAA

TGA

SEQ ID No. 87: E12 light chain
ATGGGCTGGTCCTGCATCATTCTGTTTCTGGTGGCTACCGCCACCGGCGTGCACTCTCAGTCTGTTTTGACTCAGCCT

CCTTCCGTGTCTGCCGCTCCTGGCCAGAAAGTGACCATCTCTTGCTCCGGCTCCTCCTCCAACATCGGCAACAACTAT

GTGTCTTGGTACGTGCAGCTGCCCGGCACAGCTCCTAAGCTGCTGATCTACGACAACAACAAGCGGTTCTCCGGCGTG

CCCGACAGATTCTCTGGCTCTAAGTCTGGCACCAGCGCTACCCTGGGAATCACAGGATTGCAGACAGGCGACGAGGCC

GATTACTACTGTGGCGCTTGGGACGGCTCTCTGAGGGAAGCTGTTTTTGGCGGAGGCACCAAAGTGACCGTGCTGAGA

GCTGCTGGACAGCCTAAAGCCGCTCCTAGCGTGACCCTGTTTCCTCCATCTTCTGAGGAACTGCAGGCCAACAAGGCT

ACCCTCGTGTGCCTGATCTCTGACTTTTACCCTGGCGCTGTGACCGTGGCCTGGAAGGCTGATAGTTCTCCTGTGAAG

GCCGGCGTGGAAACCACCACACCTTCCAAGCAGTCCAACAACAAATACGCCGCCTCCTCCTACCTGTCTCTGACCCCT

GAACAGTGGAAGTCCCACCGGTCCTACTCTTGCCAAGTGACCCATGAGGGCTCCACCGTGGAAAAGACAGTGGCCCCT

ACCGAGTGCTCCTAATGA

SEQ ID No. 88: P12 heavy chain variable region
ATGGGCTGGTCCTGCATCATTCTGTTTCTGGTGGCTACCGCCACCGGCGTGCACTCTCAGGTTCAGTTGCAACAGTCT

GGCCCTGAACTCGTCAGACCCGGCGTGTCCGTGAAGATCAGCTGTAAAGGCTCCGGCTACACCTTCACCGACTACGCC

ATGCACTGGGTCAAGCAGTCTCACGCCGAGTCTCTGGAATGGATCGGCCTGATCTCTACCTACTACGGCGACGCCGGC

TACAACCAGAAGTTCAAGGATAAGGCCACAATGACCGTGGACATCTCCTCCTCCACCGCCTACCTGGAACTGGCTAGA

-continued

```
CTGACCTCTGAGGACTCCGCCATCTACTACTGCGCCAGAGCCGACTCCTCTGGCAACTTCTTTGATTACTGGGGCCAG

GGCACCCTGGTCACCGTTTCTAGTGCTTCCACAAAGGGCCC
```

SEQ ID No. 89: P13 heavy chain variable region
```
ATGGGCTGGTCCTGCATCATTCTGTTTCTGGTGGCTACCGCCACCGGCGTGCACTCTGAAGTTCAGTTGCAGCAGTCT

GGCCCCGAGCTTGTGAAACCTGGCGCCTCTGTGAAGATGTCCTGCAAGGCCTCTGGCTACACCTTCGCTCACAACTGG

ATTCACTGGGTCAAGCAGAAGCCAGGCCAGGGACTTGAGTGGATCGGCTACATCAACCCTGGCACCGACTACACCGAG

TACTCCCAGAGATTCAAGGGCAAAGCTACCCTGACCTCCGACAAGTCCTCCTCCACCGCTTACATGGAACTGTCCAGC

CTGACCTCTGAGGACTCCGCCGTGTACTACTGCGCCAGAAGAAAGCTGTACGGCAACTTCGTGGACTACGCCATGGAT

TATTGGGGCCAGGGCACCCTGGTTACCGTGTCTGCTGCTTCTACAAAGGGCCC
```

SEQ ID No. 90: P14 heavy chain variable region
```
ATGGGCTGGTCCTGCATCATTCTGTTTCTGGTGGCTACCGCCACCGGCGTGCACTCTCAGGTTCAGTTGCAAGAGTCT

GGCCCTGGCCTGGTCAAGCCTTCTCAGACCCTGTCTCTGACCTGCACCGTGTCCGGCTATTCCATCACCTCCGGCTAC

TACTGGAACTGGATCAGACAGCACCCCGGCAAAGGCCTGGAATGGATCGGCTACATCTCTTACGACGGCGGCAACAAG

TACAACCCCAGCCTGAAGTCCAGAGTGACCATCTCTCGGGACACCTCCAAGAACCAGTTCTCCCTGAAGCTGTCCTCT

GTGACCGCTGCCGATACCGCCGTGTACTACTGTGCCCGCGATCTGGATGGCTACGAGTCTATGGATTATTGGGGCCAG

GGCACCTCCGTGACCGTGTCCTCTGCTTCTACAAAGGGCCC
```

SEQ ID No. 91: P15 heavy chain variable region
```
ATGGGCTGGTCCTGCATCATTCTGTTTCTGGTGGCTACCGCCACCGGCGTGCACTCTCAGGTTCAGTTGCAAGAGTCT

GGCCCTGGCCTGGTCAAGCCTTCTCAGACCCTGTCTCTGACCTGCACCGTGTCCGGCTACTCCATCACCTCCACCTAC

TACTGGAACTGGATCAGACAGCACCCCGGCAAAGGCCTGGAATGGATCGGCTACATCTCCTACGACGGCACCAACAAG

TACAACCCCAGCCTGAAGTCCAGAGTGACCATCTCTCGGGACACCTCCAAGAACCAGTTCTCCCTGAAGCTGTCCTCT

GTGACCGCTGCCGATACCGCCGTGTACTACTGCGCCAGAGATGACTACGACAGATCCCCTTGGTTTGCCTATTGGGGC

CAGGGCACACTGGTCACCGTTTCCAGTGCTTCTACCAAGGGCCC
```

SEQ ID No. 92: E12 heavy chain variable region
```
ATGGGCTGGTCCTGCATCATTCTGTTTCTGGTGGCTACCGCCACCGGCGTGCACTCTCAGGTTCAGTTGCAACAGTCT

GGCCCTGAACTCGTCAGACCCGGCGTGTCCGTGAAGATCAGCTGTAAAGGCTCCGGCTACACCTTCACCGATTACGCC

CTGCACTGGGTCAAGCAGTCTCACGCTGAGTCTCTGGAATGGATCGGCGTGATCTCCACCTACTACGGCGACGCCTCC

TACAACCAGAAGTTCAAGGACAAGGCCACAATGACCGTGGACATCTCCTCCTCCACCGCCTACCTGGAACTGGCTAGA

CTGACCTCTGAGGACTCCGCCATCTACTACTGCGCCAGAGATGGCTACCTGGATTATTGGGGCCAGGGCACACTGGTC

ACCGTGTCCTCTGCTTCTACAAAGGGCCC
```

SEQ ID No. 93: IgG<sub>4</sub> heavy chain constant region
```
GGGCCCCTCCGTGTTCCCTCTGGCCCCTTGCTCCCGGTCCACCTCCGAGTCTACCGCCGCTCTGGGCTGCCTGGTGAA

AGACTACTTCCCCGAGCCCGTGACCGTGTCCTGGAACTCTGGCGCCCTGACCAGCGGCGTGCACACCTTCCCTGCCGT

GCTGCAGTCCTCCGGCCTGTACTCCCTGTCCTCCGTGGTGACCGTGCCCTCCTCAGCCTGGGCACCAAGACCTACAC

CTGTAACGTGGACCACAAGCCCTCCAACACCAAGGTGGACAAGCGGGTGGAATCTAAGTACGGCCCTCCCTGCCCCCC

CTGCCCTGCCCCTGAATTTCTGGGCGGACCTTCCGTGTTCCTGTTCCCCCCAAAGCCCAAGGACACCCTGATGATCTC

CCGGACCCCCGAAGTGACCTGCGTGGTGGTGGACGTGTCCCAGGAAGATCCCGAGGTGCAGTTCAATTGGTACGTGGA

CGGCGTGGAAGTGCACAACGCCAAGACCAAGCCCAGAGAGGAACAGTTCAACTCCACCTACCGGGTGGTGTCTGTGCT

GACCGTGCTGCACCAGGACTGGCTGAACGGCAAAGAGTACAAGTGCAAGGTGTCCAACAAGGGCCTGCCCTCCAGCAT

CGAAAAGACCATCTCCAAGGCCAAGGGCCAGCCCCGCGAGCCCCAGGTGTACACCCTGCCCCCTAGCCAGGAAGAGAT

GACCAAGAACCAGGTGTCCCTGACCTGTCTGGTGAAAGGCTTCTACCCCTCCGATATCGCCGTGGAATGGGAGTCCAA
```

-continued

```
CGGCCAGCCCGAGAACAACTACAAGACCACCCCCCCTGTGCTGGACTCCGACGGCTCCTTCTTCCTGTACTCTCGGCT

GACCGTGGACAAGTCCCGGTGGCAGGAAGGCAACGTGTTCTCCTGCTCCGTGATGCACGAGGCCCTGCACAACCACTA

CACCCAGAAGTCCCTGTCCCTGAGCCTGGGCAAGTGATGA
```

SEQ ID No. 94: IgG₄ (GLS) modified heavy chain constant region
```
GGGCCCCTCCGTGTTCCCTCTGGCCCCTTGCTCCCGGTCCACCTCCGAGTCTACCGCCGCTCTGGGCTGCCTGGTGAA

AGACTACTTCCCCGAGCCCGTGACCGTGTCCTGGAACTCTGGCGCCCTGACCAGCGGCGTGCACACCTTCCCTGCCGT

GCTGCAGTCCTCCGGCCTGTACTCCCTGTCCTCCGTGGTGACCGTGCCCTCCTCCAGCCTGGGCACCAAGACCTACAC

CTGTAACGTGGACCACAAGCCCTCCAACACCAAGGTGGACAAGCGGGTGGAATCTAAGTACGGCCCTCCCTGCCCCCC

CTGCCCTGCCCCTGAATTTCTGGGCGGACCTTCCGTGTTCCTGTTCCCCCCAAAGCCCAAGGACACCCTGATGATCTC

CCGGACCCCCGAAGTGACCTGCGTGGTGGTGGACGTGTCCCAGGAAGATCCCGAGGTGCAGTTCAATTGGTACGTGGA

CGGCGTGGAAGTGCACAACGCCAAGACCAAGCCTAGAGAGGAACAGTTCAACAGCACCTACAGAGTGGTGTCCGTGCT

GACCGTGCTGCACCAGGATTGGCTGAACGGCAAAGAGTACAAGTGCAAGGTGTCCAACAAGGGCCTGGGCTCCAGCAT

CGAAAAGACCATCTCCAAGGCTAAGGGCCAGCCTCGGGAACCTCAGGTTTACACCCTGCCTCCAAGCCAAGAGGAAAT

GACCAAGAATCAGGTGTCCCTGACCTGTCTCGTGAAGGGCTTCTACCCTTCTGATATCGCCGTGGAATGGGAGTCCAA

CGGCCAGCCTGAGAACAACTACAAGACCACACCTCCAGTGCTGGACTCCGACGGCTCTTTCTTCCTGTATTCCCGCCT

GACCGTGGACAAGTCCAGATGGCAAGAGGGCAACGTGTTCTCCTGCAGCGTGCTGCATGAGGCTCTGCACTCCCACTA

CACCCAGAAGTCTCTGTCTCTGTCCCTGGGCAAGTGATAA
```

SEQ ID No. 95 protein sequence of P15 IgG₄ constant region
```
ASTKGPSVFPLAPCSRSTSESTAALGCLVKDYFPEPVTVSWNSGALTSGVHTFPAVLQSSGLYSLSSVVTVPSSSLGT

KTYTCNVDHKPSNTKVDKRVESKYGPPCPPCPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSFFLYSRLTVDKSRWQEGNVFSCSVMHEAL

HNHYTQKSLSLSLGK
```

SEQ ID No. 96 protein sequence of P15(GLS) constant region
```
ASTKGPSVFPLAPCSRSTSESTAALGCLVKDYFPEPVTVSWNSGALTSGVHTFPAVLQSSGLYSLSSVVTVPSSSLGT

KTYTCNVDHKPSNTKVDKRVESKYGPPCPPCPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKCKVSNKGLGSSIEKTISKAKGQPREPQVYTLPPS

QEEMTKNQVSLTCLVKGFYPSDIAVEWESNGQPENNYKTTPPVLDSDGSFFLYSRLTVDKSRWQEGNVFSCSVLHEAL

HSHYTQKSLSLSLGK
```

REFERENCES INCORPORATED IN CURRENT
PATENT APPLICATION

1. Harris C L, Pouw R B, Kavanagh D, Sun R, Ricklin D. Developments in anti-complement therapy; from disease to clinical trial. Mol Immunol. 2018; 102: 89-119.
2. Mastellos D C, Ricklin D, Lambris J D. Clinical promise of next-generation complement therapeutics. Nat Rev Drug Discov. 2019; 18: 707-29.
3. Please refer FDA approved product label of Eculizumab.
4. Zelek W M, Xie L, Morgan B P, Harris C L. Compendium of current complement therapeutics. Mol Immunol. 2019; 114: 341-52.
5. Ricklin D, Barratt-Due A, Mollnes T E. Complement in clinical medicine: Clinical trials, case reports and therapy monitoring. Mol Immunol. 2017; 89: 10-21.
6. Angal S, King D J, Bodmer M W, Turner A, Lawson A D, Roberts G, Pedley B, Adair J R. A single amino acid substitution abolishes the heterogeneity of chimeric mouse/human (IgG4) antibody. Mol Immunol. 1993; 30(1): 105-8.
7. Jones P T, Dear P H, Foote J, Neuberger M S, Winter G. Replacing the complementarity-determining regions in a human antibody with those from a mouse. Nature. 1986; 321(6069): 522-5.
8. Riechmann L, Clark M, Waldmann H, Winter G. Reshaping human antibodies for therapy. Nature. 1988; 332(6162): 323-7.
9. Verhoeyen M, Milstein C, Winter G. Reshaping human antibodies: grafting an antilysozyme activity. Science. 1988; 239(4847): 1534-6.
10. Almagro J C, Fransson J. Humanization of antibodies. Front Biosci. 2008; 13: 1619-33.
11. Wang X, Mathieu M, Brezski R J. IgG Fc engineering to modulate antibody effector functions. Protein Cell. 2018; 9(1): 63-73.
12. Schlothauer T, Herter S, Koller C F, Grau-Richards S, Steinhart V, Spick C, Kubbies M, Klein C, Umaña P, Mössner E. Novel human IgG1 and IgG4 Fc-engineered antibodies with completely abolished immune effector functions. Protein Eng Des Sel. 2016; 29(10): 457-466.

13. Wood J N. Immunization and fusion protocols for hybridoma production. Methods Mol Biol. 1984; 1: 261-70.

14. Kim H Y, Stojadinovic A, Izadjoo M J. Immunization, hybridoma generation, and selection for monoclonal antibody production. Methods Mol Biol. 2014; 1131: 33-45.

15. Honegger A, Pluckthun A. Yet another numbering scheme for immunoglobulin variable domains: an automatic modeling and analysis tool. J Mol Biol. 2001; 309(3): 657-70.

16. www.vbase2.org

17. Polhill R B Jr, Pruitt K M, Johnston R B Jr. Kinetic assessment of alternative complement pathway activity in a hemolytic system. I. Experimental and mathematical analyses. J Immunol. 1978; 121(1): 363-70.

18. Douglas P. Fine. Activation of the Classic and Alternate Complement Pathways by Endotoxin. J Immunol. 1974; 112(2); 763-9.

19. Clardy C W. Complement activation by whole endotoxin is blocked by a monoclonal antibody to factor B. Infect Immun. 1994; 62(10): 4549-55.

20. Bansal R, Brunden K, Parent J. Process for inhibiting complement activation via the alternative pathway. US20020015701.

21. Gullipalli D, Zhang F, Sato S, Ueda Y, Kimura Y, Golla M, Miwa T, Wang J, Song W C. Antibody Inhibition of Properdin Prevents Complement-Mediated Intravascular and Extravascular Hemolysis. J Immunol. 2018; 201(3): 1021-29.

22. Yuan F F, Bryant J A, Fletcher A. Protease-modified erythrocytes: CD55 and CD59 deficient PNH-like cells. Immunol Cell Biol. 1995; 73(1): 66-72.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. An anti-properdin antibody or antigen binding portion thereof comprising:
   (a) a CDRH1 comprising the amino acid sequence of SEQ ID NO:4,
   (b) a CDRH2 comprising the amino acid sequence of SEQ ID NO:10,
   (c) a CDRH3 comprising the amino acid sequence of SEQ ID NO:16,
   (c) a CDRL1 comprising the amino acid sequence of SEQ ID NO:23,
   (e) a CDRL2 comprising the amino acid sequence of SEQ ID NO:34, and
   (f) a CDRL3 comprising the amino acid sequence of SEQ ID NO:40.

2. The antibody or antigen binding portion thereof of claim 1 which comprises a heavy chain variable region comprising the amino acid sequence of SEQ ID NO:48 and a light chain variable region comprising the amino acid sequence of SEQ ID NO:61.

3. The antibody of claim 1 which binds to human properdin with a $K_D$ of $10^{-10}$ M or less.

4. The antibody of claim 1 which is an IgG4.

5. The antibody of claim 1 which has modified, reduced, or no ADCC and/or CDC activity.

6. The antibody of claim 1 which has ADCC and/or CDC activity.

7. The antibody or antigen binding portion thereof of claim 1,
   wherein the antibody or antigen binding portion thereof comprises at least one of the following characteristics:
   (a) cross-reacts with properdin from species other than human;
   (b) binding specificity towards human properdin;
   (c) prevents increased binding of C3b to target cell surface;
   (d) blocks properdin from mediating alternate complement pathway activation;
   (e) prevents complement mediated lysis of target cells;
   (f) regulates MAC formation on target cell surface thereby preventing lysis of the cells;
   (g) minimises formation of anaphylatoxins, C3a and C5a; and
   (h) increased half-life in a subject compared to an anti-properdin antibody with a conventional Fc fragment.

8. The antibody or antigen binding portion thereof of claim 1 which is humanized.

9. A composition comprising the antibody or antigen-binding portion thereof of claim 1 and a pharmaceutically acceptable carrier.

10. An immunoconjugate comprising the antibody or antigen-binding portion thereof of claim 1 linked to a therapeutic agent.

11. The immunoconjugate of claim 10, wherein the therapeutic agent is a cytotoxin or a radioactive isotope.

12. A bispecific molecule comprising the antibody, or antigen-binding portion thereof of claim 1 linked to a second functional moiety having a different binding specificity than said antibody or antigen-binding portion thereof.

13. The bispecific molecule as claimed in claim 12 wherein, the second functional moiety binds to an antigen selected from C3, C5, C5a, C5b, C3a, C3b, Factor B, Factor H and C1q.

14. A combination comprising at least two or more antibodies or antigen binding portions thereof wherein at least one antibody or antigen binding portion thereof is the antibody or antigen binding portion thereof of claim 1.

15. The combination of claim 14, wherein the combination comprises a second anti-properdin antibody.

* * * * *